(12) United States Patent
Simoneau et al.

(10) Patent No.: US 11,696,928 B2
(45) Date of Patent: Jul. 11, 2023

(54) COMPOUNDS AND USE THEREOF IN THE EXPANSION OF STEM CELLS AND/OR PROGENITOR CELLS

(71) Applicant: UNIVERSITE DE MONTREAL, Montréal (CA)

(72) Inventors: Bruno Simoneau, Laval (CA); Yves Chantigny, Pincourt (CA); Jonathan Yeh, Montréal (CA); Guy Sauvageau, Montréal (CA); Anne Marinier, Kirkland (CA)

(73) Assignee: UNIVERSITE DE MONTREAL, Montréal (CA)

( * ) Notice: Subject to any disclaimer, the term of this patent is extended or adjusted under 35 U.S.C. 154(b) by 473 days.

(21) Appl. No.: 16/760,780

(22) PCT Filed: Nov. 1, 2018

(86) PCT No.: PCT/IB2018/058593
§ 371 (c)(1),
(2) Date: Apr. 30, 2020

(87) PCT Pub. No.: WO2019/087129
PCT Pub. Date: May 9, 2019

(65) Prior Publication Data
US 2020/0323923 A1    Oct. 15, 2020

Related U.S. Application Data

(60) Provisional application No. 62/581,149, filed on Nov. 3, 2017.

(51) Int. Cl.
C07D 333/66 (2006.01)
C07D 495/04 (2006.01)
C12N 5/074 (2010.01)
A61K 35/28 (2015.01)

(52) U.S. Cl.
CPC ............ A61K 35/28 (2013.01); C07D 333/66 (2013.01); C07D 495/04 (2013.01); C12N 5/0607 (2013.01); C12N 2500/30 (2013.01)

(58) Field of Classification Search
None
See application file for complete search history.

(56) References Cited

U.S. PATENT DOCUMENTS

| | | | |
|---|---|---|---|
| 7,645,881 B2 | 1/2010 | Karp et al. |
| 9,301,949 B2 | 4/2016 | Byrd et al. |
| 2005/0139814 A1 | 6/2005 | Zhang et al. |
| 2006/0019976 A1 | 1/2006 | Karp et al. |
| 2006/0094724 A1 | 5/2006 | Kawaguchi et al. |
| 2006/0247273 A1 | 11/2006 | Kawaguchi et al. |
| 2006/0264484 A1 | 11/2006 | Hogarth et al. |
| 2012/0022046 A1 | 1/2012 | Byrd et al. |
| 2013/0129677 A1 | 5/2013 | Dai et al. |
| 2015/0011543 A1 | 1/2015 | Sauvageau et al. |
| 2016/0074373 A1 | 3/2016 | He et al. |
| 2016/0015263 A1 | 6/2016 | Olsen et al. |

FOREIGN PATENT DOCUMENTS

| | | | |
|---|---|---|---|
| CA | 2509510 A1 | 7/2004 | |
| CA | 2539471 A1 | 4/2005 | |
| CA | 2510519 C | 3/2010 | |
| CN | 1723210 A | 1/2006 | |
| CN | 1856488 A | 11/2006 | |
| CN | 102395273 A | 3/2012 | |
| CN | 104144931 A | 11/2014 | |
| CN | 105189474 A | 12/2015 | |
| JP | 2005097199 A | 4/2005 | |
| JP | 2005518446 A | 6/2005 | |
| JP | 2006516133 A | 6/2006 | |
| JP | 2012519174 A | 8/2012 | |
| JP | 2015504902 A | 2/2015 | |
| JP | 2016506929 A | 3/2016 | |
| WO | 98/22452 A1 | 5/1998 | |
| WO | 2004/058747 A1 | 7/2004 | |
| WO | 2010/099166 A1 | 9/2010 | |
| WO | 2011/147764 A1 | 12/2011 | |
| WO | 2013/126856 A1 | 8/2013 | |
| WO | 2013110198 A1 | 8/2013 | |
| WO | WO-2013110198 A1 * | 8/2013 | ............. A61K 35/28 |
| WO | 2014/089378 A1 | 6/2014 | |
| WO | 2014089378 A1 | 6/2014 | |

(Continued)

OTHER PUBLICATIONS

Fares, I.et al. "Screen for Small Molecules Capable of Expanding Human Hematopoietic Stem Cell Ex Vivo", Blood, vol. 118, No. 21, Nov. 2011 (Nov. 2011), pp. 836-837, 53rd Annual Meeting and Exposition of the American-Society-of-Hematology (ASH); San Diego, CA, USA; Dec. 10-13, 2011, (Abstract only).

Pabst, C. et al. "A High-Throughput Screen to Identify Compounds Preserving Primary Human AML Stem Cells Ex-Vivo", Blood, vol. 118, No. 21, Nov. 2011 (Nov. 2011), p. 1531,& 53rd Annual Meeting and Exposition of the American-Society-of-Hematology (ASH); San Diego, CA, USA; Dec. 10-13, 2011, (Abstract only).

Sztuba-Solinska J. et al. "Identification of biologically active, HIV TAR RNA-binding small molecules using small molecule microarrays", Journal of the American Chemical Society Jun. 11, 2014 American Chemical Society USA, vol. 136, No. 23, Jun. 11, 2014 (Jun. 11, 2014), pp. 8402-8410, DOI: 10.1021/ JA502754F.

(Continued)

*Primary Examiner* — Emily A Cordas

(74) *Attorney, Agent, or Firm* — Buchanan Ingersoll & Rooney P.C.

(57) ABSTRACT

The invention relates to compounds as described herein and pharmaceutical compositions containing them. Also, the invention relates to methods for expanding stem cells and/or progenitor cells and methods for treating a hematopoietic disorder/malignancy, an autoimmune disease and/or an inherited immunodeficient disease.

11 Claims, 4 Drawing Sheets

(56) References Cited

FOREIGN PATENT DOCUMENTS

WO   2014116859 A1   7/2014

OTHER PUBLICATIONS

Abulwerdi, F. et al. "Development of Small Molecules with a Non-Canonical Binding Mode to HIV-1 Trans Activation Response (TAR) RNA" J. Med. Chem. (2016), vol. 59, pp. 1-31.
Leung, E. et al.: "Synthesis and cytotoxicity of thieno[2,3-b]quinoline-2-carboxamide and cycloalkyl[b]thieno[3,2-e] pyridine-2-carboxamide derivatives" Accepted Manuscript, Bioorganic & Medicinal Chemistry, (2016), vol. 24, 35 pages.
Arabshahi, et al., "A Synthesis, in silico, in vitro and in vivo Study of Thieno[2,3-b]Pyridine Anticancer Analogues", MedChemComm, vol. 6, No. 11, 2015, pp. 1987-1997.
Avery, et al., "Influence of Infused Cell Dose and HLA Match on Engraftment After Double-unit Cord Blood Allografts", Blood, vol. 117, No. 12, Mar. 24, 2011, pp. 3277-3285.
Ballen, et al., "The National Marrow Donor Program 20 Years of Unrelated Donor Hematopoietic Cell Transplantation", Biology of Blood and Marrow Transplantation, vol. 14, 2008, pp. 2-7.
Cheuk, "Optimal Stem Cell Source for Allogeneic Stem Cell Transplantation for Hematological Malignancies", World Journal of Transplantation, vol. 3, No. 4, Dec. 24, 2013, pp. 99-112.
Doulatov, et al., "Revised Map of the Human Progenitor Hierarchy Shows the Origin of Macrophages and Dendritic Dells in Early Lymphoid Development", Nature Immunology, vol. 11, No. 7, Jul. 2010, pp. 585-593.
Fares, et al., "EPCR Expression Marks UM171-Expanded CD34+ Cord Blood Stem Cells", Blood, vol. 129, No. 25, Jun. 22, 2017, pp. 3344-3351.
Hung, et al., "Synthesis and Cytotoxicity of Thieno[2,3-b]Pyridine and Furo[2,3-b]Pyridine Derivatives", European Journal of Medicinal Chemistry, vol. 86, 2014, pp. 420-437.
Leonard, et al., "Stem Cell Transplantation in Sickle Cell Disease: Therapeutic Potential and Challenges Faced", Expert Review of Hematology, vol. 11, No. 7, 2018, 48 pages.
Majeti, et al., "Identification of a Hierarchy of Multipotent Hematopoietic Progenitors in Human Cord Blood", Cell Stem Cell, vol. 1, Dec. 2007, pp. 635-645.
Notta, et al., "Isolation of Single Human Hematopoietic Stem Cells Capable of Long-Term Multilineage Engraftment", Science, vol. 333, No. 6039, Jul. 8, 2011, pp. 218-221.
Remberger, et al., "Effect of Total Nucleated and CD34+ Cell Dose on Outcome After Allogeneic Hematopoietic Stem Cell Transplantation", Biology of Blood and Marrow Transplantation, vol. 21, No. 5, 2015, pp. 889-893.
Tiercy, "How to Select the Best Available Related or Unrelated Donor of Hematopoietic Stem Cells?", Haematologica, vol. 101, No. 6, 2016, pp. 680-687.
Office Action (The First Office Action) dated Aug. 12, 2022, by the State Intellectual Property Office of the People's Republic of China in corresponding Chinese Patent Application No. 201880074165.X, and an English Translation of the Office Action. (17 pages).
Office Action dated Sep. 6, 2022, by the Japanese Patent Office in corresponding Japanese Patent Application No. 2020-524269, and an English Translation of the Office Action. (6 pages).

* cited by examiner

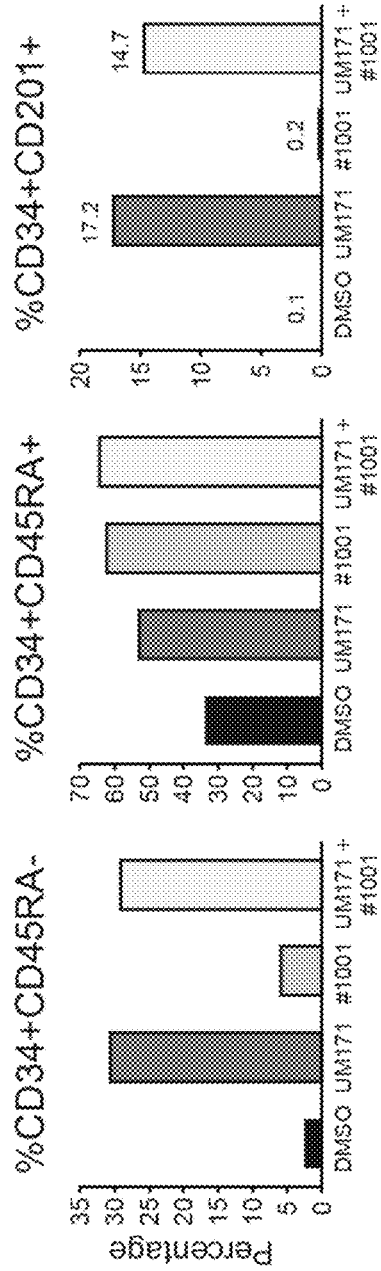
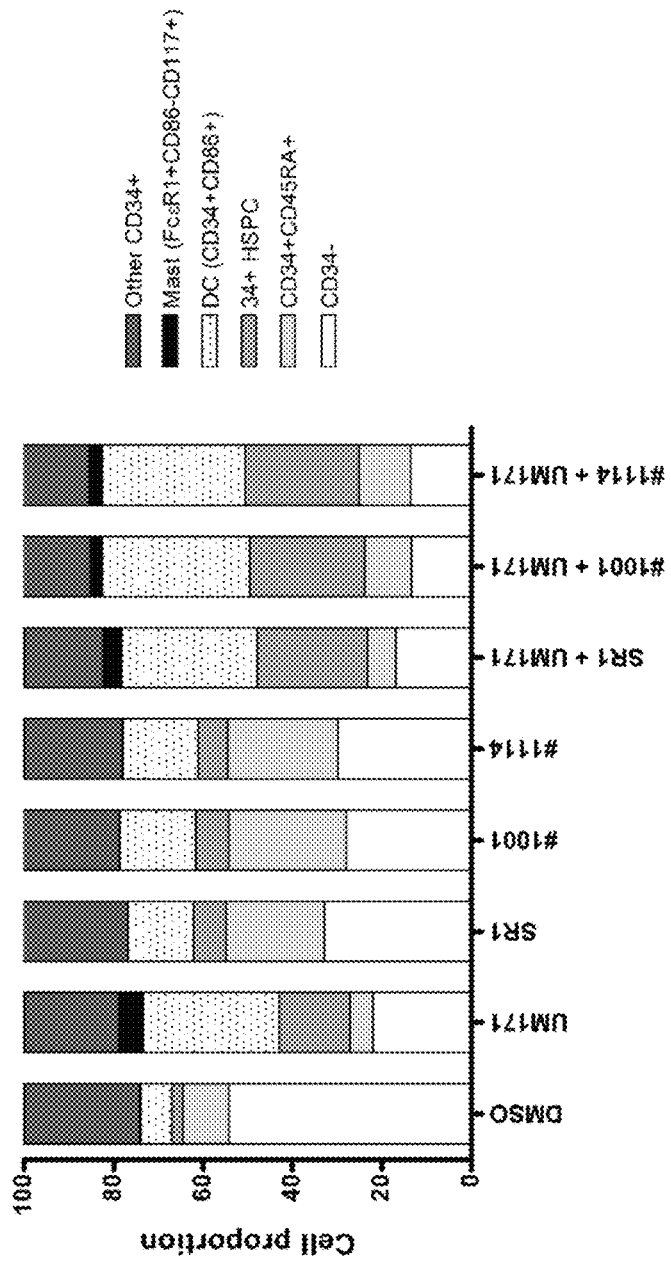

COMPOUNDS AND USE THEREOF IN THE EXPANSION OF STEM CELLS AND/OR PROGENITOR CELLS

CROSS REFERENCE TO RELATED APPLICATION

This application claims benefit of U.S. provisional application 62/581,149 filed Nov. 3, 2017, the content of which is entirely incorporated herein by reference.

FIELD OF THE DISCLOSURE

The invention relates to compounds as described herein and pharmaceutical compositions containing them. Also, the invention relates to methods for expanding stem cells and/or progenitor cells (HPCs) and methods for treating a hematopoietic disorder/malignancy, an autoimmune disease and/or an inherited immunodeficient disease.

BACKGROUND OF THE DISCLOSURE

The three sources of hematopoietic stem cells (HSCs) are the bone marrow, mobilized peripheral blood and the umbilical cord blood (UCB). HSCs are used in the transplantation setting (autologous or allogeneic) which constitutes one of the most effective treatment strategies for achieving cures in patients with hematologic malignancies, bone marrow failure conditions, a variety of congenital diseases of global concern (e.g. sickle cell anemia and thalassemia) and auto-immune diseases such as lupus. However, this opportunity for life-saving or life-improving treatment is not available to many thousands of people worldwide due to an inability to amplify these cells ex vivo sufficiently to make the procedure safe and successful. More particularly, for every 3 patients, one will forego the opportunity for transplant because no human leucocyte antigen (HLA) identical donor can be found. Another proportion of patients will not have access to transplantation simply because too few HSCs are available in the graft (i.e. cord blood or autologous) for successful transplant. The safety and efficacy of marrow transplant is directly dependent on the number of HSCs and HPCs available for engrafting. The more that can be infused, the more rapidly is hematologic function restored, and the shorter is the window of risk for infection due to lack of granulocytes or of bleeding due to lack of platelets. The challenge in providing sufficient HSCs is further escalated where non-myeloablative conditioning is preferred such as in the context of gene therapy for major inherited blood disorders (the major genetic cause of morbidity and mortality worldwide).

In adults, HSCs mainly reside in the bone marrow (BM) and must be mobilized to enter the circulation prior to being collected by apheresis, either for autologous or allogeneic hematopoietic stem cell transplantation (HSCT). The collection of an adequate number of CD34+ cells, a surrogate marker of (HSCs), is paramount because the dose of CD34+ cells influences the success and rate of hematopoietic recovery. Several reports suggest that a higher infused CD34+ cell dose is independently predictive of improved survival.

Allogeneic HSCT with BM or mobilized pheripheral blood stem cells (mPBSC) is another transplantation alternative. However, about one third to one fourth of the patients who are eligible for this type of transplant cannot find a suitable donor. For those who get transplanted, there is a high frequency of transplant related mortality due to graft-versus-host disease, relapse or graft rejection; and a risk of immunodeficiency for prolonged periods of time. Alternatively, umbilical cord blood has been shown as a valid option in allogeneic HSCT. However, a single cord blood (CB) unit typically provides insufficient HSCs for an adult patient for a rapid and efficient recovery.

There is thus a need for novel strategies for increasing the expansion of stem cells, progenitor cells, or both stem cells and progenitor cells.

SUMMARY OF THE DISCLOSURE

An aspect relates to a compound of formula I

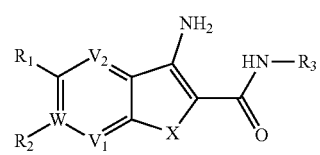

or a pharmaceutically acceptable salt thereof, wherein R1, R2, R3, V1, V2, X, and W are as defined herein.

A further aspect relates to a pharmaceutical composition comprising a compound as defined herein or a pharmaceutically acceptable salt thereof, and a pharmaceutically acceptable carrier.

A further aspect relates to a pharmaceutical composition comprising stem cells and/or progenitor cells expanded by a compound or method as defined herein.

In an aspect, there is provided a method of expanding stem cells and/or progenitor cells, as defined herein.

A further aspect relates to a cell population obtainable/obtained by a method as defined herein.

In an aspect, there is provided a method of treating a hematopoietic disorder/malignancy, an autoimmune disease and/or an inherited immunodeficient disease as defined herein.

A further aspect relates to a method of treating a hematopoietic disorder/malignancy, an autoimmune disease and/or an inherited immunodeficient disease, comprising administering a compound or a pharmaceutically acceptable salt thereof as defined herein to a subject in need thereof.

A further aspect relates to a method of treating a patient receiving an organ transplant, more particularly a solid organ transplant.

BRIEF DESCRIPTION OF THE FIGURES

Reference is now made to the accompanying figures in which:

FIG. 1C depicts the proportions of CD34+CD45RA−, CD34+CD45RA+ and CD34+CD201+ cells in the different culture conditions;

FIG. 1D depicts the cell composition in percentages of different cell types in the different culture conditions;

DETAILED DESCRIPTION OF THE DISCLOSURE

Figure 1A:
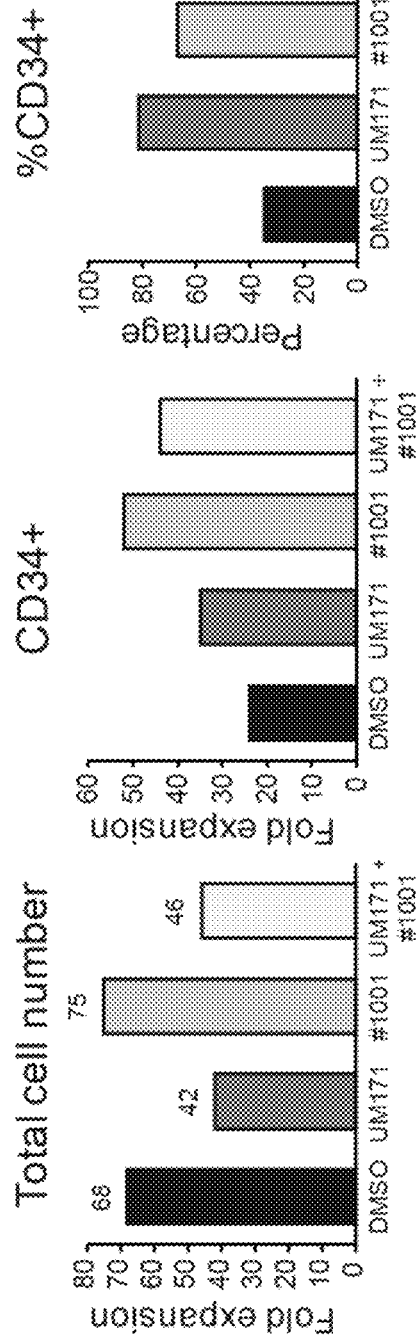
FIG. 1A depicts the fold expansion of total cells and CD34+ cells in the different culture conditions compared to fresh samples, as well as the proportions of CD34+ cells in the different culture conditions.

In one embodiment, there is provided a compound of formula I

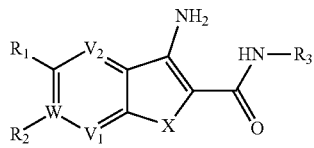

I or a pharmaceutically acceptable salt thereof, wherein

X is O or S;

V1 is N or CH;

V2 is N or CH;

W is N or C;

wherein not more than one of said V1, V2 and W is N;

$R_1$ is halo, alkyl, fluoroalkyl, cycloalkyl, alkynyl, alkenyl, cyano, or COORa, wherein Ra is an alkyl;

$R_2$ is H, alkyl or R2 is absent when W is N;

or $R_1$ and $R_2$ are attached together with the aromatic ring atoms to form a carbocyclic ring;

$R_3$ is an optionally substituted phenyl, an optionally substituted 5- or 6-membered heteroaryl, or an optionally substituted fused bicyclic heteroaryl.

In one embodiment, said compound is a compound of formula Ia

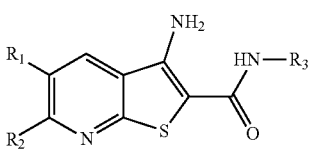

Ia wherein $R_1$, $R_2$ and $R_3$ are as defined herein.

In one embodiment, said compound is a compound of formula Ib

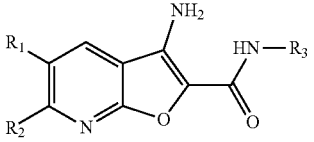

Ib wherein $R_1$, $R_2$ and $R_3$ are as defined herein.

In one embodiment, said compound is a compound of formula Ic

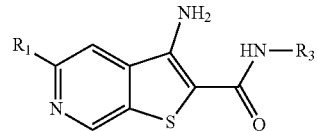

Ic wherein $R_1$ and $R_3$ are as defined herein.

In one embodiment, said compound is a compound of formula Id

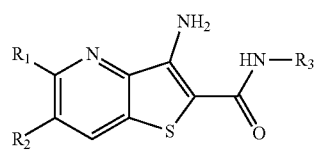

Id wherein $R_1$, $R_2$ and $R_3$ are as defined herein.

In one embodiment, said compound is a compound of formula Ie

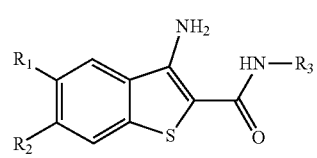

Ie wherein $R_1$, $R_2$ and $R_3$ are as defined herein.

In one embodiment, $R_1$ is halo, C1-6alkyl, C1-6fluoroalkyl, C3-6cycloalkyl, C2-3alkynyl, C2-3alkenyl, cyano, or COORa wherein Ra is a C1-6alkyl.

In one embodiment, $R_1$ is halo, C1-3alkyl, C1-3fluoroalkyl, C3-6cycloalkyl, C2-3alkynyl, C2-3alkenyl, cyano, or COORa wherein Ra is a C1-3alkyl.

In one embodiment, $R_1$ is F, Cl, Br, Me, Et, iPr, n-Pr, $CF_3$, cyclopropyl, CCH, CH=CMe, cyano, or COOEt.

In one embodiment, $R_1$ is F, Me, Et, iPr, n-Pr, $CF_3$, cyclopropyl, CCH, CH=CMe, cyano, or COOEt.

In one embodiment, $R_1$ is Me, $CF_3$, or joined to $R_2$ to form $(CH_2)_{3-5}$ ring.

In one embodiment, $R_1$ is Me or $CF_3$, preferably $CF_3$.

In one embodiment, $R_2$ is H, or C1-6alkyl.

In one embodiment, $R_2$ is H, or C1-3alkyl.

In one embodiment, $R_2$ is H or Me, preferably H.

In one embodiment, $R_2$ is H, methyl, ethyl, i-propyl or n-propyl; or preferably H or methyl.

In one embodiment, $R_1$ and $R_2$ are attached together to form $(CH_2)_{3-5}$.

In one embodiment, $R_3$ is an optionally mono or disubstituted phenyl, an optionally monosubstituted 5- or 6-membered heteroaryl, or an optionally monosubstituted fused bicyclic heteroaryl.

In one embodiment, $R_3$ is an optionally mono or disubstituted phenyl at any of positions 3, 4 and of said phenyl, an optionally monosubstituted 5- or 6-membered heteroaryl, or an optionally monosubstituted fused bicyclic heteroaryl of 9 or 10 members.

In one embodiment, $R_3$ is an unsubstituted phenyl, a phenyl monosubstituted at position 4, a phenyl monosubstituted at position 3, a phenyl disubstituted at positions 3 and 4, or a phenyl disubstituted at positions 3 and 5.

In one embodiment, $R_3$ is an unsubstituted or monosubstituted heteroaryl selected from pyridinyl, pyrimidinyl, thiazolyl, benzothiazolyl, isoquinolinyl, quinolinyl, thienyl and indazolyl.

In one embodiment, $R_3$ is an unsubstituted or monosubstituted heteroaryl selected from 2-pyridinyl, 3-pyridinyl, 4-pyridinyl, 2-thiazolyl, 6-benzothiazolyl, 5-isoquinolinyl, 3-quinolinyl, 4-quinolinyl, 5-quinolinyl, 6-quinolinyl, 3-thienyl and 5-indazolyl.

In one embodiment, $R_3$ is an unsubstituted or monosubstituted heteroaryl selected from 2-pyridinyl, 3-pyridinyl, 4-pyridinyl, and 3-thienyl.

In one embodiment, when $R_3$ is substituted phenyl, said substituent is halo, optionally substituted C1-3alkyl, —O—C1-3fluoroalkyl, —O—C1-3alkyl, —O-benzyl, —O-phenyl, —S—C1-3alkyl, sulfonamide, C1-3fluoroalkyl, —COO—C1-3alkyl, carboxamide, amino, phenyl, 5- or 6-membered heteroaryl or two substituents of $R_3$ form together —O(CH$_2$)$_{3-5}$O— wherein the substituent of said optionally substituted C1-3alkyl is OH, OMe, CN, or COOEt.

In one embodiment, when $R_3$ is substituted phenyl, said substituent is halo, optionally substituted C1-3alkyl, —O—C1-3fluoroalkyl, —O—C1-3alkyl, —O-benzyl, —O-phenyl, —S—C1-3alkyl, —SO$_2$NH(C1-3alkyl) —SO$_2$N(C1-3alkyl)$_2$, —SO$_2$NH$_2$, C1-3fluoroalkyl, —COO—C1-3alkyl, —CONH(C1-3alkyl), —CON(C1-3alkyl)$_2$, —CONH$_2$, —NH(C1-3alkyl), —N(C1-3alkyl)$_2$, —NH$_2$, phenyl or 5- or 6-membered heteroaryl; or two substituents of $R_3$ form together —O(CH$_2$)O— or —O(CH$_2$CH$_2$)O—; wherein the substituent of said optionally substituted C1-3alkyl is OH, OMe, CN, or COOEt.

In one embodiment, when $R_3$ is substituted phenyl, said substituent is F, Cl, Br, Me, Et, CH$_2$OH, CH$_2$OMe, CH$_2$CH$_2$OH, CH$_2$CH$_2$OMe, CH$_2$CN, CH$_2$COOEt, OCF$_3$, OCHF$_2$, —OMe, —O-benzyl, —O-phenyl, —SMe, —SO$_2$NH$_2$, CF$_3$, COOMe, —CONHMe, —CONH$_2$, —NH$_2$, 3-pyridinyl, 4-pyridinyl, or two substituents of $R_3$ form together form —O(CH$_2$)O— or —O(CH$_2$CH$_2$)O—.

In one embodiment, when $R_3$ is substituted phenyl, said substituent is halo, —S—C1-3alkyl, —O—C1-3fluoroalkyl, —O—C1-3alkyl or two substituents of $R_3$ form together —O(CH$_2$)$_{3-5}$O—.

In one embodiment, when $R_3$ is phenyl substituted at position 4 with H, F, Cl, Br, Me, Et, OMe, OEt, SMe or CF$_3$.

In one embodiment, when $R_3$ is phenyl substituted at position 3 with H, F, C, Br, Me, or OMe.

In one embodiment, when $R_3$ is phenyl substituted at position 3 and 4 together form —CH$_2$O—, or —OCH$_2$CH$_2$O—.

In one embodiment, when $R_3$ is substituted heteroaryl, said substituent is halo, optionally substituted C1-3alkyl, —O—C1-3fluoroalkyl, —O—C1-3alkyl, —O-benzyl, —O-phenyl, —S—C1-3alkyl, —SO$_2$NH(C1-3alkyl) —SO$_2$N(C1-3alkyl)$_2$, —SO$_2$NH$_2$, C1-3fluoroalkyl, —COO—C1-3alkyl, —CONH(C1-3alkyl), —CON(C1-3alkyl)$_2$, —CONH$_2$, —NH(C1-3alkyl), —N(C1-3alkyl)$_2$, —NH$_2$, phenyl or 5- or 6-membered heteroaryl; or two substituents of $R_3$ form together —O(CH$_2$)O— or —O(CH$_2$CH$_2$)O—; wherein the substituent of said optionally substituted C1-3alkyl is OH, OMe, CN, or COOEt.

In one embodiment, when $R_3$ is substituted heteroaryl, said substituent is F, Cl, Br, Me, Et, CH$_2$OH, CH$_2$OMe, CH$_2$CH$_2$OH, CH$_2$CH$_2$OMe, CH$_2$CN, CH$_2$COOEt, OCF$_3$, OCHF$_2$, —OMe, —O— benzyl, —O-phenyl, —SMe, —SO$_2$NH$_2$, CF$_3$, COOMe, —CONHMe, —CONH$_2$, —NH$_2$, 3-pyridinyl, 4-pyridinyl, or two substituents of $R_3$ form together form —O(CH$_2$)O— or —O(CH$_2$CH$_2$)O—.

In one embodiment, when $R_3$ is substituted heteroaryl, such as 2-, 3-, 4-pyridyl or thienyl, said substituent is halo, C1-3alkyl, or —O—C1-3alkyl, preferably $R_3$ is 4-pyridinyl or 3-thienyl.

In one embodiment, in formula I, or in any of formula Ia to Ie, preferably in formula Ia and Ie, $R_1$ is C1-6alkyl, C1-6fluoroalkyl, $R_2$ is H or $R_1$ is joined to $R_2$ to form (CH$_2$)$_{3-5}$, $R_3$ is an unsubstituted phenyl, a phenyl monosubstituted at position 4, a phenyl monosubstituted at position 3, a phenyl disubstituted at positions 3 and 4, or a phenyl disubstituted at positions 3 and 5 or $R_3$ is an unsubstituted or monosubstituted heteroaryl selected from pyridinyl, pyrimidinyl, thiazolyl, benzothiazolyl, isoquinolinyl, quinolinyl, thienyl and indazolyl.

In one embodiment, in formula I, or in any of formula Ia to Ie, preferably in formula Ia and Ie, $R_1$ is halo, C1-3alkyl, C1-3fluoroalkyl, C3cycloalkyl, C2-3alkynyl, C2-3alkenyl, cyano, or COORa wherein Ra is a C1-3alkyl, preferably $R_1$ is Me, CF$_3$, or joined to $R_2$ to form (CH$_2$)$_{3-5}$ ring; $R_2$ is H, $R_3$ is an unsubstituted phenyl, a phenyl monosubstituted at position 4, a phenyl monosubstituted at position 3, a phenyl disubstituted at positions 3 and 4, or a phenyl disubstituted at positions 3 and 5 wherein said phenyl substituent(s) is F, Cl, Br, Me, Et, CH$_2$OH, CH$_2$OMe, CH$_2$CH$_2$OH, CH$_2$CH$_2$OMe, CH$_2$CN, CH$_2$COOEt, OCF$_3$, OCHF$_2$, —OMe, —O-benzyl, —O-phenyl, —SMe, —SO$_2$NH$_2$, CF$_3$, COOMe, —CONHMe, —CONH$_2$, —NH$_2$, 3-pyridinyl, 4-pyridinyl, or two substituents of $R_3$ together form —O(CH$_2$)O— or —O(CH$_2$CH$_2$)O— or $R_3$ is an unsubstituted or monosubstituted heteroaryl selected from 2-pyridinyl, 3-pyridinyl, 4-pyridinyl, and 3-thienyl, wherein said substituent is halo, C1-3alkyl, or —O—C1-3alkyl.

In one embodiment, in formula I, or in any of formula Ia to Ie, preferably in formula Ia, $R_1$ is C1-3alkyl, or C1-3fluoroalkyl, preferably $R_1$ is Me; $R_2$ is H, $R_3$ is a phenyl monosubstituted at position 4, or a phenyl disubstituted at positions 3 and 4, wherein said phenyl substituent(s) is F, Cl, Br, Me, Et, CH$_2$OH, CH$_2$OMe, CH$_2$CH$_2$OH, CH$_2$CH$_2$OMe, CH$_2$CN, CH$_2$COOEt, OCF$_3$, OCHF$_2$, —OMe, —O-benzyl, —O-phenyl, —SMe, —SO$_2$NH$_2$, CF$_3$, COOMe, —CONHMe, —CONH$_2$, —NH$_2$, 4-pyridinyl, or two substituents of $R_3$ together form —O(CH$_2$)O— or —O(CH$_2$CH$_2$)O—, preferably said phenyl substituent is F, —Cl, —SMe, —OMe, CF$_3$ or two substituents form —O(CH$_2$CH$_2$)O—, or $R_3$ is an unsubstituted or monosubstituted heteroaryl selected from 2-pyridinyl, 3-pyridinyl, 4-pyridinyl, and 3-thienyl, preferably said heteroaryl is an unsubstituted 3-thienyl.

In one embodiment, compound of formula I is compounds of Tables 1 or 2.

In one embodiment, compound of formula I is

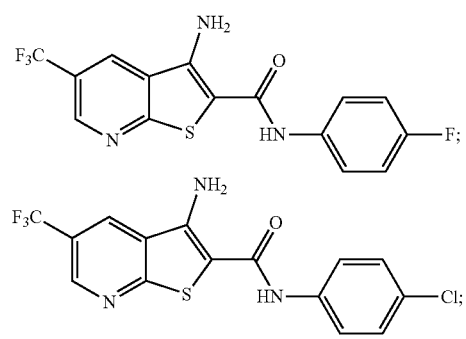

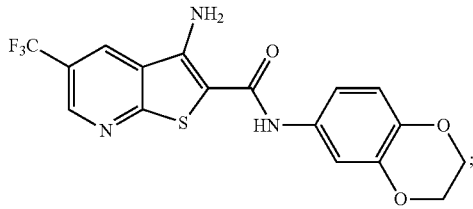

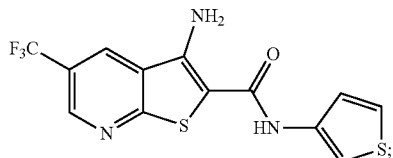

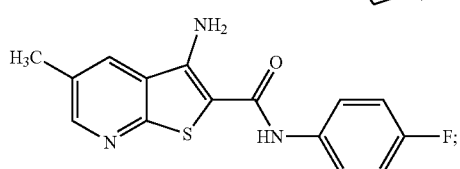

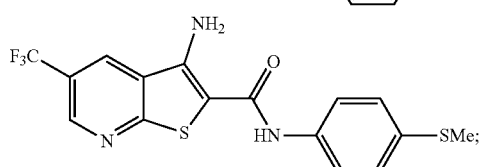

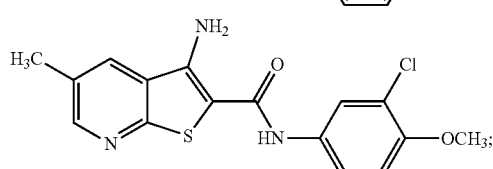

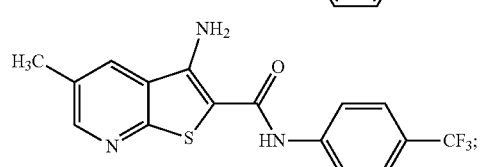

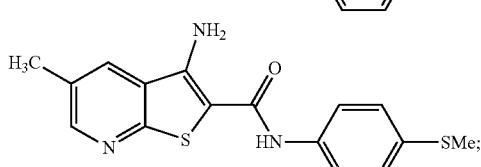

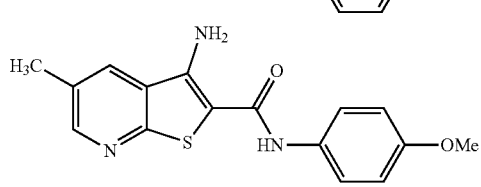

or a pharmaceutically acceptable salt thereof.

In one embodiment, compound of formula I is

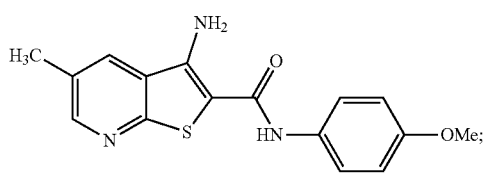

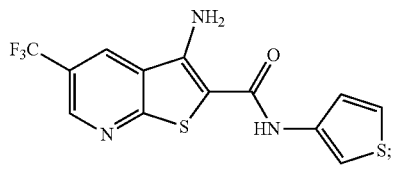

or a pharmaceutically acceptable salt thereof.

The methods as defined herein enjoy the use of the full scope of the compounds as contemplated by the inventors. The compounds that are excluded from the scope of the claimed compounds are those defined by the following provisos or as enumerated below.

Generic proviso 1: when V1 is N, X is S, $R_1$ and $R_2$ together form $(CH_2)_{3-5}$ and $R_3$ is phenyl, then said phenyl is other than i) unsubstituted phenyl or ii) phenyl substituted at position 4 by F, Cl or OMe, for example when said compound is of formula I or Ia.

Generic proviso 1a: where V1 is N, X is S, $R_1$ and $R_2$ together form $(CH_2)_{3-5}$, $R_3$ is optionally substituted 5- or 6-membered heteroaryl, or an optionally substituted fused bicyclic heteroaryl, a phenyl monosubstituted at position 3, phenyl disubstituted at positions 3 and 4, a phenyl disubstituted at positions 3 and 5, a phenyl monosubstituted at position 4 by Br, optionally substituted C1-3alkyl, —O—C1-3fluoroalkyl, —O—C2-3alkyl, —O-benzyl, —O-phenyl, —S—C1-3alkyl, —SO$_2$NH(C1-3alkyl) —SO$_2$N(C1-3alkyl)$_2$, —SO$_2$NH$_2$, C1-3fluoroalkyl, —COO—C1-3alkyl, —CONH(C1-3alkyl), —CON(C1-3alkyl)$_2$, —CONH$_2$, —NH(C1-3alkyl), —N(C1-3alkyl)$_2$, or —NH$_2$, for example when said compound is of formula I or Ia.

Generic proviso 2: when V1 is N, X is S, $R_3$ is unsubstituted phenyl and $R_2$ is H, then $R_1$ is other than Cl or Br, for example when said compound is of formula I or Ia.

Generic proviso 3: when V1 and V2 are CH, W is C, X is S, $R_2$ is H, $R_1$ is CH$_3$ and $R_3$ is phenyl, then said phenyl is other than i) unsubstituted phenyl or ii) phenyl substituted at position 4 by F, Cl, Br or Me, for example when said compound is of formula I or Ie.

Alternatively, the compounds that are excluded from the scope of the claimed compounds are:

CAS: 309741-87-5

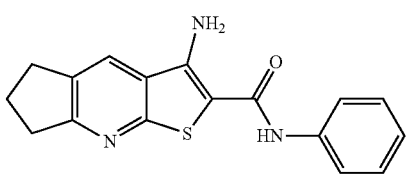

CAS: 428449-34-7

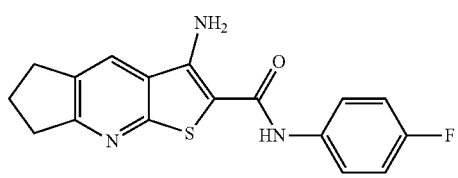

-continued

CAS: 340813-04-9
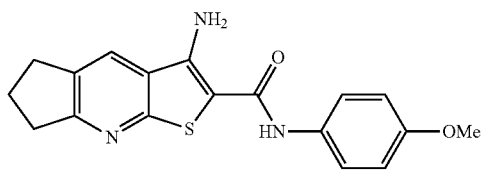

CAS: 428444-64-8
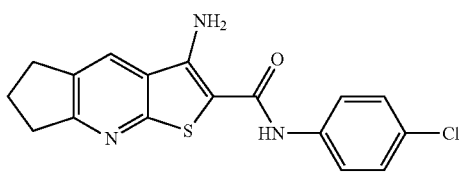

CAS: 361198-68-7
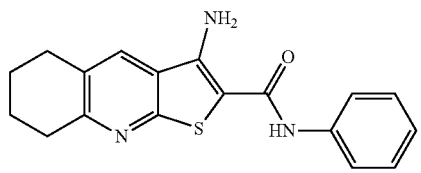

CAS: 340813-02-7
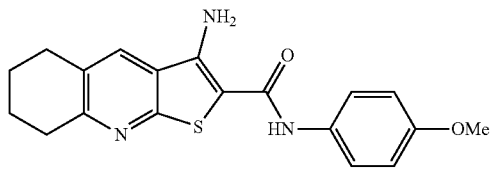

CAS: 428451-61-0
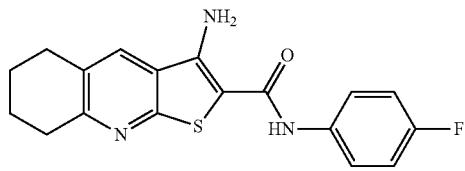

CAS: 298219-02-0
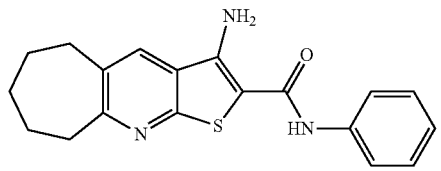

CAS: 1628934-21-3
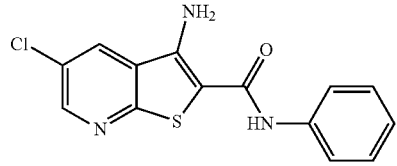

CAS: 1628934-24-6
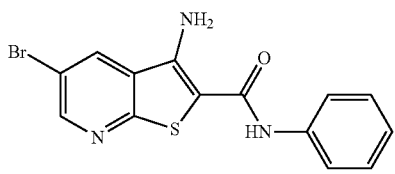

-continued

CAS: 1927343-65-4
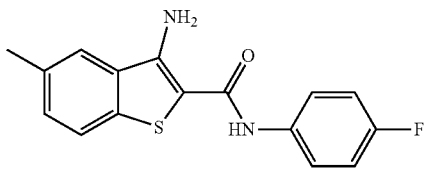

CAS: 1927344-00-0
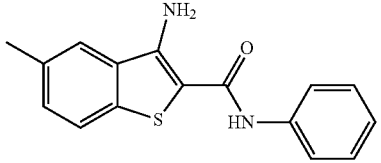

CAS: 1942440-87-0
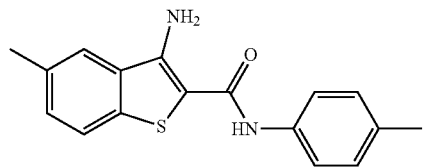

CAS: 1962685-12-6
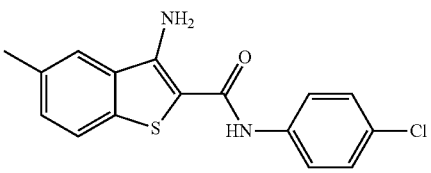

CAS: 1939271-31-4
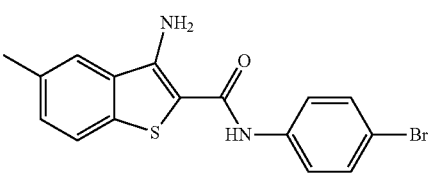

When there is a sulfur atom present (such as a core ring atom), the sulfur atom can be at different oxidation levels, ie. S, SO, or $SO_2$. All such oxidation levels are within the scope of the present disclosure. When there is a nitrogen atom present, the nitrogen atom can be at different oxidation levels, i.e. N or NO. All such oxidation levels are within the scope of the present disclosure.

The term "alkyl", as used herein, unless otherwise defined is understood as referring to a saturated, monovalent unbranched or branched hydrocarbon chain. Examples of alkyl groups include, but are not limited to, C1-10 alkyl groups, provided that branched alkyls comprise at least 3 carbon atoms, such as C3-10. Straight alkyl may have 1 to 6 or preferably 1 to 3 carbon atoms; whereas branched alkyl comprise C3-6. Examples of alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl.

The term "alkenyl" is meant to include alkyl residues in which one or more single bond(s) is replaced by a double bond.

The term "alkynyl" is meant to include alkyl residues in which one or more single bond(s) is replaced by a triple bond.

The term "fluoroalkyl" is meant to include alkyls in which one or more hydrogen atom is replaced by a fluoride atom of all alkyls defined above: straight or branched fluoroalkyls and straight or branched lower fluoroalkyls, such as trifluoromethyl, difluoromethyl, fluoromethyl, trichloromethyl, dichloromethyl, chloromethyl, trifluoroethyl, difluoroethyl, fluoroethyl.

The term "cycloalkyl" represents optionally substituted cyclic alkyl moiety having 3 to 10 carbon atoms. Examples of "cycloalkyl" groups include but are not limited to cyclopropyl, cyclobutyl, cyclopentyl, and cyclohexyl.

The term "carbocyclic ring" in the definition of $R_1$ and $R_2$ preferably refers to an alkyl chain forming a ring with the aromatic ring atoms to which they are attached, even more preferably the carbocyclic ring refers to a chain $(CH_2)_{3-5}$ forming a ring with the aromatic ring atoms to which they are attached.

The term "heteroaryl" represents a 5 to 11 membered aromatic cyclic moiety wherein said cyclic moiety is comprising at least one heteroatom selected from oxygen (O), sulfur (S) or nitrogen (N). Heteroaryls may be monocyclic or polycyclic rings. Heteroaryls may be 5 to 6 membered monocyclic ring or 5 membered monocyclic ring or 6 membered monocyclic ring. Heteroaryls may be fused 6,6, or 5,6 bicyclic rings. When heteroaryl is a polycyclic ring, the rings comprise at least one ring comprising the heteroatom and the other rings may be cycloalkyl, aryl or heterocycle and the point of attachment may be on any available atom. This term includes without limitation, for example, furyl, thienyl, pyrrolyl, imidazolyl, oxazolyl, thiazolyl, triazolyl, tetrazolyl, pyridinyl, pyrazinyl, pyrimidinyl, pyridazinyl, benzothiazolyl, quinolinyl, isoquinolinyl, indolyl and indazolyl.

There is also provided pharmaceutically acceptable salts of the compounds of the present disclosure. What is meant by the term pharmaceutically acceptable salts of the compounds is that they are derived from pharmaceutically acceptable inorganic and organic acids and bases.

For example, conventional non-toxic salts include those derived from inorganic acids such as hydrochloric, hydrobromic, sulfuric, sulfamic, phosphoric, nitric, perchloric and the like, as well as salts prepared from organic acids such as formic, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, benzenesulphonic, naphthalene 2 sulphonic, ethane disulfonic, oxalic, isethionic, trifluoroacetic and the like.

Other salts, while not in themselves pharmaceutically acceptable, may be useful as intermediates in obtaining the compounds of the disclosure and their pharmaceutically acceptable acid addition salts. Salts derived from appropriate bases include alkali metal, alkaline earth metal or ammonium salts.

The pharmaceutically acceptable salts of the compounds of this disclosure can be synthesized from the compounds of this disclosure which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

In one embodiment there is provided a pharmaceutical composition comprising a compound as defined herein or a pharmaceutically acceptable salt thereof, and a pharmaceutically acceptable carrier.

In one embodiment there is provided a pharmaceutical composition comprising stem cells and/or progenitor cells expanded by a compound or method as defined herein.

The pharmaceutical composition may be further comprising a buffer solution or a an additional pharmaceutically active component, such as an antibiotic.

In one embodiment the pharmaceutical composition as defined herein, is for intravenous administration.

In one embodiment there is provided a method of expanding stem cells and/or progenitor cells, (such as hematopoietic stem and/or progenitor cells) the method comprising contacting a starting cell population and at least one compound or a pharmaceutically acceptable salt thereof as defined herein.

In one embodiment of the methods herein, said methods are comprising the steps of contacting stem cells and/or progenitor cells (such as hematopoietic stem and/or progenitor cells) with a compound for expanding stem cells and/or progenitor cells and at least one compound or a pharmaceutically acceptable salt thereof as defined herein.

In one embodiment of the methods herein, said methods are comprising the steps of contacting stem cells and/or progenitor cells (such as hematopoietic stem and/or progenitor cells) with a first compound for expanding stem cells and/or progenitor cells, expanding the cells for a first period of time, adding at least one compound or a pharmaceutically acceptable salt thereof as defined herein and expanding the cells further for a second period of time.

In one embodiment of the methods herein, said methods are comprising the steps of contacting stem cells and/or progenitor cells (such as hematopoietic stem and/or progenitor cells) with a first compound for expanding stem cells and/or progenitor cells, expanding the cells for a first period of time, substantially removing said first compound (e.g. by washing the expanded cells with an appropriate wash medium), contacting said cells expanded from said first period of time with at least one compound or a pharmaceutically acceptable salt thereof as defined herein and expanding the cells further for a second period of time.

A (first) compound for expanding stem cells, other than a compound of this invention (formula I, or Ia-Ie) may be a compound of formula

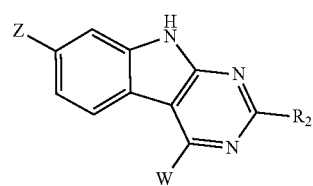

such as those described in WO 2013/110198 (PCT/CA2013/050052), the content of which is incorporated herein by reference in it's entirety. In particular, the compound may be one of the following:

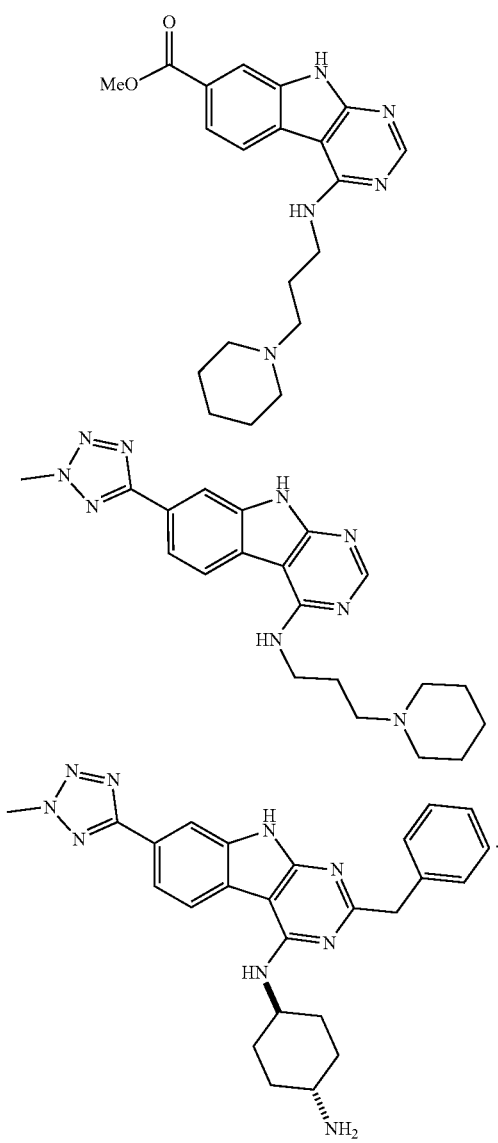

The method of expanding stem cells and/or progenitor cells as defined herein, may further be comprising at least one cell expanding agent.

In one embodiment of the method of expanding hematopoietic stem cells and/or progenitor cells as defined herein, said cell expanding agent is an agonist antibody against the Thrombopoietin (TPO) receptor (for example, VB22B sc(Fv)2 as detailed in patent publication WO 2007/145227, and the like); a cytokine such as SCF, IL-6, Flt-3 ligand, TPO or a TPO mimetic (for example, such as described in WO/2007/022269; WO/2007/009120; WO/2004/054515; WO/2003/103686; WO/2002/085343; WO/2002/049413; WO/2001/089457; WO/2001/039773; WO/2001/034585; WO/2001/021180; WO/2001/021180; WO/2001/017349; WO/2000/066112; WO/2000/035446; WO/2000/028987; WO/2008/028645; and the like, which are incorporated herein by reference); granulocyte colony stimulating factor (G-CSF); granulocyte macrophage colony stimulating factor (GM-CSF); a prostaglandin or a prostaglandin receptor agonist (for example, prostaglandin E2 receptor-1 (EP-1) agonist, prostaglandin E2 receptor-2 (EP-2) agonist, prostaglandin E2 receptor-3 (EP-3) agonist and prostaglandin E2 receptor-4 (EP-4) agonists, as detailed in patent publication WO/2008/073748 which is incorporated herein by reference); tetraethylenepentamine (TEPA); Notch-ligands (Delta-1); and/or a WNT agonist. These publications and their content are incorporated herein by reference.

Preferably the cell expanding agent is selected from Interleukin-3 (IL-3), Granulocyte Macrophage Colony-Stimulating Factor (GM-CSF), Thrombopoietin (TPO), FMS-Like Tyrosine Kinase 3 Ligand (FLT3-L), Stem Cell Factor (SCF), Interleukin-6 (IL-6) and a combination thereof.

The cell expanding agent may be SCF, FLT3-L, TPO, IL-6 or a combination thereof. In one embodiment of the method of expanding stem cells (such as hematopoietic stem cells) and/or progenitor cells as defined herein, said cell expanding agent, is StemRegenin 1 (SR1).

In one embodiment there is provided a method of modulating (antagonizing) the activity of aryl hydrocarbon receptor, comprising contacting stem cells and progenitor cells with a compound as defined herein.

In one embodiment there is further provided a method of increasing the number of stem cells and progenitor cells; said method comprising contacting the cells with a compound capable of antagonizing the activity and/or expression of aryl hydrocarbon receptor and/or a downstream effector of aryl hydrocarbon receptor pathway, wherein said compound is a compound as defined herein.

In one embodiment there is provided a method of expanding stem cells (such as hematopoietic stem cells) and/or progenitor cells as defined herein, wherein hematopoietic stem cells and/or progenitor cells are human hematopoietic stem and progenitor cells.

In one embodiment there is provided a method of expanding CD34+ stem cells and/or progenitor cells as defined herein, wherein CD34+ stem cells and/or progenitor cells are human hematopoietic stem and progenitor cells.

In one embodiment the starting cell population is comprising CD34+ cells harvested from mobilized peripheral blood (mPB), bone marrow (BM) or umbilical cord blood (UCB). In one embodiment, the starting cell population is human CD34+ stem cells and/or progenitor cells.

In one embodiment the starting cell population includes CD34+ cells harvested from umbilical cord blood (UCB).

In one embodiment the starting cell population consists essentially of CD34+ cells, for example purified from one or two umbilical cord blood units.

The expanded cells may then be washed to remove the compound or composition of invention and/or any other component of the cell culture and resuspended in an appropriate cell suspension medium for short term use or in a long-term storage medium, for example a medium suitable for cryopreservation.

A preferred method of administration of expanded cells or a composition comprising said expanded cells is intravenous infusion. The number of cells transfused will take into consideration factors such as sex, age, weight, the types of disease or disorder, stage of the disorder, the percentage of the desired cells in the cell population and the amount of cells needed to produce a therapeutic benefit. In one particular embodiment, the composition is administered by intravenous infusion and comprises at least ≥0.3×10$^5$ CD34$^+$/kg or >2×10$^6$ CD34$^+$ for cord blood and 2.5×10$^5$ CD34$^+$/kg or more for bone marrow or mobilized peripheral blood cells.

Expanded stem cells (such as hematopoietic stem cells) and/or hematopoietic progenitor cells may be infused by drip, for example, in the case of treatment of leukemia, into patients pretreated with an anticancer drug, total body irradiation or an immunosuppressive drug for eradication of cancer cells or for facilitation of donor cell engraftment. The disease to be treated, the pretreatment and the cell transplantation method are selected appropriately by the person in charge. The engraftment of so transplanted hematopoietic stem cells and/or hematopoietic progenitor cells in the recipient, the recovery of hematopoiesis, the presence of side effects of the transplantation and the therapeutic effect of the transplantation can be judged by an ordinary assay used in transplantation therapy.

In one embodiment of the method of expanding stem cells and/or progenitor cells as defined herein, said method is in vivo, in vitro or ex vivo, in particular, the method is ex vivo or in vitro.

In one embodiment, there is provided a cell population as expanded by a method as defined herein.

In one embodiment, there is provided a method of treating a hematopoietic disorder/malignancy, an autoimmune disease and/or an inherited immunodeficient disease, comprising administering expanded stem cells (such as hematopoietic stem cells) as defined herein to a subject in need thereof or expanding hematopoietic stem cells by a method as defined herein and administering said expanded stem cells to a subject in need thereof.

There is further provided a cell population with expanded HSCs, obtainable or obtained by the expansion method described above. In one specific embodiment, such cell population is resuspended in a pharmaceutically acceptable medium suitable for administration to a mammalian host, thereby providing a therapeutic composition.

There is further provided a method of treating a hematopoietic disorder/malignancy, an autoimmune disease and/or an inherited immunodeficient disease, comprising administering a compound or a pharmaceutically acceptable salt thereof as defined herein to a subject in need thereof.

In one embodiment, of the methods as defined herein, the hematopoietic disorder/malignancy, the autoimmune disease and/or the inherited immunodeficient disease comprise bone marrow failure conditions, a congenital diseases (such as sickle cell anemia and thalassemia), lupus, acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin's lymphoma, Hodgkin's disease, aplastic anemia, pure red cell aplasia, hemoglobinuria, Fanconi anemia, thalassemia, sickle cell anemia, Wiskott-Aldrich syndrome, inborn errors of metabolism (such as Gaucher disease).

In one embodiment, there is provided a method of treating a patient receiving an organ from a transplantation (ex. solid organ transplantation), comprising administering expanded stem cells (such as hematopoietic stem cells) as defined herein to said patient or expanding hematopoietic stem cells by a method as defined herein and administering said expanded hematopoietic stem cells to said patient. In a further embodiment, the expanded cells are bone marrow cells from the organ donnor.

Regarding the method of treating a patient receiving an organ from a transplantation (ex. solid organ transplantation), reference can be made to Basak G W et al., Am J Transplant 2015 PMID: 25648262; Elahimehr R et al., Transplant Rev (Orlando) 2016, PMID: 27553809 and Marino Granados J M et al., Curr Opin Organ Transplant 2015, PMC4391059. Good review of preclinical and clinical studies.

The subject referred to herein is, for example, a bone marrow donor or an individual with or at risk for depleted or limited blood cell levels. Optionally, the subject is a bone marrow donor prior to bone marrow harvesting or a bone marrow donor after bone marrow harvesting. The subject is optionally a recipient of a bone marrow transplant. The methods described herein are particularly useful in subjects that have limited bone marrow reserve such as elderly subjects or subjects previously exposed to an immune depleting treatment or myeloablative treatment such as chemotherapy, e.g., for treating leukemia or lymphomas. The subject, optionally, has a decreased blood cell level or is at risk for developing a decreased blood cell level as compared to a control blood cell level. As used herein the term control blood cell level refers to an average level of blood cells in a subject prior to or in the substantial absence of an event that changes blood cell levels in the subject. An event that changes blood cell levels in a subject includes, for example, anemia, trauma, chemotherapy, bone marrow transplant and radiation therapy. For example, the subject has anemia or blood loss due to, for example, trauma.

As used herein, the term "hematopoietic stem cells" or "HSCs" is intended to mean cells having both pluripotency which allows them to differentiate into functional mature cells such as granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages), and the ability to regenerate while maintaining their pluripotency (self-renewal).

HSCs are part of the starting cell population. These cells are optionally obtained from the body or an organ of the body containing cells of hematopoietic origin. Such sources include un-fractionated bone marrow, umbilical cord, peripheral blood, liver, thymus, lymph and spleen. All of the aforementioned crude or un-fractionated blood products can be enriched for cells having hematopoietic stem cell characteristics in ways known to those of skill in the art.

As used herein, the term "starting cell population" is meant to identify a cell population comprising stem and/or progenitor cells, such as hematopoietic stem cells (HSCs) and/or hematopoietic progenitor cells, harvested from one of various sources mentioned above, as known in the art.

The starting cell population may first be subjected to enrichment or purification steps, including negative and/or positive selection of cells based on specific cellular markers in order to provide the starting cell population. Methods for isolating said starting cell population based on specific cellular markers may use fluorescent activated cell sorting (FACS) technology also called flow cytometry or solid or insoluble substrate to which is bound antibodies or ligands that interact with specific cell surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator.

The starting cell population can be enriched in CD34+ cells meaning a cell population selected based on the presence of the cell surface marker CD34+. CD34+ cells can be detected and counted using for example flow cytometry and fluorescently labeled anti-CD34 antibodies. Moreover, the starting cell population may be used directly for expansion or frozen and stored for use at a later point in time. Methods for enriching blood cell population in CD34+ cells include kits commercialized by Miltenyi Biotec (CD34+ direct isolation kit, Miltenyi Biotec, Bergisch, Gladbach, Germany) or by Baxter (Isolex 3000). The starting cell population may preferably contain at least 50% CD34+ cells, in some embodiments, more than 90% of CD34+ cells.

The compounds and further cell expanding agent as used herein may be added to expansion medium immobilized onto a substrate or support used for the culture.

The expansion of stem cells may be carried out in natural medium, a semi-synthetic medium or a synthetic medium in terms of composition, and may be a solid medium, a semisolid medium or a liquid medium in terms of shape, and any nutrient medium used for hematopoietic stem cell and/or hematopoietic progenitor cell culture, which is supplemented with the mixtures of cell expanding factors described above. Such medium typically comprises sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. Examples of such basal medium appropriate for a method of expanding HSCs include, without limitation, StemSpan™ Serum-Free Expansion Medium (SFEM) (StemCell Technologies, Vancouver, Canada), StemSpan™ H3000-Defined Medium (StemCell Technologies, Vancouver, Canada), CellGro™, SCGM (CellGenix, Freiburg Germany), StemPro™-34 SFM (Invitrogen), Dulbecco's Modified Eagles's Medium (DMEM), Ham's Nutrient Mixture H12 Mixture F12, McCoy's 5A medium, Eagles's Minimum Essential Medium (EMEM), aMEM medium (alpha Modified Eagles's Minimum Essential Medium), RPMI1640 medium, Isocove's Modified Dulbecco's Medium (IMDM), StemPro34 (Invitrogen), X-VIVO 10 (Cambrex), X-VIVO 15 (Cambrex) and Stemline II (Sigma-Aldrich).

The stem cells and/or progenitor cells can be cultured in a culture vessel generally used for animal cell culture such as a Petri dish, a flask, a plastic bag, a Teflon™ bag, optionally after preliminary coating with an extracellular matrix or a cell adhesion molecule. The material for such a coating may be collagens I to XIX, fibronectin, vitronectin, laminins 1 to 12, nitrogen, tenascin, thrombospondin, von Willebrand factor, osteoponin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The hematopoietic stem cells and/or hematopoietic progenitor cells may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82: 378, 1993; Astori G, Bone Marrow Transplant, 35: 1101, 2005). These publications and their content are incorporated herein by reference.

A starting cell population, in particular CD34+ enriched cells, may be grown under conditions for HSC expansion, for example between 2 and 21 days and/or until the indicated fold expansion and the characteristic cell populations are obtained. In one specific embodiment, the cells are grown ex vivo under conditions for HSC expansion not more than 21 days, 12 days, 10 days or 7 days.

Pharmaceutical compositions may comprise pharmaceutically acceptable carrier(s) and/or excipient(s). Many pharmaceutically acceptable carrier(s) and/or excipient(s) are known in the art. It will be understood by those in the art that a pharmaceutically acceptable carrier and/or excipient must be compatible with the other ingredients of the formulation and tolerated by a subject in need thereof. The proportion of each carrier and/or excipient can be determined by the skilled practitioner in accordance with standard pharmaceutical practice.

In order to ensure consistency of administration, in an embodiment of the present disclosure, the pharmaceutical composition is in the form of a discrete dosage units and may be prepared by any of the methods well known in the art of pharmacy. All methods include the step of bringing into association the active compound with a liquid carrier or solid carrier or both and then, if necessary, shaping the product into the desired formulation.

The compounds and expanded cells according to the disclosure may be formulated for parenteral administration, e.g. by injection, for example bolus injection or continuous infusion, and may be presented in unit dose form in ampoules, pre-filled syringes, small volume infusion or in multi-dose containers with/without an added preservative. The compositions are formulated in any conventional manner for use in the methods described herein. Administration is via any route known to be effective by one of ordinary skill. For example, the compositions is administered orally, parenterally (e.g., intravenously), by intramuscular injection, by intraperitoneal injection, transdermally, extracorporeally, intranasally or topically.

The following examples are provided to further illustrate details for the preparation and use of the compounds of the present disclosure. They are not intended to be limitations on the scope of the instant disclosure in any way, and they should not be so construed. Furthermore, the compounds described in the following examples are not to be construed as forming the only genus that is considered as the disclosure, and any combination of the compounds or their moieties may itself form a genus.

EXAMPLES

Scheme I: General synthesis of compounds of the invention wherein X = S

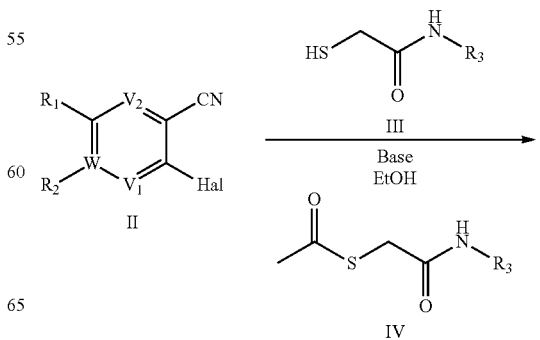

-continued

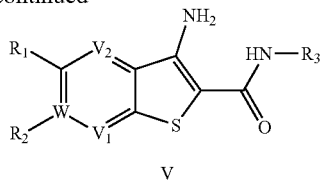

V

The compounds of the general formula V can be prepared by the condensation of compounds II, an ortho halo-pyridinecarbonitrile ($V_1$ or $V_2$ or W=N) or a 2-halobenzonitrile ($V_1$, $V_2$, W=C, $R_2$=H), with 2-mercaptoacetamide derivatives III or IV in the presence of a base in a solvent such as ethanol or DMF.

Scheme II: General synthesis of compounds of the invention wherein X = O

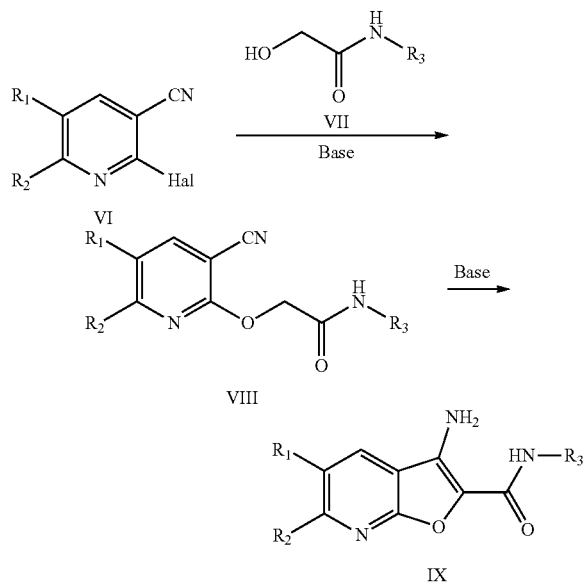

The compounds of the general formula IX can be prepared by the condensation of compounds VI, an ortho halo-pyridinecarbonitrile ($R_2$=H, $CH_3$ or linked to $R_1$ via $(CH_2)_{3-5}$ linkers), with 2-hydroxyacetamide derivatives VII in the presence of a base in a solvent such as ethanol followed by the cyclization of intermediate VIII in the presence of a stronger base.

Chemistry Experimental

Abbreviations or symbols used herein include: AcOH: acetic acid; dba: dibenzylidene acetone; DMF: N,N-dimethylformamide; DIPEA: diisopropylamine; DMSO: dimethylsulfoxide; dppf: 1,1'-bis(diphenylphosphino)ferrocene; EtOAc: ethyl acetate; EtOH: ethanol; MeOH: methanol; Hex: hexanes; MS: mass spectrometry; NMR: nuclear magnetic resonance; THF: tetrahydrofuran.

EXAMPLES

Other features of the present invention will become apparent from the following non-limiting examples which illustrate, by way of examples, the principle of the invention. As it is well known to a person skilled in the art, reactions are performed in an inert atmosphere (nitrogen or argon) where necessary to protect reaction components from air and moisture. Temperature are given in degrees Celsius (° C.).

The reactants used in the examples below may be obtained either as described herein, or if not described herein, are themselves either commercially available (described as A0 in table) or may be prepared from commercially available materials by methods known in the art. Flash chromatography is carried out on silica ($SiO_2$) using a Teledyne Isco Rf instrument. Mass spectra analyses are recorded using electrospray mass spectrometry. NMR are recorded on a 500 MHz Bruker or 400 MHz Varian instruments. Preparative HPLC is performed using an Agilent instrument with one the following conditions:

Column: Phenomenex-Kinetex C18, 21×100 mm, 5 μm
Mobile Phase: Solvent A: 5% MeOH, 95% Water+0.1% Formic acid, Solvent B: 95% MeOH, 5% Water+0.1% Formic acid
Flow: 20 mL/min, room temperature.
Collection wavelength=220 and 254 nm
Condition A:
Mobile Phase: From 0 to 3 min: isocratic 30% solvent B, followed by a 12 minutes gradient to 100% solvent B. Last 5 minutes 100% solvent B.
Condition B:
Mobile Phase: From 0 to 2 min: isocratic 30% solvent B, followed by an 8 minutes gradient to 100% solvent B. Last 2 minutes 100% solvent B.

Example 1: Preparation of Intermediate 1.4
(General Procedure A1)

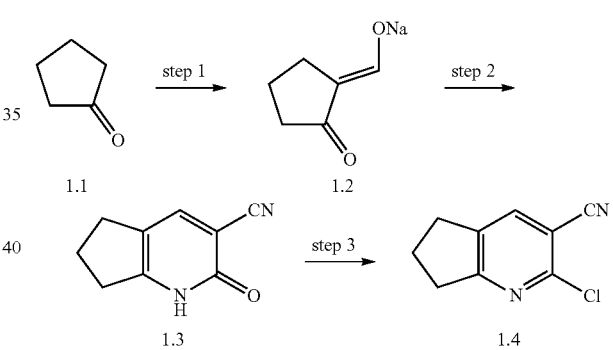

Step 1

EtOH (4.16 mL, 71.3 mmol) is added slowly to an ice-cold suspension of NaH (60% w/w; 2.85 g, 71.3 mmol) in ether (51 mL). Additional EtOH (8.5 ml) is added. A mixture of 1.1 (5.0 g, 59.4 mmol) and ethyl formate (5.02 mL, 62.4 mmol) is next added dropwise (55 min). Additional ether (10 mL) is added and the mixture is stirred at room temperature overnight. Ether (50 mL) is added and the mixture is filtered. The solid is washed with ether (25 mL) then dried under reduced pressure to give sodium salt 1.2; $^1$H NMR (500 MHz, DMSO-$d_6$) δ ppm 1.56 (quin, J=7.90 Hz, 2H), 1.87 (t, J=7.72 Hz, 2H), 2.24 (td, J=7.30, 0.95 Hz, 2H), 8.50, 8.87 (2s, 1H).

Step 2

A solution of 2-cyanoacetamide (4.58 g, 54.4 mmol) in water (27.5 mL) is added to 1.2 (7.30 g, 54.4 mmol) followed by a solution of piperidin-1-ium acetate (1.38 g, 9.53 mmol) (prepared by adding piperidine (0.81 g; 0.94 mL) to AcOH (0.57 g; 0.54 mL) in water (1.4 mL)) in water (1.4 mL). The mixture is heated at reflux for 2 h and let warm to room temperature (overnight). The pH is adjusted to 5 by addition of AcOH. The resulting suspension is cooled in an ice-bath and is filtered. The solid is washed with water and dried in the air to give pyridone 1.3; m/z=161.1 (MH⁺); ¹H NMR (500 MHz, DMSO-d₆) δ ppm 2.03 (quin, J=7.57 Hz, 2H), 2.64 (t, J=7.41 Hz, 2H), 2.80 (t, J=7.72 Hz, 2H), 8.00 (s, 1H), 12.62 (br. s., 1H).

Step 3

Pyridone 1.3 (1.0 g, 6.24 mmol) is added to a suspension of PCl₅ (0.390 g, 1.87 mmol) in POCl₃ (1.75 mL, 18.7 mmol) at room temperature. The mixture is heated at reflux for 2.5 h. The cooled mixture is poured into a mixture of ice and water (75 mL). The mixture is basified by addition of solid Na₂CO₃ (pH 7-8). The mixture is extracted with EtOAc (2×). The combined organic layers are washed with brine, dried (Na₂SO₄), filtered and concentrated under reduced pressure. The residue is purified by flash chromatography (10-40% EtOAc:Hex) to afford 2-chloropyridine 1.4; MS: m/z=179.3/181.1 (MH⁺); ¹H NMR (500 MHz, DMSO-d₆) δ ppm 2.11 (quin, J=7.65 Hz, 2H), 2.93 (t, J=7.57 Hz, 2H), 3.00 (t, J=7.72 Hz, 2H), 8.26 (s, 1H).

Example 2: Preparation of Intermediate 2.4 (Procedure A2)

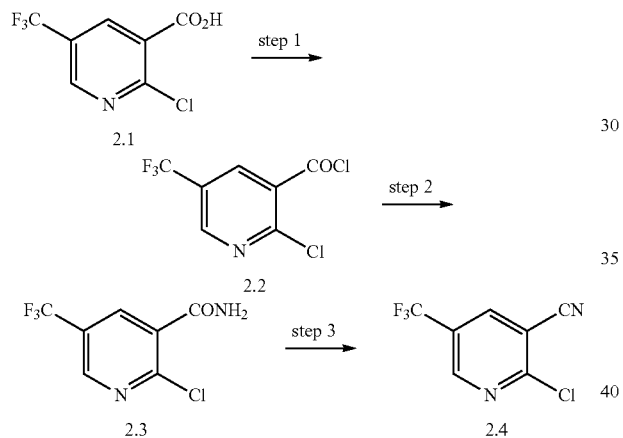

Step 1

DMF (10.30 μl, 0.133 mmol) is added to a suspension of acid 2.1 (0.6 g, 2.66 mmol), (COCl)₂ (0.466 mL, 5.32 mmol) in CH₂Cl₂ (10.6 mL) at room temperature. The mixture is stirred at room temperature for 6 h then is concentrated under reduced pressure to give acyl chloride 2.2.

Step 2

A solution of acyl chloride 2.2 (649 mg, 2.66 mmol) in dioxane (1.5 mL) is added to an ice-cold NH₄OH solution (1.60 mL, 23.9 mmol). The mixture is stirred at 0° C. for 45 min. The mixture is diluted with water (50 mL) and EtOAc is added (100 mL). The phases are separated. The organic layer is washed with water (2×), brine (25 mL), dried (Na₂SO₄), filtered and concentrated under reduced pressure to give amide 2.3; MS: m/z=225.2 (MH⁺); ¹H NMR (500 MHz, DMSO-d₆) δ ppm 7.95 (br. s., 1H), 8.17 (br. s., 1H), 8.39 (dd, J=2.52, 0.63 Hz, 1H), 8.91 (dd, J=2.52, 0.63 Hz, 1H).

Step 3

(CF₃CO)₂O (0.308 mL, 2.18 mmol) is added quickly to an ice-cold solution/suspension of amide 2.3 (445 mg, 1.98 mmol) in CH₂Cl₂ (14 mL). The mixture is stirred at 0° C. for 2 h. Saturated NaHCO₃ solution (15 mL) and CH₂Cl₂ are added and the mixture is stirred at room temperature for 5 min. The phases are separated. The organic layer is washed with brine, dried (Na₂SO₄), filtered and concentrated under reduced pressure. The residue is purified by flash chromatography (10-20% EtOAc:Hex) to yield chloropyridine 2.4; ¹H NMR (500 MHz, DMSO-d₆) δ ppm 9.09 (dd, J=2.52, 0.63 Hz, 1H), 9.16 (dd, J=2.52, 0.63 Hz, 1H).

Example 3: Preparation of Intermediate 3.5 (Procedure A3)

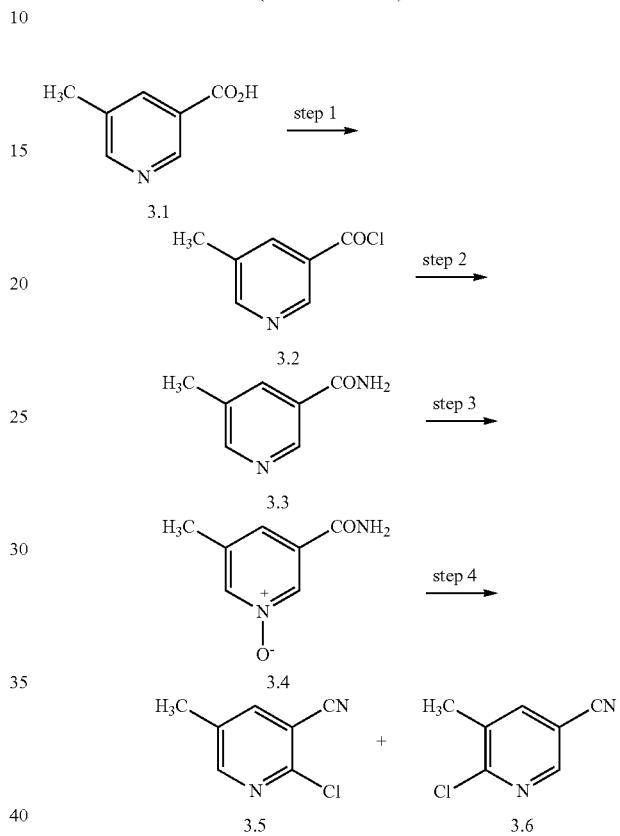

Step 1

(COCl)₂ (1.28 mL, 14.6 mmol) is added to a suspension of acid 3.1 (1.00 g, 7.29 mmol) in CH₂Cl₂ (29 mL) at room temperature. The mixture is stirred at room temperature for 2 h. The reaction mixture is concentrated under reduced pressure to give acyl chloride 3.2. The compound is used directly in the next reaction.

Step 2

Cold NH₄OH solution (4.86 mL, 72.9 mmol) is added quickly to an ice-cold suspension acyl chloride 3.2 (1.13 g, 7.29 mmol) in a mixture of dioxane (10 mL) and THF (10 mL). The mixture is stirred at 0° C. for 45 min. The crude mixture is diluted with water and extracted with EtOAc (3×). The aqueous layer is saturated with solid NaCl and re-extracted with EtOAc (2×). The combined organic layers are washed with brine, dried (Na₂SO₄), filtered and concentrated under reduced pressure to give amide 3.3; MS: m/z=137.2 (MH⁺); ¹H NMR (500 MHz, DMSO-d₆) δ ppm 2.34 (d, J=0.63 Hz, 3H), 7.53 (br. s., 1H), 7.98-8.04 (m, 1H), 8.08 (br. s., 1H), 8.54 (dd, J=2.21, 0.63 Hz, 1H), 8.82 (d, J=1.58 Hz, 1H).

Step 3

H₂O₂ (0.90 mL, 7.90 mmol) is added to a cold solution of amide 3.3 (538 mg, 3.95 mmol) in AcOH (4.9 mL). The mixture is stirred at room temperature for 30 min then is heated at 80° C. for 4 h. The mixture is cooled in an ice-bath and 20% Na$_2$SO$_3$ solution is added until there are no trace of peroxide left as determined with a KI-starch paper. 15 N NH$_4$OH is next added to basify the mixture. The resulting suspension is warmed to room temperature and is filtered, washing the solid with water. The solid is dried in the air to yield 3.4; MS: m/z=153.2 (MH$^+$); $^1$H NMR (500 MHz, DMSO-d$_6$) δ ppm 2.29 (d, J=0.63 Hz, 2H), 7.54-7.62 (m, 1H), 7.72 (br. s., 1H), 8.15 (br. s., 1H), 8.24-8.29 (m, 1H), 8.43 (s, 1H).

Step 4

Pyridine 1-oxide 3.4 (306 mg, 2.01 mmol) is added to cold (about 5° C.) POCl$_3$ (1.87 mL, 20.11 mmol). The resulting suspension is heated at 60° C. for 4 h and at 100° C. for 2.5 h. The cooled reaction mixture is poured into a mixture of ice and water (50 mL) and stirred vigorously. Solid Na$_2$CO$_3$ is added to obtain a pH of about 7. The mixture is extracted with EtOAc. The organic layer is washed with water and brine, then dried (Na$_2$SO$_4$) and concentrated under reduced pressure. The residue is purified by flash chromatography (10-30% EtOAc:Hex) to give first 6-chloro isomer 3.6 and, in second, 2-chloro isomer 3.5; 3.6: MS: m/z=153.1 (MH$^+$); $^1$H NMR (500 MHz, CDCl$_3$) δ ppm 2.46 (d, J=0.63 Hz, 3H), 7.82 (dq, J=2.21, 0.90 Hz, 1H), 8.54 (dd, J=2.21, 0.63 Hz, 1H); 3.5: MS: m/z=153.3/155.2 (MH$^+$); $^1$H NMR (500 MHz, CDCl$_3$) □ ppm 2.40 (t, J=0.60 Hz, 3H), 7.82 (dq, J=2.20, 0.60 Hz, 1H), 8.43 (dq, J=2.52, 0.90 Hz, 1H).

Example 4: Preparation of Intermediate 4.2 (Procedure A4)

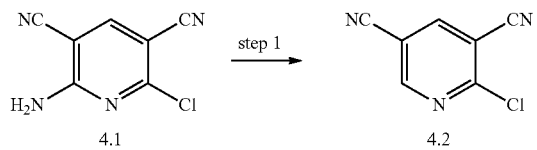 [SMILES: N#Cc1cc(C#N)c(Cl)nc1N ; N#Cc1cnc(Cl)c(C#N)c1]

Step 1

A solution of 4.1 (1.0 g, 5.60 mmol; M. Graffner-Nordberg, J. Med. Chem. 2001, 44, 2391) in DMF (11.2 mL) is added over 10 min to a solution of isoamyl nitrite (1.13 mL, 8.40 mmol) in DMF (4.7 mL) maintained at 70° C. After 1.5 h, the temperature is raised to 85° C. and maintained for 18 h. An additional amount of isoamyl nitrite (3.5 mL, 25.99 mmol) is added and the mixture is stirred at 85° C. for 4 h. The mixture is cooled to room temperature and is poured into water (200 mL). The mixture is extracted with EtOAc (3×). The combined organic layers are washed with water and brine, then dried (Na$_2$SO$_4$), filtered and concentrated under reduced pressure. The residue is purified by flash chromatography (0-50% EtOAc:Hex) to give 4.2; $^1$H NMR (500 MHz, CDCl$_3$) δ ppm 8.28 (d, J=2.21 Hz, 1H), 8.87 (d, J=2.21 Hz, 1H).

Example 5: Preparation of Intermediate 5.4 (Procedure A5)

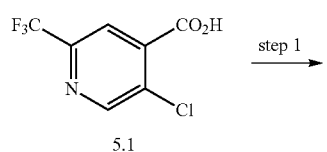

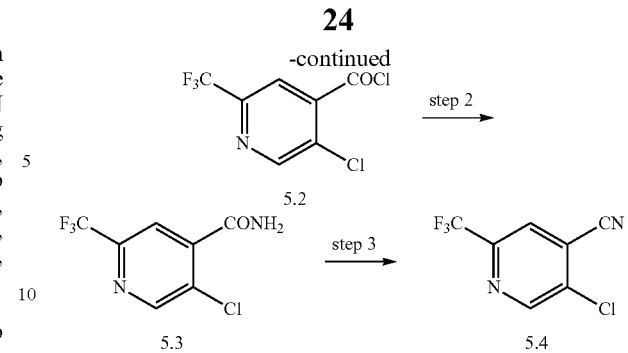

Step 1

(COCl)$_2$ (0.49 mL, 5.61 mmol) and DMF (8.7 μl, 0.112 mmol) are added to a suspension of 5.1 (506 mg, 2.24 mmol; Schlosser et al. Tetrahedron 2004, 60, 11869) in CH$_2$Cl$_2$ (11.2 mL) at room temperature. The mixture is stirred at room temperature for 3.5 h then is concentrated under reduced pressure to give 5.2; $^1$H NMR (500 MHz, CDCl$_3$) δ ppm 8.15 (s, 1H), 8.90 (s, 1H).

Step 2

A solution of 5.2 (547 mg, 2.24 mmol) in dioxane (1.5 mL) is added dropwise to an ice-cold solution of NH$_4$OH (15 M) (1.49 mL, 22.43 mmol) in dioxane (1.0 mL). The mixture is stirred at 0° C. for 1 h. The reaction mixture is poured into water (125 mL) and the mixture is extracted with EtOAc (2×). The combined organic layers are washed with water and brine, then dried (Na$_2$SO$_4$), filtered and concentrated under reduced pressure to give 5.3; MS: m/z: no molecular peak observed; $^1$H NMR (500 MHz, CDCl$_3$) δ ppm 6.11 (br. s., 1H), 6.42 (br. s., 1H), 8.09 (s, 1H), 8.80 (s, 1H).

Step 3

(CF$_3$CO)$_2$O (0.33 mL, 2.34 mmol) is added dropwise to an ice cold suspension/solution of 5.3 (405 mg, 1.80 mmol) in Et$_3$N (0.654 mL, 4.69 mmol) and CH$_2$Cl$_2$ (12 mL). The reaction mixture is stirred at 0° C. for 1.75 h. Saturated NaHCO$_3$ solution (5 mL) is added and the mixture is stirred vigorously for 5 min. The mixture is diluted with CH$_2$Cl$_2$ (60 mL) and saturated NaHCO$_3$ solution (20 mL). The phases are separated. The organic layer is washed with brine, dried (Na$_2$SO$_4$), filtered and concentrated under reduced pressure. The residue is purified by flash chromatography (0-50% EtOAc:Hex) to give 5.4; MS: m/z=no molecular peak observed; $^1$H NMR (500 MHz, CDCl$_3$) δ ppm 7.94 (s, 1H), 8.93 (s, 1H).

Example 6: Preparation of Intermediate 6.4 (Procedure A6)

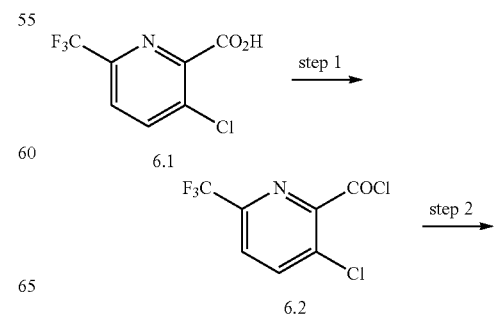

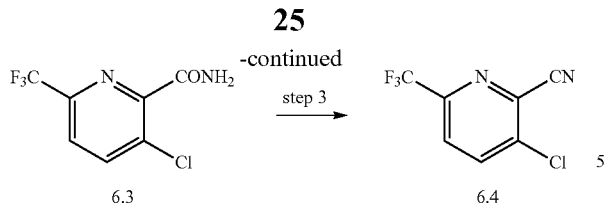

Step 1

(COCl)$_2$ (1.91 mL, 21.8 mmol) and DMF (0.012 mL, 0.156 mmol) are added to solution of 6.1 (1.35 g, 3.11 mmol; Schlosser et al. Tetrahedron 2004, 60, 11869) in CH$_2$Cl$_2$ (18 mL) at room temperature. The mixture is stirred at room temperature for 3 h then is concentrated under reduced pressure. The residue is kept on the high vacuum pump until stable weight to give 6.2; (500 MHz, CDCl$_3$) δ ppm 7.85 (d, J=8.2 Hz, 1H), 8.08 (dq, J=8.2, 0.06 Hz, 1H).

Step 2

A solution of 6.2 (759 mg, 3.11 mmol) in dioxane (3.1 mL) is added dropwise to an ice-cold solution of NH$_4$OH (15 M) (2.1 mL, 31.1 mmol). The mixture is stirred at 0° C. for 1 h. The mixture is poured into water (125 mL) and extracted with EtOAc (2×). The combined organic layers are washed with water, brine, dried (Na$_2$SO$_4$), filtered and concentrated under reduced pressure. The residue is purified by flash chromatography (10-50% EtOAc:Hex) to give 6.3; MS: m/z=225.1/227.3 (MH$^+$); $^1$H NMR (500 MHz, CDCl$_3$) δ ppm 5.68 (br. s., 1H), 7.55 (br. s., 1H), 7.77 (d, J=8.51 Hz, 1H), 8.05 (dd, J=8.51, 0.63 Hz, 1H).

Step 3

(CF$_3$CO)$_2$O (0.23 mL, 1.63 mmol) is added dropwise to an ice-cold solution/suspension of 6.3 (281 mg, 1.251 mmol) and Et$_3$N (0.45 mL, 3.25 mmol) in CH$_2$Cl$_2$ (8.3 mL). The mixture is stirred at 0° C. for 2 h. Saturated NaHCO$_3$ solution and CH$_2$Cl$_2$ are added and the mixture is stirred at room temperature for 5 min. The phases are separated. The organic layer is washed with brine, dried (Na$_2$SO$_4$), filtered and concentrated under reduced pressure. The residue is purified by flash chromatography (10-20% EtOAc:Hex) to give 6.4; $^1$H NMR (400 MHz, CDCl$_3$) δ ppm 7.87 (d, J=8.61 Hz, 1H), 8.10 (d, J=8.61 Hz, 1H).

Example 7: Preparation of Intermediate 7.2 (Procedure A7)

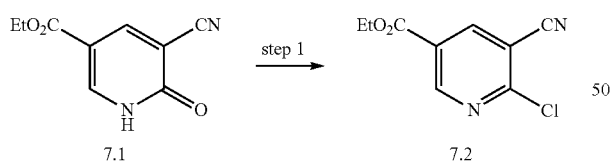

Step 1

A mixture of 7.1 (302 mg, 1.57 mmol; V. J. Colandrea, WO2005/058848), SOCl$_2$ (6.9 mL, 94 mmol) and DMF (0.68 mL, 8.79 mmol) is heated at reflux overnight (14 h). The cooled mixture is concentrated under reduced pressure. The residue is taken in EtOAc (70 mL) and the solution is washed with a 1:1 mixture of saturated NaHCO$_3$ solution and brine (3×), then dried (Na$_2$SO$_4$), filtered and concentrated under reduced pressure. The residue is purified by flash chromatography (0-20% EtOAc:Hex) to give 7.2; $^1$H NMR (400 MHz, CDCl$_3$) δ ppm 1.44 (t, J=7.04 Hz, 3H), 4.47 (q, J=7.04 Hz, 2H), 8.58 (d, J=2.35 Hz, 1H), 9.16 (d, J=2.35 Hz, 1H).

Example 8: Preparation of Intermediate 8.2 (Procedure A8)

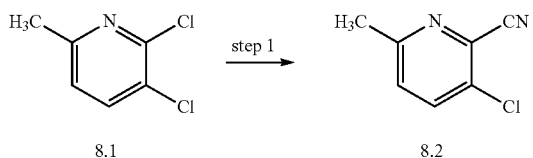

Step 1

A mixture of 8.1 (1.70 g, 10.51 mmol), Zn(CN)$_2$ (0.74 g, 6.30 mmol) and Zn (0.031 g, 0.47 mmol) in DMF (10.5 mL) is degassed (B. Van Wagenen, US2003/55085). PdCl$_2$(dppf)-CH$_2$C$_2$ adduct (0.189 g, 0.231 mmol) is added and the solution is again degassed then is heated at 125° C. for 5 h. The crude mixture is diluted with EtOAc (150 mL) and the mixture is filtered through diatomaceous earth (washing the cake with EtOAc (25 mL)). The filtrate is washed twice with a mixture of water and saturated NaHCO$_3$ solution (3/1) and with brine, then dried (Na$_2$SO$_4$), filtered and concentrated under reduced pressure. The residue is purified by flash chromatography (10-100% EtOAc:Hex) to give 8.2; MS: m/z=153.1/155.1 (MH$^+$); $^1$H NMR (400 MHz, CDCl$_3$) δ ppm 2.60 (s, 3H), 7.34 (d, J=8.22 Hz, 1H), 7.73 (d, J=8.61 Hz, 1H).

Example 9: Preparation of Intermediate 9.3 (General Procedure B1)

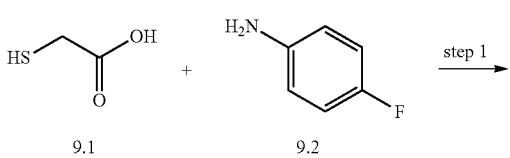

Step 1

A mixture of 2-mercaptoacetic acid 9.1 (0.679 mL, 9.77 mmol) and 4-fluoroaniline 9.2 (0.926 mL, 9.77 mmol) is heated at 130° C. for 5 h. The cooled mixture is taken in EtOAc and the solution is washed with 0.5N HCl solution, water and brine, then dried (Na$_2$SO$_4$), filtered and concentrated under reduced pressure. The residue is purified by flash chromatography (15-40% EtOAc:Hex) to give thiol 9.3; MS: m/z=186.1 (MH$^+$); $^1$H NMR (400 MHz, DMSO-d$_6$) δ ppm 2.95 (t, J=5.90 Hz, 1H), 3.28 (d, J=5.87 Hz, 2H), 7.15 (t, J=9.00 Hz, 2H), 7.59 (dd, J=9.39, 5.48 Hz, 2H), 10.13 (s, 1H).

Example 10: Preparation of Intermediate 10.4 (General Procedure B2)

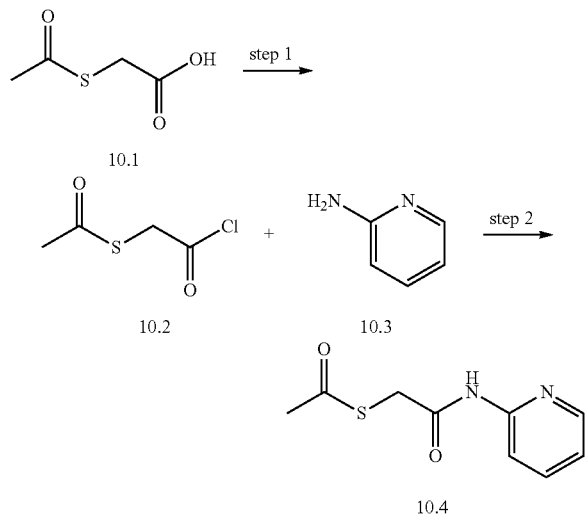

Step 1
DMF (0.042 mL, 0.54 mmol) is added to an ice-cold solution of acid 10.1 (1.45 g, 10.81 mmol) and (COCl)$_2$ (1.892 mL, 21.62 mmol) in CH$_2$Cl$_2$ (21.6 mL). The mixture is stirred overnight (16 h) at room temperature. The reaction mixture is concentrated under reduced pressure to give intermediate 10.2; $^1$H NMR (500 MHz, CDCl$_3$) δ ppm 2.44 (s, 3H), 4.18 (s, 2H).

Step 2
DIPEA (0.717 mL, 4.10 mmol) is added dropwise to an ice-cold solution of 10.2 (569 mg, 3.73 mmol) and 10.3 (369 mg, 3.92 mmol) in CH$_2$Cl$_2$ (19 mL). The mixture is stirred at 0° C. for 1 h and at room temperature for 1 h. The mixture is diluted with CH$_2$Cl$_2$ and the solution is washed with water and brine, then dried (Na$_2$SO$_4$), filtered and concentrated under reduced pressure. The residue is purified by flash chromatography (20-50% EtOAc:Hex) to give intermediate 10.4; MS: m/z=211.1 (MH$^+$); $^1$H NMR (400 MHz, DMSO-d$_6$) δ ppm 2.37 (s, 3H), 3.90 (s, 2H), 7.11 (dd, J=7.43, 5.09 Hz, 1H), 7.78 (ddd, J=8.20, 7.40, 1.96 Hz, 1H), 8.00 (d, J=8.22 Hz, 1H), 8.32 (ddd, J=4.70, 2.00, 1.00 Hz, 1H), 10.71 (s, 1H).

Example 11: Preparation of Intermediate 11.3 (General Procedure B3)

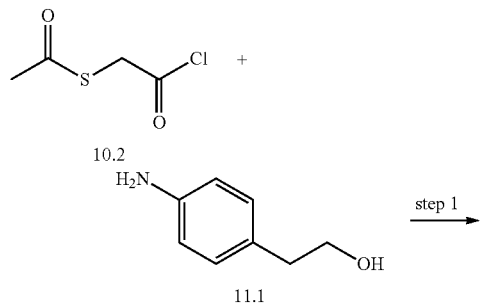

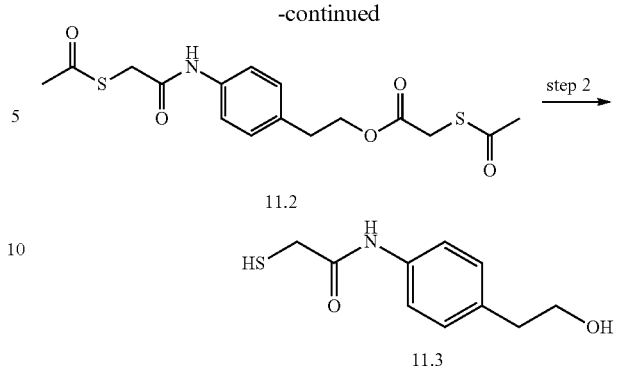

Step 1
A solution of 10.2 (0.848 g, 5.56 mmol) in CH$_2$Cl$_2$ (2.8 mL) is added dropwise to an ice-cold suspension of 11.1 (0.381 g, 2.78 mmol) in CH$_2$Cl$_2$ (8.4 mL) and pyridine (0.450 mL, 5.56 mmol). The mixture is stirred at 0° C. for 1.5 h. Water (5 mL) is added and the mixture is diluted with CH$_2$Cl$_2$. The mixture is washed with 1 N HCl solution, water, saturated NaHCO$_3$ solution, brine, then dried (Na$_2$SO$_4$), filtered and concentrated under reduced pressure. The residue is purified by flash chromatography (20-50% EtOAc:Hex) to afford 11.2; $^1$H NMR (500 MHz, CDCl$_3$) δ ppm 2.39 (s, 3H), 2.46 (s, 3H), 2.92 (t, J=7.09 Hz, 2H), 3.66 (s, 2H), 3.68 (s, 2H), 4.32 (t, J=6.94 Hz, 2H), 7.18 (d, J=8.51 Hz, 2H), 7.44 (d, J=8.51 Hz, 2H), 8.08 (br. s., 1H).

Step 2
K$_2$CO$_3$ (400 mg, 2.89 mmol) is added to a degassed solution of 11.2 (356 mg, 0.964 mmol) in MeOH (9.6 mL) at room temperature. The mixture is stirred at room temperature overnight (20 h). The mixture is concentrated under reduced pressure. Water (10 mL) is added and the mixture is acidified with 1N HCl solution (pH<2). The mixture is extracted with EtOAc (2×). The combined organic layers are washed with brine, dried (Na$_2$SO$_4$), filtered and concentrated under reduced pressure. The residue is purified by flash chromatography (40-100% EtOAc:Hex) to give 11.3; MS: m/z 212.1 (MH$^+$); $^1$H NMR (500 MHz, CDCl$_3$) δ ppm 1.39 (br. s., 1H), 2.03 (t, J=9.30 Hz, 1H), 2.86 (t, J=6.46 Hz, 2H), 3.41 (d, J=9.14 Hz, 2H), 3.82-3.90 (m, 2H), 7.23 (d, J=8.20 Hz, 2H), 7.50 (d, J=8.51 Hz, 2H), 8.46 (br. s., 1H).

Example 12: Preparation of Compound 1002 (General Procedure C1)

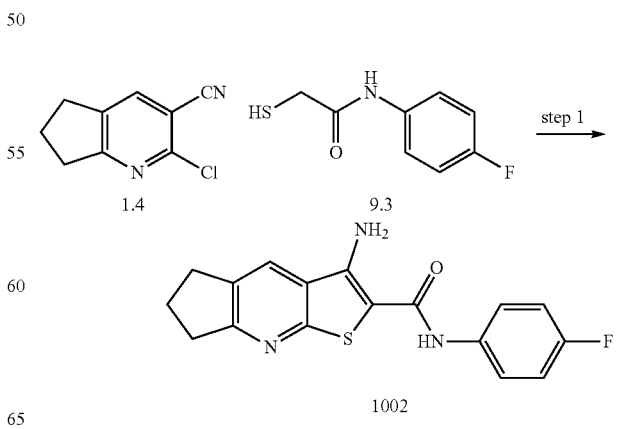

Step 1

A mixture of chloropyridine 1.4 (30 mg, 0.168 mmol), thiol 9.3 (34.2 mg, 0.185 mmol) and $K_2CO_3$ (58.0 mg, 0.420 mmol) in EtOH (1.7 mL) is heated at reflux for 4.5 h. The cooled mixture is diluted with EtOAc and the resulting solution is washed with water and brine, then dried ($Na_2SO_4$), filtered and concentrated under reduced pressure. The residue is recrystallized in a mixture of MeOH and $CHCl_3$ to give compound 1002; MS: m/z=328.1 (MH+); 1H NMR (400 MHz, DMSO-$d_6$) δ ppm 2.14 (quin, J=7.53 Hz, 2H), 3.00 (t, J=7.43 Hz, 2H), 3.02 (t, J=7.60 Hz, 2H), 7.15 (t, J=9.00 Hz, 2H), 7.29 (br. s, 2H), 7.69 (dd, J=9.00, 5.09 Hz, 2H), 8.28 (s, 1H), 9.42 (s, 1H).

Example 13: Preparation of Compound 1003
(General Procedure C2)

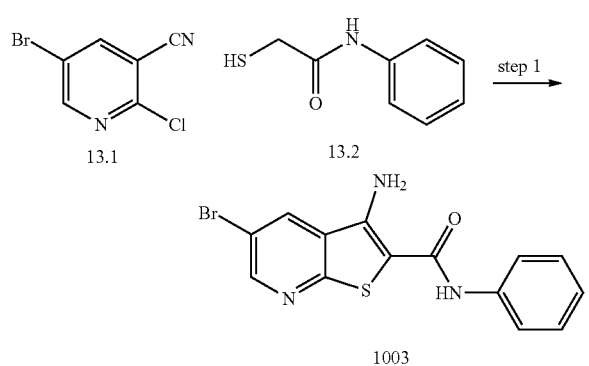

Step 1

A mixture of chloropyridine 13.1 (50 mg, 0.23 mmol), thiol 13.2 (42 mg, 0.25 mmol) and $K_2CO_3$ (79.5 mg, 0.575 mmol) in EtOH (2.3 mL) is heated at reflux for 5 h. The cooled mixture is diluted with water (15 mL). The resulting suspension is stirred for 15 min then is filtered and the solid is washed with a few drops of MeOH and hexanes to yield compound 1003; MS: m/z=347.9/349.7 (MH+); 1H NMR (500 MHz, DMSO-$d_6$) δ ppm 7.09 (t, J=7.41 Hz, 1H), 7.33 (t, J=7.88 Hz, 2H), 7.37 (s, 1H), 7.69 (d, J=7.57 Hz, 1H), 8.78 (d, J=2.21 Hz, 1H), 8.84 (d, J=2.21 Hz, 1H), 9.54 (s, 1H).

Example 14: Preparation of Compound 1009
(General Procedure C3)

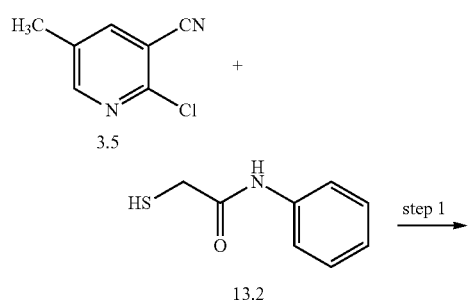

Step 1

A suspension of 3.5 (40 mg, 0.262 mmol), thiol 13.2 (48.2 mg, 0.288 mmol) and $K_2CO_3$ (91 mg, 0.655 mmol) in EtOH (2.6 mL) is heated at reflux for 5.5 h. The cooled mixture is diluted with EtOAc and is washed with water and brine (15 mL), dried ($Na_2SO_4$), filtered and concentrated under reduced pressure. The residue is purified by flash chromatography (30-50% EtOAc:Hex) to give compound 1009; MS: m/z=284.3 (MH+); 1H NMR (500 MHz, DMSO-$d_6$) δ ppm 2.43 (s, 3H), 7.07 (tt, J=7.37, 1.14 Hz, 1H), 7.24-7.37 (m, 4H), 7.69 (dd, J=8.67, 1.10 Hz, 2H), 8.32 (dd, J=2.05, 0.79 Hz, 1H), 8.54 (dd, J=2.21, 0.63 Hz, 1H), 9.40 (s, 1H).

Example 15: Preparation of Compound 1049
(General Procedure C4)

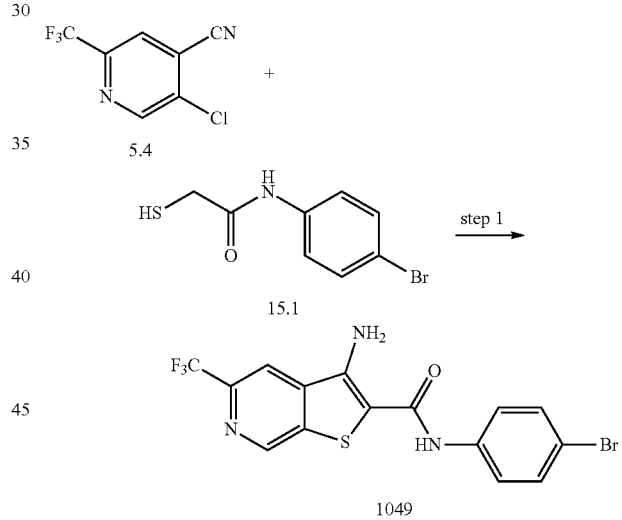

Step 1

A mixture of 5.4 (30 mg, 0.145 mmol), thiol 15.1 (41.1 mg, 0.167 mmol) and $K_2CO_3$ (50.2 mg, 0.363 mmol) in EtOH (1.4 mL) is stirred at room temperature for 10 min then heated at reflux for 3 h. The cooled mixture is diluted with EtOAc (60 mL) and the solution is washed with water and brine, then is dried ($Na_2SO_4$), filtered and concentrated under reduced pressure. The residue is purified by flash chromatography (10-50% EtOAc:Hex) then further purified by preparative HPLC (method A) to give compound 1049; MS: m/z=415.9/417.9 (MH+); 1H NMR (400 MHz, DMSO-de) δ ppm 7.48 (br. s., 2H), 7.53 (d, J=8.61 Hz, 2H), 7.70 (d, J=8.61 Hz, 2H), 8.73 (s, 1H), 9.39 (s, 1H), 9.92 (s, 1H).

Example 16: Preparation of Compound 1118 (General Procedure C5)

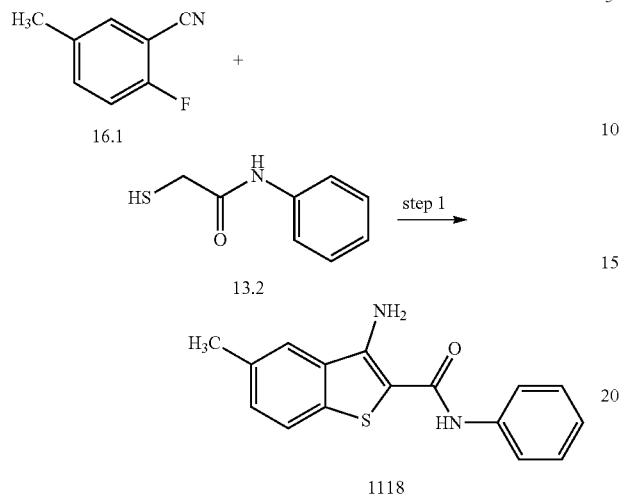

Step 1

A mixture of 16.1 (22 mg, 0.163 mmol), thiol 13.2 (28.6 mg, 0.171 mmol) and K$_2$CO$_3$ (56.2 mg, 0.407 mmol) in DMF (0.65 mL) is stirred at room temperature for 7 h. The mixture is diluted with EtOAc (50 mL) and the solution is washed with water and brine, then dried (Na$_2$SO$_4$), filtered and concentrated under reduced pressure. The residue is purified by flash chromatography (10-20% EtOAc:Hex) to give compound 1118; MS: m/z=283.1 (MH$^+$); $^1$H NMR (400 MHz, DMSO-d$_6$) δ ppm 2.44 (s, 3H), 7.06 (tt, J=7.40, 1.17 Hz, 1H), 7.19 (s, 2H), 7.31 (dd, J=8.61, 7.43 Hz, 1H), 7.35 (dd, J=8.22, 1.17 Hz, 1H), 7.69 (dd, J=8.80, 0.98 Hz, 2H), 7.76 (d, J=8.22 Hz, 1H), 7.91 (s, 1H), 9.29 (s, 1H).

Example 17: Preparation of Compound 1055 (General Procedure D)

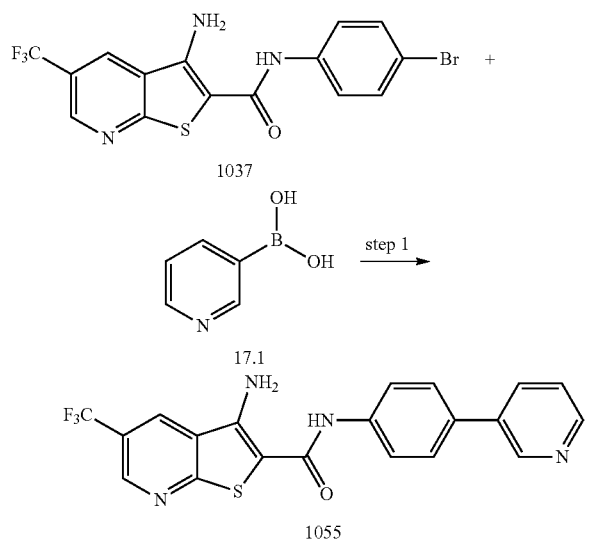

Step 1

PdCl$_2$(dppf)-CH$_2$C2 adduct (4.91 mg, 6.01 µmol) is added to a degassed (vacuum to argon 3×) partial solution of compound 1037 (50 mg, 0.120 mmol), boronic acid 17.1 (44.3 mg, 0.360 mmol) and K$_2$CO3 (49.8 mg, 0.360 mmol) in dioxane (1.15 mL) and water (0.287 mL) at room temperature. The mixture is degassed again and heated at 85° C. for 21 h. The cooled mixture is taken in EtOAc (150 mL) and water (30 mL) is added. The separated aqueous layer is extracted with CH$_2$Cl$_2$ (3×). The combined organic layers are washed with brine, dried (Na$_2$SO$_4$), filtered, and concentrated under reduced pressure. The solid is recrystallized in a 1:1 mixture of CHCl$_3$ and MeOH to give compound 1055; MS: m/z=415.0 (MH$^+$); $^1$H NMR (400 MHz, DMSO-d$_6$) δ ppm 7.39-7.47 (m, 2H), 7.50 (dd, J=8.02, 5.28 Hz, 1H), 7.57 (s, 2H), 7.78 (dt, J=7.04, 2.15 Hz, 1H), 7.99-8.12 (m, 2H), 8.58 (dd, J=4.70, 1.57 Hz, 1H), 8.87 (d, J=1.96 Hz, 1H), 9.04 (d, J=5.87 Hz, 1H), 9.72 (s, 1H).

Example 18: Preparation of Compound 1020

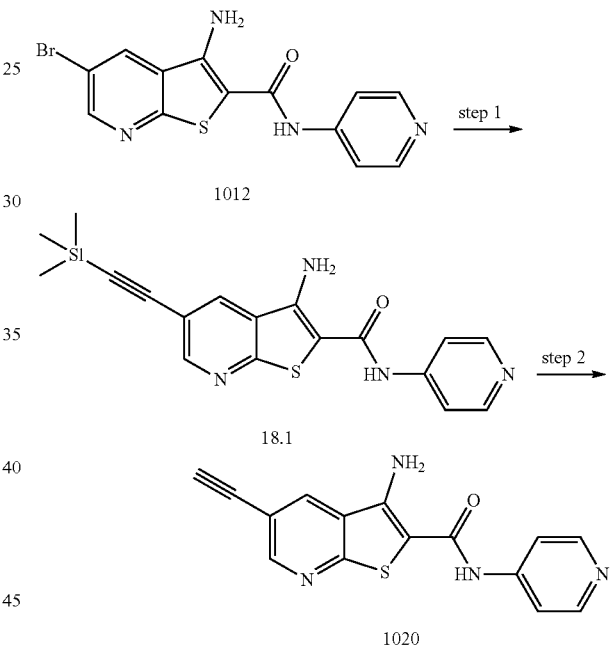

Step 1

To a mixture of compound 1012 (50 mg, 0.143 mmol), Pd(Ph$_3$P)$_4$ (16.5 mg, 0.014 mmol) and CuI (2.73 mg, 0.014 mmol) in THF (0.72 mL) and DMF (0.72 mL) are added sequentially DIPEA (0.41 mL, 2.86 mmol) and ethynyltrimethylsilane (101 µL, 0.716 mmol). The mixture is flushed with N$_2$ and heated at 110° C. for 2.5 h. The cooled mixture is diluted with water (15 mL) and extracted with EtOAc (3×). The aqueous layer is filtered and extracted with EtOAc. The combined organic layers are dried (Na$_2$SO$_4$), filtered and concentrated. The residue is purified by flash chromatography (0-100% EtOAc:Hex) to give 18.1; MS: m/z=367.2 (MH$^+$); $^1$H NMR (500 MHz, DMSO-d$_6$) δ ppm 0.22-0.32 (m, 9H), 7.55 (s, 2H), 7.77 (br. s., 2H), 8.71-8.77 (m, 2H), 9.84 (s, 1H).

Step 2

To a solution of 18.1 (50 mg, 0.136 mmol) in MeOH (2 mL) is added K$_2$CO$_3$ (37.7 mg, 0.273 mmol). The mixture is stirred at room temperature for 1 h then is concentrated under reduced pressure. The residue dissolved in 10% MeOH in CH$_2$Cl$_2$ (50 mL) is diluted with water. The resulting suspension is filtered and the solid dried in the air to give compound 1020; MS: m/z=295.2 (MH$^+$); $^1$H NMR (500 MHz, DMSO-d$_6$) δ ppm 4.50 (s, 1H), 7.57 (s, 2H), 7.76 (br. s., 1H), 8.44 (br. s., 1H), 8.69-8.80 (m, 1H), 9.84 (br. s., 1H).

Example 19: Preparation of Compound 1021

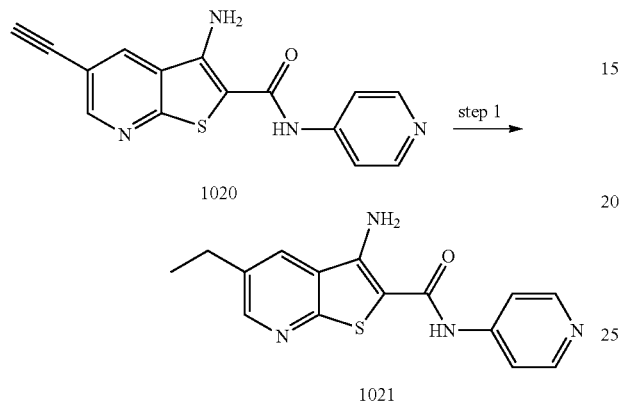

Step 1

A suspension of 1020 (20 mg, 0.068 mmol) and Pd—C 10% Degussa Type, 50% wet (7.2 mg) in MeOH (5 mL) is stirred under a hydrogen atmosphere for 45 min. The mixture is filtered through a 0.45 m filter unit, washed with MeOH (1 mL) and concentrated to afford compound 1021; MS: m/z=299.2 (MH$^+$); $^1$H NMR (500 MHz, DMSO-d$_6$) δ ppm 1.28 (t, J=7.57 Hz, 3H), 2.76 (q, J=7.57 Hz, 2H), 7.52 (s, 2H), 7.75-7.77 (m, 2H), 8.41-8.44 (m, 3H), 8.59 (d, J=1.89 Hz, 1H), 9.74 (s, 1H).

Example 20: Preparation of Compound 1090

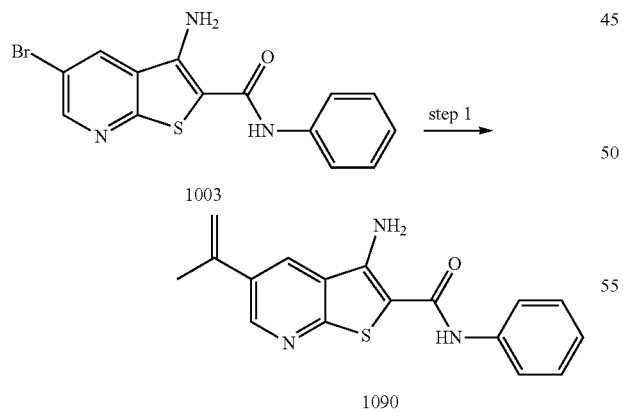

Step 1

A mixture of 1003 (25.7 mg, 0.074 mmol), prop-1-en-2-ylboronic acid (7.8 μL, 0.081 mmol) and K$_3$PO$_4$ (47.0 mg, 0.221 mmol) in DME-Water (2:1, 3 mL) is purged with a stream of N$_2$ for 5 min in a sealable vial. To this mixture is added Pd(Ph$_3$P)$_4$ (8.53 mg, 7.38 μmol), the vial is sealed and the mixture is heated at 90° C. under microwave radiations for 4 h. The cooled mixture is diluted with EtOAc and water. The aqueous phase is extracted with EtOAc (3×) and the combined organic layers are washed with brine, dried (Na$_2$SO$_4$), filtered and concentrated under reduced pressure. The residue is purified by preparative HPLC (method B) to afford 1090; MS: m/z=310.0 (MH$^+$); $^1$H NMR (400 MHz, DMSO-d$_6$) δ ppm 2.22 (s, 3H), 5.27 (s, 1H), 5.65 (s, 1H), 7.03-7.12 (m, 1H), 7.33 (t, J=7.83 Hz, 2H), 7.42 (s, 1H), 7.70 (d, J=7.43 Hz, 2H), 8.66 (d, J=2.35 Hz, 1H), 8.87 (d, J=2.35 Hz, 1H), 9.44 (s, 1H).

Example 21: Preparation of Compound 1103

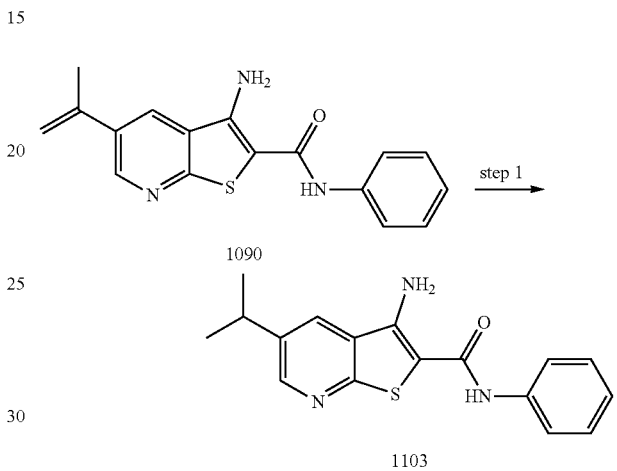

Step 1

A suspension of compound 1090 (57.3 mg, 0.185 mmol) and Pd—C 10% Degussa Type, 50% wet (20 mg) in MeOH (25 mL) is stirred under a hydrogen atmosphere for 18 h. The mixture is filtered on a pad of diatomaceous earth, washed with MeOH and concentrated under reduced pressure. The residue is purified by preparative HPLC (method B) to afford compound 1103; MS: m/z=312.1 (MH$^+$); $^1$H NMR (400 MHz, DMSO-d$_6$) δ ppm 1.31 (d, J=6.65 Hz, 6H), 3.09 (dt, J=13.89, 6.75 Hz, 1H), 7.03-7.11 (m, 1H), 7.28-7.40 (m, 4H), 7.70 (d, J=7.83 Hz, 2H), 8.44 (d, J=1.96 Hz, 1H), 8.60 (d, J=1.96 Hz, 1H), 9.40 (s, 1H).

Example 22: Preparation of Compound 1111

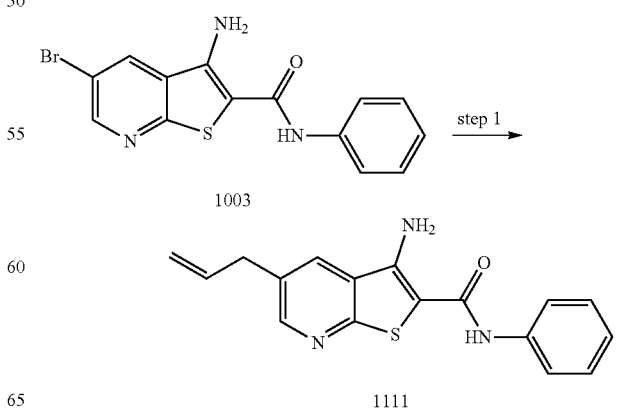

Step 1

A suspension of compound 1003 (56.9 mg, 0.163 mmol), allyltributylstannane (60.2 μL, 0.196 mmol) and K₂CO₃ (45.2 mg, 0.327 mmol) in toluene/water (5/1) (3.3 mL) is purged with a stream of N₂ for 10 min in a sealable vial. To this mixture is added Pd(Ph₃)₄ (4.72 mg, 4.09 μmol) and the vial is sealed and the mixture is heated at 105° C. for 23 h. The mixture is diluted with EtOAc and water, extracted twice with EtOAc. The combined organic layers are washed with brine, dried (Na₂SO₄), filtered and concentrated under reduced pressure. Since the reaction is not complete, the residue is resubmitted to the same reaction conditions (15 h heating). The crude material is purified by preparative HPLC (method B) then is filtered through a pad of silica gel (Hex/EtOAc (50/50) with 3% Et₃N). The filtrate is concentrated under reduced pressure to give compound 1111; MS: m/z=310.0 (MH⁺); ¹H NMR (400 MHz, DMSO-d₆) δ ppm 3.53 (d, J=6.65 Hz, 2H), 5.10-5.19 (m, 2H), 5.97-6.11 (m, 1H), 7.04-7.11 (m, 1H), 7.35 (d, J=6.65 Hz, 2H), 7.31 (d, J=8.22 Hz, 2H), 7.65-7.73 (m, 2H), 8.34 (d, J=1.96 Hz, 1H), 8.54 (d, J=1.96 Hz, 1H), 9.42 (s, 1H).

Example 23: Preparation of Compound 1112

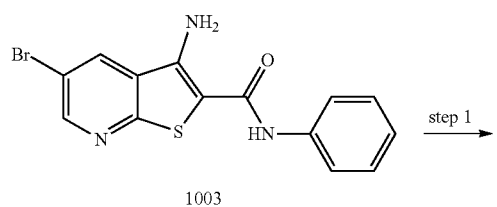

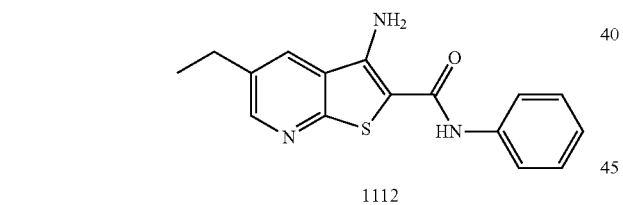

Step 1

A suspension of compound 1003 (29.8 mg, 0.086 mmol), triethylborane (34.2 μl, 0.034 mmol), K₃PO₄ (36.3 mg, 0.171 mmol) and di((3S,5S,7S)-adamantan-1-yl)(butyl)phosphine (1.53 mg, 4.28 μmol) in toluene/water (10/1) (1.57 mL) is purged with a stream of N₂ for 5 min in a sealable vial. To this mixture is added Pd₂(dba)₃ (0.980 mg, 1.070 μmol) and the vial is sealed and the mixture is heated at 105° C. for 17 h. The cooled mixture is diluted with EtOAc and water and extracted twice with EtOAc. The combined organic layers are washed with brine, dried (Na₂SO₄), filtered and concentrated under reduced pressure. The residue is purified by preparative HPLC (method B) to get compound 1112; MS: m/z=298.1 (MH⁺); ¹H NMR (400 MHz, DMSO-d₆) δ ppm 1.28 (t, J=7.43 Hz, 3H), 2.76 (q, J=7.70 Hz, 2H), 7.07 (t, J=7.24 Hz, 1H), 7.29-7.36 (m, 4H), 7.69 (d, J=8.22 Hz, 2H), 8.38 (s, 1H), 8.57 (s, 1H), 9.40 (s, 1H).

Example 24: Preparation of Compound 1134

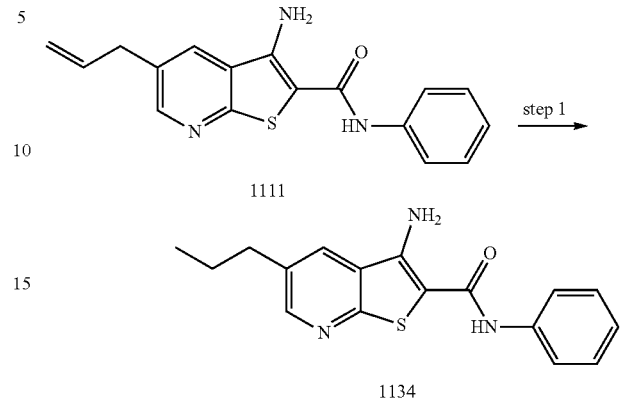

Step 1

A suspension of compound 1111 (30 mg, 0.097 mmol) and Pd—C 10% Degussa Type, 50% wet (10.3 mg) in MeOH (6 mL) is stirred under a hydrogen atmosphere for 18 h. The mixture is filtered (0.45 m filter unit) and concentrated under reduced pressure. The residue is purified by preparative HPLC (method B) to give compound 1134; MS: m/z=312.1 (MH⁺); ¹H NMR (400 MHz, DMSO-d₆) δ ppm 0.94 (t, J=7.43 Hz, 3H), 1.69 (dq, J=15.06, 7.24 Hz, 2H), 2.67-2.74 (m, 2H), 7.05-7.10 (m, 1H), 7.28-7.37 (m, 4H), 7.67-7.73 (m, 2H) 8.36 (d, J=1.96 Hz, 1H), 8.54 (d, J=1.96 Hz, 1H), 9.40 (s, 1H).

Example 25: Preparation of Compound 1153 (General Procedure E)

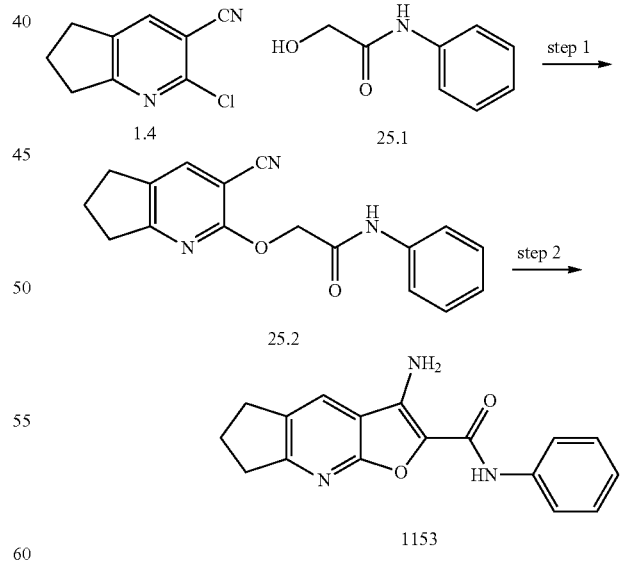

Step 1

A mixture of 1.4 (75 mg, 0.420 mmol), 25.1 (66.6 mg, 0.441 mmol; J. M. Hung et al., Eur. J. Med. Chem. 2014, 86, 420) and Na₂CO₃ (46.7 mg, 0.441 mmol) in EtOH (1.7 mL) is heated at reflux for 18 h. The cooled mixture is partitioned between EtOAc and water. The organic layer is washed with brine, dried (Na$_2$SO$_4$), filtered and concentrated under reduced pressure. The residue is purified by flash chromatography (10-30% EtOAc:Hex) to give 25.2; MS: m/z=294.2 (MH$^+$); $^1$H NMR (500 MHz, DMSO-d$_6$) δ ppm 2.06 (quin, J=7.65 Hz, 2H), 2.85 (td, J=7.49, 3.63 Hz, 4H), 5.06 (s, 2H), 7.06 (t, J=7.41 Hz, 1H), 7.31 (t, J=8.20 Hz, 2H), 7.56 (dd, J=8.67, 1.10 Hz, 2H), 8.09 (s, 1H), 10.16 (s, 1H).

Step 2 t-BuOK (45.4 mg, 0.405 mmol) is added to a solution of 25.2 (95 mg, 0.324 mmol) in THF (3.2 mL) at room temperature. The mixture is heated at reflux for 2 h. The mixture is taken in CH$_2$Cl$_2$ and the solution is washed with water and brine, dried (Na$_2$SO$_4$), filtered and concentrated under reduced pressure. The residue is purified by flash chromatography (2-15% EtOAc:CH$_2$Cl$_2$) to yield compound 1153; MS: m/z=294.2 (MH$^+$); $^1$H NMR (500 MHz, DMSO-d$_6$) δ ppm 2.14 (quin, J=7.57 Hz, 2H), 2.98 (t, J=7.25 Hz, 2H), 2.99 (t, J=7.57 Hz, 2H), 6.33 (s, 2H), 7.04 (tt, J=7.57, 0.95 Hz, 1H), 7.30 (dd, J=8.51, 7.57 Hz, 2H), 7.82 (dd, J=7.57, 1.26 Hz, 2H), 8.12 (s, 1H), 9.84 (s, 1H).

List of MS and NMR Data

Compound 1001; MS: m/z=310.3; $^1$H NMR (500 MHz, DMSO-d$_6$) ☐ ppm 2.14 (quin, J=7.49 Hz, 2H), 2.90-3.06 (m, 4H), 7.06 (tt, J=7.57, 0.95 Hz, 1H), 7.29 (s, 1H), 7.31 (dd, J=8.51, 7.57 Hz, 2H), 7.69 (dd, J=8.51, 1.30 Hz, 2H), 8.28 (s, 1H), 9.35 (s, 1H).

Compound 1002; Described in example 12

Compound 1003; MS: Described in example 13

Compound 1004; MS: m/z=304.1/306.1 (MH$^+$); $^1$H NMR (500 MHz, DMSO-d$_6$) δ ppm 7.09 (tt, J=7.25, 1.26 Hz, 1H), 7.33 (dd, J=8.51, 7.57 Hz, 1H), 7.37 (s, 2H), 7.69 (dd, J=8.83, 1.26 Hz, 1H), 8.65-8.76 (m, 1H), 9.54 (s, 1H).

Compound 1005; MS: m/z=298.2 (MH$^+$); $^1$H NMR (500 MHz, DMSO-d$_6$) δ ppm 2.36 (s, 3H) 2.55 (s, 3H) 7.06 (tt, J=7.33, 1.18 Hz, 1H) 7.27 (s, 2H) 7.31 (dd, J=8.51, 7.57 Hz, 2H) 7.68 (dd, J=8.83, 1.26 Hz, 2H) 8.22 (s, 1H) 9.34 (s, 1H)

Compound 1006; MS: m/z=311.3 (MH$^+$); $^1$H NMR (500 MHz, DMSO-d$_6$) δ ppm 2.14 (quin, J=7.49 Hz, 2H), 3.00 (t, J=7.25 Hz, 2H), 3.02 (t, J=7.25 Hz, 2H), 7.35 (dd, J=8.51, 4.73 Hz, 1H), 7.37 (s, 2H), 8.09 (ddd, J=8.35, 2.52, 1.42 Hz, 1H), 8.27 (dd, J=4.73, 1.58 Hz, 1H), 8.30 (s, 1H), 8.87 (d, J=2.52 Hz, 1H), 9.57 (s, 1H).

Compound 1007; MS: m/z=311.1 (MH$^+$); $^1$H NMR (400 MHz, DMSO-d$_6$) δ ppm 2.14 (quin, J=7.53 Hz, 2H), 3.00 (t, J=7.00 Hz, 2H), 3.01 (t, J=6.90 Hz, 2H), 7.12 (dd, J=7.04, 5.09 Hz, 1H), 7.36 (s, 2H), 7.80 (ddd, J=8.00, 6.70, 1.56 Hz, 1H), 8.05 (d, J=8.61 Hz, 1H), 8.31 (s, 1H), 8.35 (d, J=3.91 Hz, 1H), 9.49 (s, 1H).

Compound 1008; MS: m/z=338.2 (MH$^+$); $^1$H NMR (500 MHz, DMSO-d$_6$) δ ppm 7.10 (tt, J=7.41, 1.26 Hz, 1H), 7.34 (dd, J=8.51, 7.25 Hz, 2H), 7.52 (s, 2H), 7.70 (dd, J=8.67, 1.10 Hz, 2H), 8.97-9.10 (m, 2H), 9.61 (s, 1H).

Compound 1009; Described in example 14

Compound 1010; MS: m/z=288.3 (MH$^+$); $^1$H NMR (500 MHz, DMSO-d$_6$) δ ppm 7.09 (tt, J=7.41, 0.90 Hz, 1H), 7.33 (s, 2H), 7.33 (t, J=7.88 Hz, 2H), 7.69 (dd, J=8.67, 1.10 Hz, 2H), 8.46 (dd, J=9.62, 2.68 Hz, 1H), 8.74 (dd, J=2.84, 0.95 Hz, 1H), 9.51 (s, 1H).

Compound 1011; MS: m/z=305.2/307.1 (MH$^+$); $^1$H NMR (500 MHz, DMSO-d$_6$) δ ppm 7.54 (s, 2H), 7.75 (d, J=6.31 Hz, 1H), 8.44 (d, J=6.31 Hz, 1H), 8.74 (d, J=2.21 Hz, 1H), 8.75 (d, J=2.52 Hz, 1H) 9.86 (s, 1H).

Compound 1012; MS: m/z=349.1/351.1 (MH$^+$); $^1$H NMR (500 MHz, DMSO-d$_6$) δ ppm 7.54 (s, 2H), 7.75 (d, J=6.31 Hz, 2H), 8.43 (d, J=6.31 Hz, 2H), 8.80 (d, J=2.21 Hz, 1H), 8.88 (d, J=2.21 Hz, 1H), 9.86 (s, 1H).

Compound 1013; MS: m/z=339.2 (MH$^+$); $^1$H NMR (500 MHz, DMSO-d$_6$) δ ppm 7.69 (s, 2H), 7.76 (d, J=6.31 Hz, 2H), 8.45 (d, J=6.31 Hz, 2H), 9.06 (dd, J=2.21, 0.63 Hz, 1H), 9.09 (dd, J=2.21, 0.63 Hz, 1H), 9.93 (s, 1H).

Compound 1014; MS: m/z=311.3 (MH$^+$); $^1$H NMR (500 MHz, DMSO-d$_6$) δ ppm 2.14 (quin, J=7.57 Hz, 2H), 3.00 (t, J=6.90 Hz, 2H), 3.02 (t, J=7.60 Hz, 2H), 7.47 (s, 2H), 7.75 (d, J=6.31 Hz, 2H), 8.32 (s, 1H), 8.41 (d, J=6.31 Hz, 2H), 9.69 (s, 1H).

Compound 1015; MS: m/z=339.2 (MH$^+$); $^1$H NMR (500 MHz, DMSO-d$_6$) δ ppm 7.38 (dd, J=8.04, 4.89 Hz, 1H), 7.60 (br. s., 2H), 8.09 (d, J=8.20 Hz, 1H), 8.30 (d, J=4.10 Hz, 1H), 8.89 (br. s., 1H), 9.05 (s, 1H), 9.07 (s, 1H), 9.82 (s, 1H).

Compound 1016; MS: m/z=295.3 (MH$^+$); $^1$H NMR (500 MHz, DMSO-d$_6$) δ ppm 7.10 (tt, J=7.60, 0.90 Hz, 1H), 7.34 (dd, J=8.51, 7.25 Hz, 2H), 7.47 (s, 2H), 7.69 (dd, J=8.51, 1.26 Hz, 2H), 8.99-9.08 (m, 2H), 9.63 (s, 1H).

Compound 1017; MS: m/z=382.1 (MH$^+$); $^1$H NMR (500 MHz, DMSO-d$_6$) δ ppm 2.70 (t, J=7.09 Hz, 2H), 3.59 (td, J=7.17, 5.20 Hz, 2H), 4.62 (t, J=5.20 Hz, 1H), 7.17 (d, J=8.51 Hz, 2H), 7.50 (s, 2H), 7.58 (d, J=8.51 Hz, 2H), 9.04 (d, J=0.95 Hz, 2H), 9.55 (s, 1H).

Compound 1018; MS: m/z=382.2 (MH$^+$); $^1$H NMR (500 MHz, DMSO-d$_6$) δ ppm 3.28 (s, 3H), 4.37 (s, 2H), 7.28 (d, J=8.83 Hz, 2H), 7.53 (s, 2H), 7.68 (d, J=8.51 Hz, 2H), 8.94-9.08 (m, 2H), 9.63 (s, 1H).

Compound 1019; MS: m/z=368.2 (MH$^+$); $^1$H NMR (500 MHz, DMSO-d$_6$) δ ppm 4.47 (d, J=5.67 Hz, 2H), 5.11 (t, J=5.83 Hz, 1H), 7.28 (d, J=8.51 Hz, 2H), 7.51 (s, 2H), 7.64 (d, J=8.51 Hz, 2H), 8.97-9.08 (m, 2H), 9.58 (s, 1H).

Compound 1020; Described in example 18

Compound 1021; Described in example 19

Compound 1022 MS: m/z=339.2 (MH$^+$); $^1$H NMR (500 MHz, DMSO-d$_6$) δ ppm 7.15 (td, J=5.99, 0.95 Hz, 1H) 7.59 (s, 2H) 7.78-7.87 (m, 1H) 8.06 (d, J=8.20 Hz, 1H) 8.38 (dd, J=4.89, 1.10 Hz, 1H) 9.00-9.10 (m, 2H) 9.97 (s, 1H).

Compound 1023 MS: m/z=359.0 (MH$^+$); $^1$H NMR (400 MHz, DMSO-d$_6$) δ ppm 2.25 (d, J=1.17 Hz, 3H) 6.87 (s, 1H) 7.21 (br. s., 2H) 8.72 (s, 1H) 8.83 (d, J=1.57 Hz, 1H).

Compound 1024 MS: m/z=366.3 (MH$^+$); $^1$H NMR (500 MHz, DMSO-d$_6$) δ ppm 1.19 (t, J=7.57 Hz, 3H) 2.59 (q, J=7.57 Hz, 2H) 7.18 (m, J=8.83 Hz, 2H) 7.50 (s, 2H) 7.56-7.63 (m, 2H) 9.04 (s, 2H) 9.55 (s, 1H).

Compound 1025; MS: m/z=338.2 (MH$^+$); $^1$H NMR (500 MHz, DMSO-d$_6$) δ ppm 7.11 (tt, J=7.30, 1.30 Hz, 1H), 7.35 (dd, J=8.51, 7.25 Hz, 2H), 7.43 (s, 2H), 7.69 (dd, J=8.67, 1.10 Hz, 2H), 8.72 (br. d, J=0.60 Hz, 1H), 9.39 (s, 1H), 9.80 (s, 1H).

Compound 1026; MS: m/z=339.0 (MH$^+$); $^1$H NMR (400 MHz, DMSO-d$_6$) δ ppm 7.60 (s, 2H), 7.76 (d, J=6.26 Hz, 2H), 8.46 (d, J=6.26 Hz, 2H), 8.76 (s, 1H), 9.41 (s, 1H), 10.13 (br. s., 1H).

Compound 1027; MS: m/z=338 (MH$^+$); $^1$H NMR (400 MHz, DMSO-d$_6$) δ ppm 6.97 (s, 2H), 7.11 (tt, J=7.40, 1.20 Hz, 1H), 7.35 (dd, J=8.22, 7.43 Hz, 2H), 7.70 (dd, J=8.41, 0.98 Hz, 2H), 8.01 (d, J=8.61 Hz, 1H), 8.78 (d, J=8.61 Hz, 1H), 9.73 (s, 1H).

Compound 1028; MS: m/z=339.0 (MH$^+$); $^1$H NMR (400 MHz, DMSO-d$_6$) δ ppm 7.14 (s, 2H), 7.77 (d, J=6.26 Hz, 1H), 8.03 (d, J=8.22 Hz, 1H), 8.46 (d, J=6.26 Hz, 1H), 8.80 (d, J=8.22 Hz, 1H), 10.07 (br. s., 1H).

Compound 1029; MS: 394.9 m/z=(MH$^+$); $^1$H NMR (400 MHz, DMSO-d$_6$) δ ppm 7.59 (s, 2H) 7.80 (dd, J=8.80, 2.15 Hz, 1H) 8.05 (d, J=8.61 Hz, 1H) 8.56 (d, J=1.96 Hz, 1H) 9.06 (d, J=3.13 Hz, 1H) 9.30 (s, 1H) 9.89 (s, 1H).

Compound 1030; MS: 414.0 m/z=(MH$^+$); $^1$H NMR (400 MHz, DMSO-d$_6$) δ ppm 7.28-7.36 (m, 1H) 7.39-7.48 (m, 2H) 7.55 (br. s., 2H) 7.61-7.70 (m, 4H) 7.77-7.85 (m, 2H) 8.99-9.09 (m, 2H) 9.70 (s, 1H).

Compound 1031; MS: 444.0 m/z=(MH⁺); ¹H NMR (400 MHz, DMSO-d₆) δ ppm 5.10 (s, 2H) 6.75 (dt, J=8.22, 1.17 Hz, 1H) 7.19-7.28 (m, 1H) 7.29-7.37 (m, 2H) 7.37-7.44 (m, 2H) 7.44-7.51 (m, 3H) 7.54 (s, 2H) 9.05 (d, J=3.52 Hz, 2H) 9.58 (s, 1H).

Compound 1032; MS: 424.0 m/z=(MH⁺); ¹H NMR (400 MHz, DMSO-d₆) δ ppm 1.19 (t, J=7.04 Hz, 2H) 3.63 (s, 2H) 4.08 (q, J=7.04 Hz, 2H) 7.22 (m, J=8.61 Hz, 2H) 7.52 (s, 2H) 7.60-7.68 (m, 2H) 9.04 (s, 2H) 9.61 (s, 1H).

Compound 1033; MS: 444.0 m/z=(MH⁺); ¹H NMR (400 MHz, DMSO-d₆) δ ppm 3.76 (s, 3H) 7.10 (d, J=8.61 Hz, 1H) 7.31-7.36 (m, 1H) 7.40-7.45 (m, 2H) 7.50 (dd, J=8.41, 1.37 Hz, 4H) 7.64-7.70 (m, 2H) 9.03 (s, 2H) 9.57 (s, 1H).

Compound 1034; MS: m/z=337.0 (MH⁺); ¹H NMR (400 MHz, DMSO-d₆) δ ppm 7.08 (tt, J=7.40, 1.20 Hz, 1H), 7.33 (t, J=7.83 Hz, 2H), 7.42 (s, 2H), 7.69 (dd, J=8.61, 1.17 Hz, 2H), 7.79 (dd, J=8.61, 1.57 Hz, 1H), 8.15 (d, J=8.61 Hz, 1H), 8.62 (s, 1H), 9.52 (s, 1H).

Compound 1035; MS: m/z=338.0 (MH⁺); ¹H NMR (400 MHz, DMSO-d₆) δ ppm 7.61 (s, 2H), 7.78 (d, J=6.65 Hz, 2H), 7.82 (dd, J=8.61, 1.57 Hz, 1H), 8.17 (d, J=8.61 Hz, 1H), 8.45 (d, J=5.09 Hz, 2H), 8.67 (s, 1H), 9.91 (br. s., 1H).

Compound 1036; MS: m/z=415.9/417.9 (MH⁺); ¹H NMR (400 MHz, DMSO-d₆) δ ppm 7.26-7.34 (m, 2H) 7.60 (s, 2H) 7.70 (dt, J=7.43, 1.96 Hz, 1H) 8.06 (t, J=1.76 Hz, 1H) 9.02-9.09 (m, 2H) 9.75 (s, 1H).

Compound 1037; MS: m/z=415.9/417.9 (MH⁺); ¹H NMR (400 MHz, DMSO-d₆) δ ppm 7.50 (d, J=8.61 Hz, 2H) 7.55 (br. s., 2H) 7.63-7.75 (m, 2H) 9.03 (d, J=4.70 Hz, 2H) 9.71 (s, 1H).

Compound 1038; MS: m/z=377.0 (MH⁺); ¹H NMR (400 MHz, DMSO-d₆) δ ppm 3.98 (s, 2H) 7.30 (d, J=8.61 Hz, 2H) 7.53 (s, 2H) 7.67-7.74 (m, 2H) 8.98-9.06 (m, 2H) 9.67 (s, 1H).

Compound 1039; MS: m/z=391.0 (MH⁺); ¹H NMR (400 MHz, DMSO-d₆) δ ppm 7.51 (s, 2H) 7.67-7.80 (m, 2H) 7.82 (d, J=6.65 Hz, 1H) 8.07 (d, J=8.22 Hz, 1H) 8.53 (d, J=5.87 Hz, 1H) 9.04-9.10 (m, 2H) 9.36 (d, J=0.78 Hz, 1H) 10.00 (s, 1H).

Compound 1040; MS: m/z=389.0 (MH⁺); ¹H NMR (400 MHz, DMSO-d₆) δ ppm 7.48 (s, 2H) 7.55 (dd, J=8.41, 4.11 Hz, 1H) 7.62 (dd, J=7.43, 1.17 Hz, 1H) 7.78 (dd, J=8.22, 7.43 Hz, 1H) 7.95 (d, J=8.61 Hz, 1H) 8.24-8.35 (m, 1H) 8.92 (dd, J=4.11, 1.76 Hz, 1H) 9.05 (s, 2H) 10.00 (s, 1H).

Compound 1041; MS: m/z=389.0 (MH⁺); ¹H NMR (400 MHz, DMSO-d₆) δ ppm 7.49 (dd, J=8.22, 4.30 Hz, 1H) 7.62 (s, 2H) 7.97 (d, J=9.00 Hz, 1H) 8.04 (dd, J=9.00, 2.35 Hz, 1H) 8.24-8.32 (m, 1H) 8.40 (d, J=2.35 Hz, 1H) 8.79 (dd, J=4.11, 1.76 Hz, 1H) 9.01-9.11 (m, 2H) 9.94 (s, 1H).

Compound 1042; MS: m/z=389.0 (MH⁺); ¹H NMR (400 MHz, DMSO-d₆) δ ppm 7.58 (td, J=7.53, 1.37 Hz, 1H) 7.66 (td, J=7.53, 1.37 Hz, 3H) 7.89-8.01 (m, 2H) 8.70 (d, J=2.35 Hz, 1H) 9.01-9.11 (m, 2H) 9.14 (d, J=2.74 Hz, 1H) 10.07 (s, 1H).

Compound 1043; MS: m/z=389.0 (MH⁺); ¹H NMR (400 MHz, DMSO-d₆) δ ppm 7.40-7.69 (m, 3H) 7.72-7.88 (m, 2H) 7.98 (br. s., 1H) 8.13 (s, 1H) 8.82 (br. s., 1H) 9.04 (br. s., 2H) 10.14 (br. s., 1H).

Compound 1044; MS: m/z=342.0 (MH⁺); ¹H NMR (400 MHz, DMSO-d₆) δ ppm 1.39 (t, J=7.04 Hz, 3H), 4.41 (q, J=7.04 Hz, 2H), 7.09 (tt, J=7.40, 1.20 Hz, 1H), 7.33 (dd, J=8.61, 7.43 Hz, 2H), 7.59 (s, 2H), 7.69 (dd, J=8.80, 0.98 Hz, 2H), 9.14 (d, J=1.96 Hz, 1H), 9.16 (d, J=1.96 Hz, 1H), 9.56 (s, 1H).

Compound 1045; MS: m/z=372.0/374.0 (MH⁺); ¹H NMR (400 MHz, DMSO-d₆) δ ppm 7.39 (d, J=9.00 Hz, 2H), 7.56 (s, 1H), 7.75 (d, J=9.00 Hz, 2H), 9.00-9.08 (m, 2H), 9.74 (s, 1H).

Compound 1046; MS: m/z=396.1 (MH⁺); ¹H NMR (400 MHz, DMSO-d₆) δ ppm 2.78 (t, J=6.85 Hz, 2H), 3.25 (s, 3H), 3.53 (t, J=6.85 Hz, 2H), 7.19 (d, J=8.22 Hz, 2H), 7.50 (s, 2H), 7.59 (d, J=8.22 Hz, 2H), 9.04 (s, 2H), 9.56 (s, 1H).

Compound 1047; MS: m/z=352.1 (MH⁺); ¹H NMR (400 MHz, DMSO-d₆) δ ppm 2.28 (s, 3H), 7.14 (d, J=8.61 Hz, 2H), 7.50 (s, 2H), 7.57 (d, J=8.22 Hz, 2H), 9.03 (s, 2H), 9.54 (s, 1H).

Compound 1048; MS: m/z=368.0 (MH⁺); ¹H NMR (400 MHz, DMSO-d₆) δ ppm 3.75 (s, 3H), 6.91 (d, J=9.00 Hz, 2H), 7.47 (s, 2H), 7.58 (d, J=9.00 Hz, 2H), 9.03 (s, 2H), 9.51 (s, 1H).

Compound 1049; Described in example 15

Compound 1050; MS: m/z=413.9/415.9 (M-H)⁻; ¹H NMR (400 MHz, DMSO-d₆) δ ppm 7.02 (br. s., 2H), 7.53 (d, J=9.00 Hz, 2H), 7.71 (d, J=8.61 Hz, 2H), 8.01 (d, J=8.61 Hz, 1H), 8.78 (d, J=8.61 Hz, 1H), 9.85 (s, 1H).

Compound 1051; MS: m/z=372.0/374.0 (MH⁺); ¹H NMR (400 MHz, DMSO-d₆) δ ppm 7.41 (d, J=9.00 Hz, 2H), 7.47 (s, 2H), 7.75 (d, J=9.00 Hz, 2H), 8.73 (s, 1H), 9.39 (s, 1H), 9.93 (s, 1H).

Compound 1052; MS: m/z=350.0 (M-H)⁻; ¹H NMR (400 MHz, DMSO-d₆) δ ppm 2.28 (s, 3H), 7.15 (d, J=8.22 Hz, 2H), 7.41 (s, 2H), 7.57 (d, J=8.61 Hz, 2H), 8.71 (s, 1H), 9.38 (s, 1H), 9.73 (s, 1H).

Compound 1053; MS: m/z=369.9/371.9 (M-H)⁻; ¹H NMR (400 MHz, DMSO-d₆) δ ppm 7.01 (s, 2H), 7.41 (d, J=9.00 Hz, 2H), 7.76 (d, J=9.00 Hz, 2H), 8.01 (d, J=8.61 Hz, 1H), 8.78 (d, J=8.61 Hz, 1H), 9.86 (s, 1H).

Compound 1054; MS: m/z=350.0 (M-H)⁻; ¹H NMR (400 MHz, DMSO-d₆) δ ppm 2.29 (s, 3H), 6.94 (s, 2H), 7.15 (d, J=8.61 Hz, 2H), 7.58 (d, J=8.61 Hz, 2H), 8.00 (d, J=8.22 Hz, 1H), 8.77 (d, J=8.61 Hz, 1H), 9.66 (s, 1H).

Compound 1055; Described in example 17

Compound 1056; MS: m/z=415.0 (MH⁺); ¹H NMR (400 MHz, DMSO-d₆) δ ppm 7.40-7.54 (m, 2H) 7.58 (s, 2H) 7.63-7.71 (m, 2H) 7.82 (dt, J=7.83, 1.76 Hz, 1H) 8.16 (t, J=1.76 Hz, 1H) 8.61-8.70 (m, 2H) 9.00-9.09 (m, 2H) 9.75 (s, 1H).

Compound 1057; MS: m/z=415.0 (MH⁺); ¹H NMR (400 MHz, DMSO-d₆) δ ppm 7.46 (dd, J=7.83, 4.70 Hz, 1H) 7.56 (br. s., 2H) 7.72 (m, J=9.00 Hz, 2H) 7.85 (m, J=8.61 Hz, 2H) 8.07 (d, J=7.83 Hz, 1H) 8.53 (d, J=3.52 Hz, 1H) 8.90 (d, J=1.96 Hz, 1H) 9.04 (d, J=5.09 Hz, 2H) 9.74 (s, 1H).

Compound 1058; MS: m/z=415.0 (MH⁺); ¹H NMR (400 MHz, DMSO-d₆) δ ppm 7.58 (s, 2H) 7.66-7.74 (m, 2H) 7.77-7.85 (m, 2H) 7.85-7.93 (m, 2H) 8.56-8.62 (m, 2H) 9.00-9.09 (m, 2H) 9.79 (s, 1H).

Compound 1059; MS: m/z=414.1 (MH⁺); ¹H NMR (400 MHz, DMSO-d₆) δ ppm 7.34-7.39 (m, 2H) 7.39-7.45 (m, 1H) 7.45-7.50 (m, 2H) 7.56 (s, 2H) 7.62-7.66 (m, 2H) 7.72 (dt, J=7.53, 1.71 Hz, 1H) 8.04 (t, J=1.96 Hz, 1H) 9.02-9.06 (m, 2H) 9.68 (s, 1H).

Compound 1060; MS: m/z=356.0 (MH⁺); ¹H NMR (400 MHz, DMSO-d₆) δ ppm 7.10-7.21 (m, 2H) 7.50 (br. s., 2H) 7.63-7.73 (m, 2H) 9.02 (s, 2H) 9.66 (br. s., 1H).

Compound 1061; MS: m/z=406.0 (MH⁺); ¹H NMR (400 MHz, DMSO-d₆) δ ppm 7.62 (s, 2H) 7.68 (d, J=8.61 Hz, 2H) 7.94 (d, J=8.61 Hz, 2H) 9.00-9.11 (m, 2H) 9.92 (s, 1H).

Compound 1062; MS: m/z=362.0/364.0 (MH⁺); ¹H NMR (400 MHz, DMSO-d₆) δ ppm 2.43 (s, 3H), 7.36 (s, 2H), 7.50 (d, J=8.61 Hz, 2H), 7.69 (d, J=9.00 Hz, 2H), 8.33 (dd, J=1.96, 0.78 Hz, 1H), 8.54 (d, J=1.56 Hz, 1H), 9.53 (s, 1H).

Compound 1063; MS: m/z=285.1 (MH⁺); ¹H NMR (400 MHz, DMSO-d₆) δ ppm 2.43 (s, 3H), 7.50 (s, 2H), 7.75 (d, J=6.65 Hz, 2H), 8.37 (dd, J=1.96, 0.78 Hz, 1H), 8.42 (d, J=6.26 Hz, 2H), 8.56 (d, J=1.96 Hz, 1H), 9.74 (s, 1H).

Compound 1064; MS: m/z=412.9/414.9 (M-H)⁻; ¹H NMR (400 MHz, DMSO-d₆) δ ppm 7.46 (s, 2H), 7.51 (d, J=9.00 Hz, 2H), 7.69 (d, J=9.00 Hz, 2H), 7.80 (dd, J=8.61, 1.57 Hz, 1H), 8.16 (d, J=8.61 Hz, 1H), 8.63 (s, 1H), 9.65 (s, 1H).

Compound 1065; MS: m/z=351.1 (MH⁺); ¹H NMR (400 MHz, DMSO-d₆) δ ppm 2.28 (s, 3H), 7.13 (d, J=8.22 Hz, 2H), 7.39 (s, 2H), 7.56 (d, J=8.61 Hz, 2H), 7.79 (dd, J=8.61, 1.57 Hz, 1H), 8.15 (d, J=8.61 Hz, 1H), 8.61 (s, 1H), 9.44 (s, 1H).

Compound 1066; MS: m/z=371.0 (MH⁺); ¹H NMR (400 MHz, DMSO-d₆) δ ppm 7.38 (d, J=8.61 Hz, 2H), 7.46 (s, 2H), 7.74 (d, J=8.61 Hz, 2H), 7.80 (dd, J=8.61, 1.57 Hz, 1H), 8.16 (d, J=8.22 Hz, 1H), 8.63 (s, 1H), 9.65 (s, 1H).

Compound 1067; MS: m/z=338.0 (MH⁺); ¹H NMR (400 MHz, DMSO-d₆) δ ppm 7.37 (dd, J=8.22, 4.70 Hz, 1H), 7.50 (s, 2H), 7.81 (dd, J=8.41, 1.37 Hz, 1H), 8.09 (ddd, J=8.31, 2.45, 1.37 Hz, 1H), 8.17 (d, J=8.61 Hz, 1H), 8.29 (br. d, J=3.90 Hz, 1H), 8.65 (s, 1H), 8.88 (d, J=1.96 Hz, 1H), 9.73 (s, 1H).

Compound 1068; MS: m/z=318.1/320.0 (MH⁺); ¹H NMR (400 MHz, DMSO-d₆) δ ppm 2.43 (s, 3H), 7.36 (s, 2H), 7.37 (d, J=9.00 Hz, 2H), 7.74 (d, J=8.61 Hz, 2H), 8.33 (dd, J=2.15, 0.98 Hz, 1H), 8.54 (d, J=2.35, 0.78 Hz, 1H), 9.53 (s, 1H).

Compound 1069; MS: m/z=298.1 (MH⁺); ¹H NMR (400 MHz, DMSO-d₆) δ ppm 2.27 (s, 3H), 2.43 (s, 3H), 7.12 (d, J=8.22 Hz, 2H), 7.28 (s, 2H), 7.56 (d, J=8.22 Hz, 1H), 8.31 (dd, J=1.96, 0.78 Hz, 1H), 8.53 (d, J=1.57 Hz, 1H), 9.33 (s, 1H).

Compound 1070; MS: m/z=353.0 (MH⁺); ¹H NMR (400 MHz, DMSO-d₆) δ ppm 2.4 (s, 3H), 7.23 (d, J=8.22 Hz, 1H), 7.57 (s, 2H), 7.96 (dd, J=8.41, 2.54 Hz, 1H), 8.74 (d, J=2.35 Hz, 1H), 9.02-9.09 (m, 2H), 9.74 (s, 1H).

Compound 1071; MS: m/z=369.0 (MH⁺); ¹H NMR (400 MHz, DMSO-d₆) δ ppm 3.84 (s, 3H), 6.83 (dd, J=8.61, 0.78 Hz, 1H), 7.53 (s, 2H), 7.96 (dd, J=8.61, 2.74 Hz, 1H), 8.39-8.45 (m, 1H), 9.00-9.08 (m, 2H), 9.68 (s, 1H).

Compound 1072; MS: m/z=284.1 (MH⁺); ¹H NMR (400 MHz, DMSO-d₆) δ ppm 2.63 (s, 3H), 6.80 (s, 2H), 7.08 (tt, J=7.40, 1.20 Hz, 1H), 7.33 (d, J=8.61, 7.43 Hz, 2H), 7.42 (d, J=8.61 Hz, 1H), 7.70 (dd, J=8.61, 1.17 Hz, 1H), 8.30 (d, J=8.22 Hz, 1H), 9.50 (s, 1H).

Compound 1073; MS: m/z=318.1/320.1 (MH⁺); ¹H NMR (400 MHz, DMSO-d₆) δ ppm 2.63 (s, 3H), 6.85 (s, 2H), 7.38 (d, J=9.00 Hz, 2H), 7.43 (d, J=8.61 Hz, 1H), 7.75 (d, J=8.61 Hz, 2H), 8.30 (d, J=8.22 Hz, 1H), 9.64 (s, 1H).

Compound 1074; MS: m/z=390.0 (MH⁺); ¹H NMR (400 MHz, DMSO-d₆) δ ppm 7.38 (t, J=9.00 Hz, 1H) 7.58 (s, 2H) 7.65 (ddd, J=9.10, 4.40, 2.54 Hz, 1H) 7.98-8.03 (m, 1H) 9.01-9.06 (m, 2H) 9.78 (s, 1H).

Compound 1075; MS: m/z=374.0 (MH⁺); ¹H NMR (400 MHz, DMSO-d₆) δ ppm 7.39 (dt, J=10.56, 9.19 Hz, 1H) 7.44-7.53 (m, 1H) 7.57 (br. s., 2H) 7.85 (ddd, J=13.40, 7.53, 2.54 Hz, 1H) 9.03 (d, J=4.70 Hz, 2H) 9.79 (br. s., 1H).

Compound 1076; MS: 370.0 m/z=(MH⁺); ¹H NMR (400 MHz, DMSO-d₆) δ ppm 2.22 (d, J=1.96 Hz, 3H) 7.09 (t, J=9.19 Hz, 1H) 7.45-7.54 (m, 3H) 7.60 (dd, J=7.04, 2.35 Hz, 1H) 9.02 (s, 2H) 9.58 (s, 1H).

Compound 1077; MS: m/z=356.0 (MH⁺); ¹H NMR (400 MHz, DMSO-d₆) δ ppm 6.85-6.93 (m, 1H) 7.35 (td, J=8.12, 6.85 Hz, 1H) 7.48-7.54 (m, 1H) 7.58 (s, 2H) 7.67 (dt, J=12.03, 2.20 Hz, 1H) 9.00-9.07 (m, 2H) 9.76 (s, 1H).

Compound 1078; MS: m/z=370.0 (MH⁺); ¹H NMR (400 MHz, DMSO-d₆) δ ppm 2.18 (s, 3H) 7.20 (t, J=8.61 Hz, 1H) 7.40 (dd, J=8.22, 1.96 Hz, 1H) 7.54 (br. s., 2H) 7.60 (dd, J=12.52, 1.96 Hz, 1H) 9.03 (d, J=4.70 Hz, 2H) 9.68 (br. s., 1H).

Compound 1079; MS: m/z=374.0 (MH⁺); ¹H NMR (400 MHz, DMSO-d₆) δ ppm 6.91 (tt, J=9.39, 2.35 Hz, 1H) 7.47-7.56 (m, 2H) 7.64 (s, 2H) 9.05 (dd, J=11.15, 1.76 Hz, 2H) 9.89 (s, 1H).

Compound 1080; MS: m/z=368.0 (MH⁺); ¹H NMR (400 MHz, DMSO-d₆) δ ppm 3.75 (s, 3H), 6.92 (d, J=9.00 Hz, 2H), 7.39 (s, 2H), 7.58 (d, J=9.00 Hz, 2H), 8.70 (s, 1H), 9.37 (s, 1H), 9.70 (s, 1H).

Compound 1081; MS: m/z=340.1 (MH⁺); ¹H NMR (400 MHz, DMSO-d₆) δ ppm 2.14 (quin, J=7.53 Hz, 2H), 3.00 (q, J=7.56 Hz, 2H), 3.74 (s, 3H), 6.89 (d, J=9.39 Hz, 2H), 7.23 (s, 2H), 7.56 (d, J=9.00 Hz, 1H), 8.26 (s, 1H), 9.25 (s, 1H).

Compound 1082; MS: m/z=344.0/346.0 (MH⁺); ¹H NMR (400 MHz, DMSO-d₆) δ ppm 2.14 (quin, J=7.53 Hz, 2H), 3.01 (q, J=7.56 Hz, 4H), 7.33 (s, 2H), 7.36 (d, J=8.61 Hz, 2H), 7.74 (d, J=9.00 Hz, 2H), 8.29 (s, 1H), 9.48 (s, 1H).

Compound 1083; MS: m/z=367.0 (MH⁺); ¹H NMR (400 MHz, DMSO-d₆) δ ppm 3.75 (s, 3H), 6.91 (d, J=9.00 Hz, 2H), 7.37 (s, 2H), 7.57 (d, J=9.00 Hz, 2H), 7.78 (d, J=8.61 Hz, 1H), 8.14 (d, J=8.61 Hz, 1H), 8.60 (s, 1H), 9.42 (s, 1H).

Compound 1084; MS: m/z=422.0 (MH⁺); ¹H NMR (400 MHz, DMSO-d₆) δ ppm 7.35 (d, J=8.61 Hz, 2H), 7.57 (br. s, 2H), 7.82 (d, J=9.00 Hz, 2H), 9.02-9.09 (m, 2H), 9.80 (s, 1H).

Compound 1085; MS: m/z=368.0 (MH⁺); ¹H NMR (400 MHz, DMSO-d₆) δ ppm 3.75 (s, 3H), 6.67 (dd, J=8.22, 2.35 Hz, 1H), 7.23 (t, J=8.22 Hz, 1H), 7.32 (dd, J=9.00, 1.56 Hz, 1H), 7.39 (t, J=2.15 Hz, 1H), 7.54 (br. s, 2H), 9.01-9.08 (m, 2H), 9.57 (s, 1H).

Compound 1086; MS: m/z=404.0 (MH⁺); ¹H NMR (400 MHz, DMSO-d₆) δ ppm 7.16 (d, J=9.00 Hz, 2H), 7.18 (t, J=73.95 Hz, 1H), 7.54 (s, 2H), 7.73 (d, J=9.39 Hz, 2H), 8.97-9.11 (m, 2H), 9.71 (s, 1H).

Compound 1087; MS: m/z=402.0/404.0 (MH⁺); ¹H NMR (400 MHz, DMSO-d₆) δ ppm 3.84 (s, 3H), 7.14 (d, J=9.00 Hz, 1H), 7.54 (s, 2H), 7.60 (dd, J=9.00, 2.74 Hz, 1H), 7.87 (d, J=2.35 Hz, 1H), 8.99-9.09 (m, 2H), 9.62 (s, 1H).

Compound 1088; MS: m/z=356.0 (MH⁺); ¹H NMR (400 MHz, DMSO-d₆) δ ppm 7.19 (t, J=9.00 Hz, 2H), 7.44 (s, 2H), 7.70 (dd, J=9.00, 5.09 Hz, 2H) 8.72 (s, 1H), 9.39 (s, 1H), 9.86 (s, 1H).

Compound 1089; MS: m/z=355.0 (MH⁺); ¹H NMR (400 MHz, DMSO-d₆) δ ppm 7.17 (t, J=8.80 Hz, 2H), 7.42 (s, 2H), 7.70 (dd, J=9.39, 5.09 Hz, 2H), 7.79 (dd, J=8.61, 1.57 Hz, 1H), 8.15 (d, J=8.22 Hz, 1H), 8.62 (s, 1H), 9.58 (s, 1H).

Compound 1090; Described in example 20

Compound 1091; MS: m/z=310.1 (MH⁺); ¹H NMR (400 MHz, DMSO-d₆) δ ppm 0.80 (d, J=5.09 Hz, 2H), 1.07 (d, J=7.83 Hz, 2H), 2.06-2.13 (m, 1H), 7.07 (t, J=7.24 Hz, 1H), 7.27-7.35 (m, 4H), 7.69 (d, J=8.22 Hz, 2H), 8.15 (s, 1H), 8.57 (s, 1H), 9.39 (s, 1H).

Compound 1092; MS: m/z=430.0 (MH⁺); ¹H NMR (400 MHz, DMSO-d₆) δ ppm 6.95-7.03 (m, 4H) 7.07-7.14 (m, 1H) 7.33-7.41 (m, 2H) 7.50 (s, 2H) 7.65-7.72 (m, 2H) 9.02 (s, 2H) 9.64 (s, 1H).

Compound 1093; MS: m/z=372.0 (MH⁺); ¹H NMR (400 MHz, DMSO-d₆) δ ppm 7.12 (dt, J=9.10, 0.93 Hz, 1H) 7.34 (t, J=8.22 Hz, 1H) 7.52-7.69 (m, 3H) 7.90 (t, J=1.96 Hz, 1H) 8.98-9.09 (m, 2H) 9.75 (br. s., 1H).

Compound 1094; MS: m/z=352.0 (MH$^+$); $^1$H NMR (400 MHz, DMSO-d$_6$) δ ppm 2.29 (s, 3H) 6.90 (d, J=7.83 Hz, 1H) 7.20 (t, J=7.83 Hz, 1H) 7.43-7.57 (m, 4H) 9.02 (d, J=0.78 Hz, 2H) 9.52 (s, 1H).

Compound 1095; MS: m/z=407.9 (MH$^+$); $^1$H NMR (400 MHz, DMSO-d$_6$) δ ppm 7.57 (d, J=9.00 Hz, 1H) 7.61 (br. s., 2H) 7.69 (dd, J=8.80, 2.54 Hz, 1H) 8.10 (d, J=2.35 Hz, 1H) 9.00-9.08 (m, 2H) 9.83 (br. s., 1H).

Compound 1096; MS: m/z=386.0 (MH$^+$); $^1$H NMR (400 MHz, DMSO-d$_6$) δ ppm 2.31 (s, 3H) 7.34 (d, J=8.61 Hz, 1H) 7.51-7.58 (m, 3H) 7.71 (d, J=2.35 Hz, 1H) 9.03 (d, J=3.52 Hz, 2H) 9.64 (s, 1H).

Compound 1097; MS: m/z=388.0 (MH$^+$); $^1$H NMR (400 MHz, DMSO-d$_6$) δ ppm 7.12 (dd, J=8.61, 2.35 Hz, 1H) 7.23 (d, J=8.61 Hz, 1H) 7.50 (d, J=2.35 Hz, 3H) 9.02 (d, J=1.96 Hz, 2H) 9.60 (s, 1H) 10.15 (s, 1H).

Compound 1098; MS: m/z=382.0 (MH$^+$); $^1$H NMR (400 MHz, DMSO-d$_6$) δ ppm 5.99 (s, 2H) 6.86 (d, J=8.22 Hz, 1H) 7.09 (dd, J=8.41, 2.15 Hz, 1H) 7.31 (d, J=1.96 Hz, 1H) 7.47 (s, 2H) 9.01 (s, 2H) 9.51 (s, 1H).

Compound 1099; MS: m/z=396.0 (MH$^+$); $^1$H NMR (400 MHz, DMSO-d$_6$) δ ppm 4.15-4.26 (m, 4H) 6.79 (d, J=9.00 Hz, 1H) 7.11 (dd, J=8.80, 2.54 Hz, 1H) 7.27 (d, J=2.35 Hz, 1H) 7.46 (br. s., 2H) 9.01 (s, 2H) 9.44 (s, 1H).

Compound 1100; MS: m/z=344.0 (MH$^+$); $^1$H NMR (400 MHz, DMSO-d$_6$) δ ppm 7.34 (dd, J=5.28, 1.37 Hz, 1H) 7.45 (dd, J=5.28, 3.33 Hz, 1H) 7.53 (s, 2H) 7.66 (dd, J=3.13, 1.57 Hz, 1H) 9.02 (d, J=3.13 Hz, 2H) 10.08 (s, 1H).

Compound 1101; MS: m/z=409.0 (MH$^+$); $^1$H NMR (400 MHz, DMSO-d$_6$) δ ppm 2.78 (s, 3H) 7.55 (s, 2H) 7.70 (dd, J=9.00, 1.96 Hz, 1H) 7.94 (d, J=8.61 Hz, 1H) 8.31 (d, J=1.96 Hz, 1H) 9.04 (d, J=5.87 Hz, 2H) 9.78 (s, 1H).

Compound 1102; MS: m/z=340.0 (MH$^+$); $^1$H NMR (400 MHz, DMSO-d$_6$) δ ppm 7.76 (s, 2H) 8.08 (d, J=5.87 Hz, 1H) 8.66 (d, J=5.48 Hz, 1H) 8.91 (s, 1H) 9.05 (d, J=1.56 Hz, 1H) 9.09 (s, 1H) 10.54 (s, 1H).

Compound 1103; Described in example 21

Compound 1104; MS: m/z=324.1 (MH$^+$); $^1$H NMR (400 MHz, DMSO-d$_6$) δ ppm 1.76-1.92 (m, 4H) 2.88 (t, J=6.06 Hz, 2H) 2.95 (t, J=6.46 Hz, 2H) 7.03-7.09 (m, 1H) 7.25-7.35 (m, 4H) 7.68 (d, J=7.43 Hz, 2H) 8.18 (s, 1H) 9.34 (s, 1H).

Compound 1105; MS: m/z=354.1 (MH$^+$); $^1$H NMR (400 MHz, DMSO-d$_6$) δ ppm 1.74-1.93 (m, 4H) 2.87 (t, J=6.06 Hz, 2H), 2.95 (t, J=6.46 Hz, 2H), 3.73 (s, 3H), 6.85-6.92 (m, 2H), 7.24 (s, 2H), 7.53-7.59 (m, 2H), 8.16 (s, 1H), 9.24 (s, 1H).

Compound 1106; MS: m/z=342.1 (MH$^+$); $^1$H NMR (400 MHz, DMSO-d$_6$) δ ppm 1.76-1.92 (m, 4H) 2.87 (t, J=6.06 Hz, 2H) 2.95 (t, J=6.46 Hz, 2H) 7.11-7.18 (m, 2H) 7.29 (br. s., 2H) 7.65-7.72 (m, 2H), 8.18 (s, 1H), 9.41 (br. s., 1H).

Compound 1107; MS: m/z=340.0 (MH$^+$); $^1$H NMR (400 MHz, DMSO-d$_6$) δ ppm 7.21 (t, J=4.70 Hz, 1H) 7.61 (s, 2H) 8.68 (d, J=4.70 Hz, 2H) 9.04 (d, J=5.87 Hz, 2H) 10.42 (s, 1H).

Compound 1108; MS: m/z=340.0 (MH$^+$); $^1$H NMR (400 MHz, DMSO-d$_6$) δ ppm 7.70 (s, 2H) 8.37 (d, J=2.74 Hz, 1H) 8.45 (dd, J=2.74, 1.57 Hz, 1H) 9.01-9.06 (m, 1H) 9.08 (d, J=1.56 Hz, 1H) 9.27 (d, J=1.57 Hz, 1H) 10.44 (s, 1H).

Compound 1109; MS: m/z=340.0 (MH$^+$); $^1$H NMR (400 MHz, DMSO-d$_6$) δ ppm 7.67 (s, 2H) 8.89 (s, 1H) 9.05 (d, J=1.56 Hz, 1H) 9.08 (d, J=1.57 Hz, 1H) 9.10 (s, 2H) 10.00 (s, 1H).

Compound 1110; MS: m/z=378.0 (MH$^+$); $^1$H NMR (400 MHz, DMSO-d$_6$) δ ppm 7.44-7.52 (m, 3H) 7.53-7.59 (m, 1H) 8.03 (s, 1H) 8.06 (s, 1H) 9.02 (s, 2H) 9.64 (s, 1H) 12.99 (s, 1H).

Compound 1111; Described in example 22

Compound 1112; Described in example 23

Compound 1113; MS: m/z=338.1 (MH$^+$); $^1$H NMR (400 MHz, DMSO-d$_6$) δ ppm 1.66 (br. s., 4H), 1.85 (d, J=4.70 Hz, 2H), 2.85-2.91 (m, 2H), 3.08 (d, J=10.96 Hz, 2H), 6.99-7.13 (m, 1H), 7.21-7.37 (m, 4H), 7.63-7.75 (m, 2H), 8.19 (s, 1H), 9.35 (s, 1H).

Compound 1114; MS: m/z=314.1 (MH$^+$); $^1$H NMR (400 MHz, DMSO-d$_6$) δ ppm 2.43 (s, 3H), 3.74 (br. s, 2H), 6.90 (d, J=9.00 Hz, 2H), 7.26 (s, 2H), 7.57 (d, J=9.00 Hz, 2H), 8.30 (dd, J=2.15, 0.98 Hz, 1H), 8.53 (d, J=1.57 Hz, 1H), 9.30 (s, 1H).

Compound 1115; MS: m/z=302.1 (MH$^+$); $^1$H NMR (400 MHz, DMSO-d$_6$) δ ppm 2.43 (s, 3H), 7.16 (t, J=8.80 Hz, 2H), 7.32 (s, 2H), 7.70 (dd, J=9.39, 5.09 Hz, 2H), 8.32 (dd, J=1.96, 0.78 Hz, 1H), 8.54 (d, J=1.57 Hz, 1H), 9.47 (s, 1H).

Compound 1116; MS: m/z=368.0 (MH$^+$); $^1$H NMR (400 MHz, DMSO-d$_6$) δ ppm 3.75 (s, 3H), 6.92 (br. s, 2H), 6.93 (d, J=9.00 Hz, 2H), 7.58 (d, J=9.00 Hz, 2H), 7.99 (d, J=8.61 Hz, 1H), 8.77 (d, J=8.22 Hz, 1H), 9.63 (s, 1H).

Compound 1117; MS: m/z=356.0 (MH$^+$); $^1$H NMR (400 MHz, DMSO-d$_6$) δ ppm 6.98 (s, 2H), 7.19 (t, J=8.80 Hz, 2H), 7.71 (dd, J=9.39, 5.09 Hz, 2H), 8.01 (d, J=8.22 Hz, 1H), 8.78 (d, J=8.61 Hz, 1H), 9.79 (s, 1H).

Compound 1118; Described in example 16

Compound 1119; MS: m/z=313.1 (MH$^+$); $^1$H NMR (400 MHz, DMSO-d$_6$) δ ppm 2.43 (s, 3H), 3.74 (s, 3H), 6.89 (d, J=9.00 Hz, 2H), 7.13 (s, 2H), 7.33 (dd, J=8.41, 1.37 Hz, 1H), 7.56 (d, J=9.00 Hz, 2H), 7.74 (d, J=8.22 Hz, 1H), 7.89 (s, 1H), 9.19 (s, 1H).

Compound 1120; MS: m/z=301.1 (MH$^+$); $^1$H NMR (400 MHz, DMSO-d$_6$) δ ppm 2.43 (s, 3H), 7.15 (t, J=9.00 Hz, 2H), 7.19 (s, 2H), 7.35 (dd, J=8.41, 1.37 Hz, 1H), 7.69 (dd, J=9.00, 5.48 Hz, 1H), 7.75 (d, J=8.22 Hz, 1H), 7.91 (s, 1H), 9.37 (s, 1H).

Compound 1121; MS: m/z=386.0 (MH$^+$); $^1$H NMR (400 MHz, DMSO-d$_6$) δ ppm 3.82 (s, 3H) 7.14 (dd, J=11.35, 8.61 Hz, 1H) 7.25-7.33 (m, 1H) 7.46-7.62 (m, 3H) 9.03 (d, J=5.09 Hz, 2H) 9.61 (s, 1H).

Compound 1122; MS: m/z=382.1 (MH$^+$); $^1$H NMR (400 MHz, DMSO-d$_6$) δ ppm 1.30 (t, J=7.04 Hz, 3H) 3.99 (q, J=6.91 Hz, 2H) 6.83-6.92 (m, 2H) 7.45 (s, 2H) 7.50-7.58 (m, 2H) 9.01 (s, 2H) 9.48 (s, 1H).

Compound 1123; MS: m/z=381.0 (MH$^+$); $^1$H NMR (400 MHz, DMSO-d$_6$) δ ppm 7.23 (br. s., 1H) 7.58 (s, 2H) 7.78 (d, J=9.00 Hz, 2H) 7.84 (d, J=9.00 Hz, 3H) 9.04 (d, J=6.26 Hz, 2H) 9.78 (s, 1H).

Compound 1124; MS: m/z=395.0 (MH$^+$); $^1$H NMR (400 MHz, DMSO-d$_6$) δ ppm 2.76 (d, J=4.30 Hz, 3H) 7.58 (s, 2H) 7.79 (s, 4H) 8.32 (d, J=4.70 Hz, 1H) 9.04 (d, J=5.87 Hz, 2H) 9.77 (s, 1H).

Compound 1125; MS: m/z=396.0 (MH$^+$); $^1$H NMR (400 MHz, DMSO-d$_6$) δ ppm 3.82 (s, 3H) 7.62 (s, 2H) 7.85-7.96 (m, 4H) 8.99-9.09 (m, 2H) 9.90 (s, 1H).

Compound 1126; MS: m/z=381.1 (MH$^+$); $^1$H NMR (400 MHz, DMSO-d$_6$) δ ppm 2.86 (s, 6H) 6.69 (d, J=9.39 Hz, 2H) 7.35-7.50 (m, 4H) 8.99 (s, 2H) 9.36 (s, 1H).

Compound 1127; MS: m/z=417.0 (MH$^+$); $^1$H NMR (400 MHz, DMSO-d$_6$) δ ppm 7.25 (s, 2H) 7.62 (s, 2H) 7.72-7.80 (m, 2H) 7.85-7.93 (m, 2H) 8.99-9.10 (m, 2H) 9.90 (s, 1H).

Compound 1128; MS: m/z=357.0 (MH$^+$); $^1$H NMR (400 MHz, DMSO-d$_6$) δ ppm 7.58 (s, 2H) 7.77 (td, J=8.71, 2.93 Hz, 1H) 8.05 (dd, J=9.19, 4.11 Hz, 1H) 8.37 (d, J=3.13 Hz, 1H) 8.99-9.08 (m, 2H) 10.16 (s, 1H).

Compound 1129; MS: m/z=314.1 (MH$^+$); $^1$H NMR (400 MHz, DMSO-d$_6$) δ ppm 2.63 (s, 3H), 3.75 (s, 3H), 6.75 (br.

s, 2H), 6.91 (d, J=9.00 Hz, 2H), 7.41 (d, J=8.61 Hz, 1H), 7.57 (d, J=9.00 Hz, 2H), 8.29 (d, J=8.22 Hz, 1H), 9.40 (s, 1H).

Compound 1130; MS: m/z=315.0/317.0 (M-H)⁻; ¹H NMR (400 MHz, DMSO-d₆) δ ppm 2.43 (s, 3H), 7.23 (s, 2H), 7.35 (dd, J=7.83, 1.57 Hz, 1H), 7.36 (d, J=9.00 Hz, 3H), 7.76 (d, J=8.22 Hz, 1H), 7.74 (d, J=9.00 Hz, 3H), 7.92 (s, 1H), 9.43 (s, 1H).

Compound 1131; LCMS: m/z=297.1 (MH⁺); ¹H NMR (400 MHz, DMSO-d₆) δ ppm 2.27 (s, 3H), 2.43 (s, 3H), 7.12 (d, J=8.22 Hz, 2H), 7.16 (s, 2H), 7.34 (dd, J=8.22, 0.78 Hz, 1H), 7.56 (d, J=8.22 Hz, 2H), 7.75 (d, J=8.22 Hz, 1H), 7.90 (s, 1H), 9.22 (s, 1H).

Compound 1132; MS: m/z=361.0/363.0 (MH⁺); ¹H NMR (400 MHz, DMSO-d₆) δ ppm 2.43 (s, 3H), 7.24 (s, 2H), 7.35 (dd, J=8.22, 1.17 Hz, 1H), 7.49 (d, J=9.00 Hz, 2H), 7.69 (d, J=9.00 Hz, 2H), 7.76 (d, J=8.22 Hz, 1H), 7.92 (s, 1H), 9.43 (s, 1H).

Compound 1133; MS: m/z=384.0 (MH⁺); ¹H NMR (400 MHz, DMSO-d₆) δ ppm 2.45 (s, 3H), 7.24 (m, J=8.61 Hz, 2H), 7.51 (s, 2H), 7.65 (m, J=8.61 Hz, 2H), 9.02 (d, J=1.17 Hz, 2H), 9.61 (s, 1H).

Compound 1134; Described in example 24

Compound 1135; MS: m/z=348.2/350.2 (MH⁺); ¹H NMR (400 MHz, DMSO-d₆) δ ppm 2.43 (s, 3H), 3.83 (s, 3H), 7.11 (d, J=9.00 Hz, 1H), 7.32 (br. s., 2H), 7.58 (dd, J=9.00, 2.35 Hz, 1H), 7.87 (d, J=2.74 Hz, 1H), 8.31 (s, 1H), 8.52 (s, 1H), 9.42 (br. s., 1H).

Compound 1136; MS: m/z=401.0/403.0 (MH⁺); ¹H NMR (400 MHz, DMSO-d₆) δ ppm 3.84 (s, 3H), 7.13 (d, J=9.00 Hz, 1H), 7.43 (s, 2H), 7.60 (dd, J=9.00, 2.74 Hz, 1H), 7.79 (d, J=8.61 Hz, 1H), 7.86 (d, J=2.74 Hz, 1H), 8.15 (d, J=8.22 Hz, 1H), 8.62 (s, 1H), 9.53 (s, 1H).

Compound 1137; MS: m/z=352.2 (MH⁺); ¹H NMR (400 MHz, DMSO-d₆) δ ppm 2.43 (s, 3H), 7.42 (br. s., 2H), 7.67 (m, J=8.61 Hz, 2H), 7.94 (m, J=8.61 Hz, 2H), 8.34 (s, 1H), 8.53-8.56 (m, 1H), 9.74 (br. s., 1H).

Compound 1138; MS: m/z=405.0 (MH⁺); ¹H NMR (400 MHz, DMSO-d₆) δ ppm 7.54 (s, 2H), 7.69 (d, J=9.00 Hz, 2H), 7.81 (dd, J=8.61, 1.57 Hz, 1H), 7.96 (d, J=8.61 Hz, 2H), 8.17 (d, J=8.22 Hz, 1H), 8.65 (s, 1H), 9.86 (s, 1H).

Compound 1139; MS: m/z=318.1 (MH⁺); ¹H NMR (400 MHz, DMSO-d₆) δ ppm 2.41 (s, 3H) 7.07-7.13 (m, 1H) 7.33 (t, J=8.02 Hz, 1H) 7.38 (s, 2H) 7.61-7.66 (m, 1H) 7.90 (t, J=2.15 Hz, 1H) 8.33 (d, J=1.17 Hz, 1H) 8.53 (d, J=1.96 Hz, 1H) 9.54 (s, 1H).

Compound 1140; MS: m/z=298.1 (MH⁺); ¹H NMR (400 MHz, DMSO-d₆) δ ppm 2.28 (s, 3H) 2.41 (s, 3H) 6.87 (d, J=7.43 Hz, 1H) 7.18 (t, J=7.63 Hz, 1H) 7.29 (s, 2H) 7.46 (d, J=7.43 Hz, 1H) 7.53 (s, 1H) 8.28-8.32 (m, 1H) 8.52 (d, J=1.57 Hz, 1H) 9.30 (s, 1H).

Compound 1141; MS: m/z=342.1 (MH⁺); ¹H NMR (400 MHz, DMSO-d₆) δ ppm 2.41 (s, 3H) 4.16-4.24 (m, 4H) 6.77 (d, J=9.00 Hz, 1H) 7.10 (dd, J=8.80, 2.54 Hz, 1H) 7.20-7.31 (m, 3H) 8.29 (d, J=1.17 Hz, 1H) 8.51 (d, J=1.96 Hz, 1H) 9.23 (s, 1H).

Compound 1142; MS: m/z=328.1 (MH⁺); ¹H NMR (400 MHz, DMSO-d₆) δ ppm 1.30 (t, J=7.04 Hz, 3H) 2.41 (s, 3H) 3.98 (q, J=6.78 Hz, 2H) 6.82-6.90 (m, 2H) 7.23 (s, 2H) 7.48-7.57 (m, 2H) 8.25-8.31 (m, 1H) 8.51 (d, J=1.96 Hz, 1H) 9.27 (s, 1H).

Compound 1143; MS: m/z=330.1 (MH⁺); ¹H NMR (400 MHz, DMSO-d₆) δ ppm 2.41 (s, 3H) 2.44 (s, 3H) 7.18-7.26 (m, 2H) 7.30 (s, 2H) 7.61-7.68 (m, 2H) 8.30 (d, J=1.17 Hz, 1H) 8.52 (d, J=1.56 Hz, 1H) 9.40 (s, 1H).

Compound 1144; MS: m/z=371.0 (MH⁺); ¹H NMR (400 MHz, DMSO-d₆) δ ppm 7.11 (dt, J=6.85, 1.08 Hz, 1H) 7.34 (t, J=8.02 Hz, 1H) 7.48 (s, 2H) 7.60-7.67 (m, 1H) 7.79 (dd, J=8.61, 1.57 Hz, 1H) 7.89 (t, J=2.15 Hz, 1H) 8.14 (d, J=8.61 Hz, 1H) 8.62 (s, 1H) 9.66 (s, 1H).

Compound 1145; MS: m/z=351.0 (MH⁺); ¹H NMR (400 MHz, DMSO-d₆) δ ppm 2.28 (s, 3H) 6.89 (d, J=7.43 Hz, 1H) 7.19 (t, J=7.63 Hz, 1H) 7.40 (s, 2H) 7.46 (d, J=8.61 Hz, 1H) 7.53 (s, 1H) 7.77 (dd, J=8.61, 1.57 Hz, 1H) 8.13 (d, J=8.61 Hz, 1H) 8.60 (s, 1H) 9.42 (s, 1H).

Compound 1146; MS: m/z=395.0 (MH⁺); ¹H NMR (400 MHz, DMSO-d₆) δ ppm 4.15-4.26 (m, 4H) 6.78 (d, J=8.61 Hz, 1H) 7.10 (dd, J=8.80, 2.54 Hz, 1H) 7.26 (d, J=2.74 Hz, 1H) 7.35 (s, 2H) 7.76 (dd, J=8.61, 1.57 Hz, 1H) 8.12 (d, J=8.61 Hz, 1H) 8.58 (s, 1H) 9.34 (s, 1H).

Compound 1147; MS: m/z=381.1 (MH⁺); ¹H NMR (400 MHz, DMSO-d₆) δ ppm 1.30 (t, J=6.85 Hz, 3H) 3.99 (q, J=6.78 Hz, 2H) 6.84-6.91 (m, 2H) 7.34 (s, 2H) 7.50-7.56 (m, 2H) 7.76 (dd, J=8.61, 1.57 Hz, 1H) 8.12 (d, J=8.61 Hz, 1H) 8.58 (s, 1H) 9.38 (s, 1H).

Compound 1148; MS: m/z=383.0 (MH⁺); ¹H NMR (400 MHz, DMSO-d₆) δ ppm 2.45 (s, 3H) 7.19-7.26 (m, 2H) 7.41 (s, 2H) 7.60-7.69 (m, 2H) 7.77 (dd, J=8.61, 1.57 Hz, 1H) 8.13 (d, J=8.22 Hz, 1H) 8.60 (s, 1H) 9.52 (s, 1H).

Compound 1149; MS: m/z=368.0 (MH⁺); ¹H NMR (400 MHz, DMSO-d₆) δ ppm 2.42 (s, 3H) 7.31 (d, J=8.22 Hz, 2H) 7.35 (s, 2H) 7.77-7.83 (m, 2H) 8.32 (d, J=1.17 Hz, 1H) 8.53 (d, J=1.96 Hz, 1H) 9.58 (s, 1H).

Compound 1150; MS: m/z=290.0 (MH⁺); ¹H NMR (400 MHz, DMSO-d₆) δ ppm 2.41 (s, 3H) 7.28-7.39 (m, 3H) 7.43 (dd, J=5.09, 3.52 Hz, 1H) 7.64 (dd, J=3.33, 1.37 Hz, 1H) 8.30 (d, J=1.17 Hz, 1H) 8.52 (d, J=1.96 Hz, 1H) 9.88 (s, 1H).

Compound 1151; MS: m/z=421.0 (MH⁺); ¹H NMR (400 MHz, DMSO-d₆) δ ppm 7.32 (d, J=8.61 Hz, 2H) 7.45 (s, 2H) 7.75-7.84 (m, 3H) 8.15 (d, J=8.22 Hz, 1H) 8.62 (s, 1H) 9.70 (s, 1H).

Compound 1152; MS: m/z=343.0 (MH⁺); ¹H NMR (400 MHz, DMSO-d₆) δ ppm 7.34 (dd, J=5.09, 1.17 Hz, 1H) 7.39-7.47 (m, 3H) 7.65 (dd, J=3.13, 1.17 Hz, 1H) 7.77 (dd, J=8.41, 1.37 Hz, 1H) 8.13 (d, J=8.22 Hz, 1H) 8.60 (s, 1H) 9.99 (s, 1H).

Compound 1153; Described in example 25

Compound 1154; MS: m/z=340.0 (MH⁺); ¹H NMR (400 MHz, DMSO-d₆) δ ppm 6.56 (s, 2H), 7.17 (t, J=8.61 Hz, 2H), 7.85 (dd, J=9.39, 5.09 Hz, 2H), 8.88 (d, J=2.35 Hz, 1H), 8.90 (d, J=1.96 Hz, 1H), 10.21 (s, 1H).

Materials and Methods Related to Examples 1 and 2 (Table 1 and 2)

Example 1

CD34+ Activity Assessment

Human CD34+ cord blood (CB) cells were isolated from fresh units using RosetteSep™ 0034 pre-enrichment cocktail followed by CD34 positive selection using EasySep Kit™ (StemCell Technologies). The cells were then pre-expanded in bulk, by culturing at 37° C. for 6 days in HSC expansion media consisting of StemSpan ACF (StemCell Technologies) supplemented with 100 ng/mL Stem Cell Factor (SCF, Shenandoah), 100 ng/mL FMS-like Tyrosine Kinase 3 Ligand (FLT3L, Shenandoah), 50 ng/mL Thrombopoietin (TPO, Shenandoah), 2 mM GlutaMAX™ (Invitrogen), 10 μg/mL low density lipoproteins (LDL, StemCell Technologies), 10 μg/mL Ciprofloxacin and 35 nM UM0128171. The culture was monitored daily and supplemented with fresh media as required. Following the pre-expansion, cells were harvested, aliquoted and frozen until use.

For each activity assessment, CD34+ pre-expanded cells (approximately 2000 per well in a 384-well plate) were cultured in HSC expansion media, in the presence of 35 nM UM0128171. Compounds were serially diluted (1/2) in DMSO (10 dilutions per compound) and added to the cells in order to achieve a 1/1000 final dilution. StemRegenin1 (SR1) and/or Compound 1001 were included in all experiments as controls to monitor assay performance. The plate was incubated at 37° C. for 7 days in static conditions (i.e. no shaking and no addition of media). Flow cytometry analysis was performed at the end of the 7-day expansion. Cells were stained with PE-labeled anti-human CD45RA (BD Biosciences) and APC-labeled anti-human CD34 (BD Biosciences) and analyzed using Intellicyt IQue cytometer equipped with ForeCyt software. Gates were drawn around the populations of interest to obtain cell numbers and relative proportions. The $EC_{1.5}$ value, which is the concentration at which the compound/vehicle ratio is greater or equal to 1.5, was calculated by plotting the CD34+ cell number against concentrations (log-scale) in a 4-PL curve and fitting the curve using IDBS XLfit (set model 251) in Microsoft Excel. Results are presented in Tables 1 and 2.

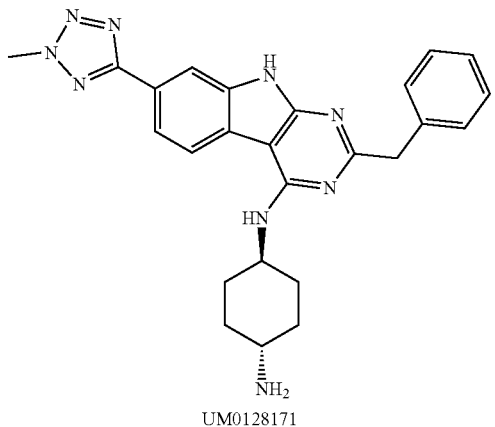 [SMILES: Cn1nnc(-c2ccc3c(c2)[nH]c2nc(Cc4ccccc4)nc(N[C@H]4CC[C@H](N)CC4)c23)n1 ; "UM0128171"]

UM0128171

Example 2

Inhibition of AhR-Mediated Gene Transcription

HEK cells line was transfected with an AhR-responsive firefly luciferase reporter gene X4-4.27 and the stable transfectants generated were again transfected with phRL-CMV (a *Renilla* luciferase expression vector; Promega) along with pBAsi-hU6 Pur DNA (a plasmid carrying the puromycin-resistant gene; TaKaRa, Shiga, Japan), and maintained in the presence of both hygromycin B and puromycin (2 mg/mL). One of the resultant clones was named HEK-XRE 11.1, and used in the reporter gene assays.

HEK-XRE 11.1 cells were plated in 384-well plates at a density of 25,000 cells in 50 uL volume per well. The induction of ARh pathway was done by addition of MeBIO at 0.1 nM concentration. ARh antagonist compounds were then added to seeded cells in serial dilutions (8 dilutions, 1:3, 10 mM down to 5 nM) in duplicate wells. *Renilla* expression was not used as internal control. On each plate, Compound 1001 and SR1 were added as dose control (8 dilutions, 1:3, 5 mM down to 2.5 nM for SR1 and 2 mM down to 1 nM for compound 1001). Luminescence activity was evaluated after 24 hours culture using Lumi-384-CellTiterGlo-Corning protocol. Dose-response curves were generated using nonlinear regression in Excel. Results are presented in Tables 1 and 2.

Materials and Methods Related to Examples 3 to 4 (FIGS. 1 and 2)

Example 3

Assessment of Cell Composition In Vitro

Human CD34+ cord blood (CB) cells from three cord blood units were isolated as previously described and frozen until use. In a first experiment, two units were pooled upon thawing and CB CD34$^+$ cells were cultured for 7 days in HSC expansion media supplemented with 35 nM UM0128171 (referred to as UM171), 1 µM Compound 1001, a combination of both or DMSO. Cultures were monitored daily and supplemented with fresh media as required. In a second experiment, one unit was thawed and CB CD34$^+$ cells were cultured for 7 days in HSC expansion media supplemented with 0.5 µM Compound 1001 (alone or in combination with nM UM171), 0.5 µM Compound 1114 (alone or in combination with 35 nM UM171), 0.5 µM SR1 (alone or in combination with 35 nM UM171), DMSO or 35 nM UM171.

Phenotype of unexpanded (d0) and expanded (d7) CB cells were analysed using a combination of the following anti-human antibodies: CD34 (BD Biosciences), CD45RA (BD Biosciences or BioLegend), CD201, CD90 and CD117 (from BioLegend), CD86 and FcεR1 (both from eBiosciences). Following staining under reduced light at room temperature for 15-30 minutes, cells were washed and analyzed on a FACSCanto II (BD Biosciences) flow cytometer. Fold expansion was calculated by dividing the number of live total cells obtained following expansion by the number of live total cells seeded for each condition. For each subpopulation of interest, the absolute cell numbers were calculated as follows:

(cell percentage of subpopulation of interest×live total cell count)/100

Figure 1B:
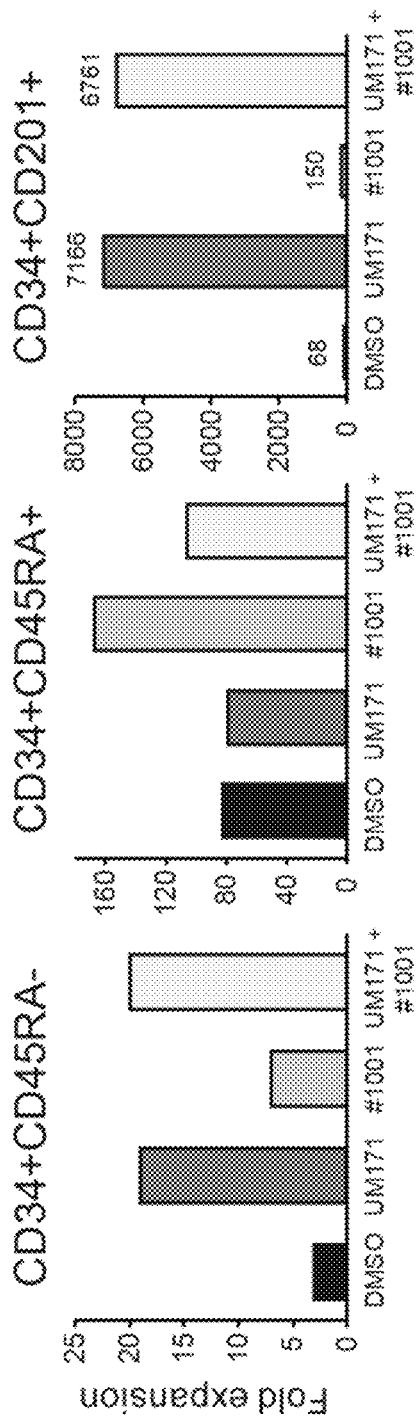
FIG. 1B depicts the fold expansion of CD34+CD45RA−, CD34+CD45RA+ and CD34+CD201+ cells in the different culture conditions compared to fresh samples.

Whereas the total number of cells in culture was increased in all conditions (FIG. 1A, left panel), the use of Compound 1001 in CB cultures increases the number of CD34+ cells (i.e. hematopoietic stem and progenitor cells) compared to other conditions (FIG. 1A, middle). The combined use of UM171 and Compound 1001 or Compound 1114 increased the overall percentage of CD34+ cells in cultures (FIG. 1A, right panel and FIG. 1D). The presence of Compound 1001 or Compound 1114, alone or in combination with UM171, favors the expansion of CD34+CD45RA+ cells (FIGS. 1B, 1C and 1D), enriched in short term progenitors (Doulatov, Sergei, et al., *Nature immunology* 11.7 (2010): 585). On the other hand, the presence of UM171 in culture, alone or in combination with Compound 1001 or Compound 1114, increases the expansion (FIG. 1B) and proportions (FIGS. 1C and 1D) of CD34+CD45RA− and CD34+CD201+ cells, enriched in long-term progenitors (Majeti, Ravindra, Christopher Y. Park, and Irving L. Weissman. *Cell stem cell* 1.6 (2007): 635-645; Notta, Faiyaz, et al. *Science* 333.6039 (2011): 218-221 and Fares, Iman, et al. *Blood* (2017): blood-2016). The combined use of UM171 and Compound 1001 or Compound 1114 also increased the percentage of Dendritic Cells and Mast Cells compared to Compounds used alone (FIG. 1D). Therefore, we can induce different proportions of the different types of hematopoietic progenitors or other cellular types depending on the presence of UM171 and Compound 1001 or Compound 1114.

Example 4

Assessment of Engraftment and Myeloid Vs Lymphoid Lineage Contribution In Vivo

NSG (NOD.Cg-Prkdcscid Il2rgtmIWjI/SzJ, The Jackson Laboratory, ME, USA) mice were bred and housed under specific-pathogen-free conditions in sterile ventilated racks at the Institute for Research in Immunology and Cancer. All animal work was in accordance with the Canadian Council on Animal Care guidelines and approved by the Comité de Déontologie et Expérimentation Animale de l'Université de Montréal.

Human CD34+ cord blood (CB) cells from two cord blood units were isolated as previously described and frozen until use. Upon thawing, both units were pooled and CB CD34+ cells were cultured for 7 days in HSC expansion media supplemented with 35 nM UM0128171, 1 µM Compound 1001, a combination of both or DMSO. Cultures were monitored daily and supplemented with fresh media as required.

Two thousand unexpanded CD34+ CB cells or their progeny present in 7-day cultures were transplanted by tail vein injection into sub-lethally irradiated (250 cGy, <24 hr before transplantation) 8 to 12 week-old female NSG (NOD-Scid IL2Rγnull, Jackson Laboratory). Human cells in NSG bone marrow (BM) was monitored by flow cytometry 3, 12 and 20 weeks post-transplantation. NSG BM cells were collected by femoral aspiration (weeks 3 and 12) or by flushing the two femurs when animals were sacrificed at week 20. Flow cytometry analysis was performed on freshly collected BM cells. Cells were treated with 1× red blood cell lysis buffer (StemCell Technologies), washed and stained with anti-human CD45 (BioLegend), anti-mouse CD45.1 (eBioscience) and anti-human CD33, anti-human CD19, anti-human CD3 and anti-human CD34 (all from BD Biosciences). Cells then were washed and analyzed using a FACSCanto II (BD Biosciences).

Figure 2A:
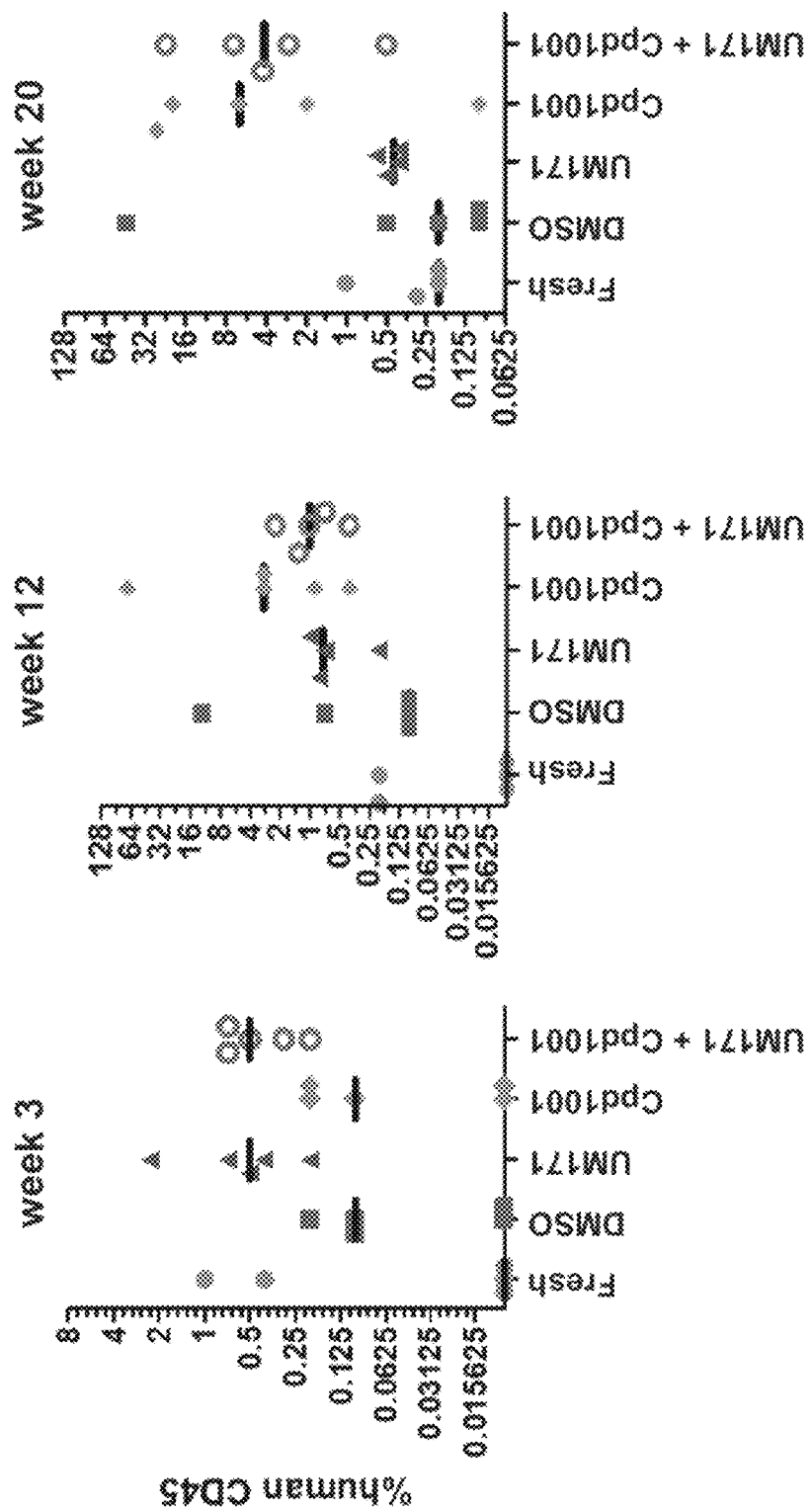
FIG. 2A shows the engraftment (as the percentage of human CD45+ cells in bone marrow aspirate) of human cord blood cells from fresh samples or in vitro expanded-samples in the different culture conditions.
Figure 2B:
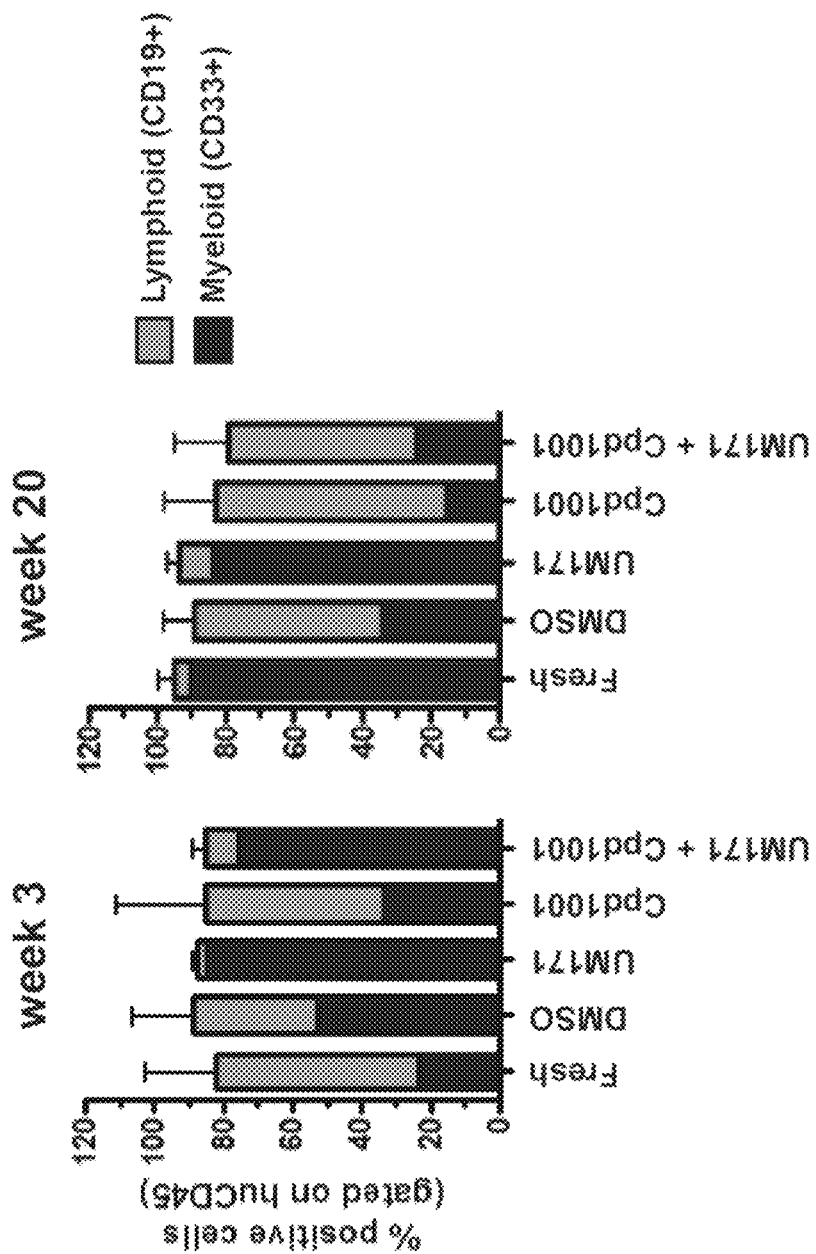
FIG. 2B show the proportions of myeloid and lymphoid cells in engrafted human cord blood cells in mice.

While CB cells expanded in the presence UM171, alone or in combination with Compound 1001, resulted in higher engraftment at 3 weeks post transplantation, CB cells expanded in the presence of Compound 1001, alone or in combination with UM171, engrafted with higher efficiency in the long term (12 and 20 weeks post transplantation, FIG. 2A). Furthermore, the contribution of lymphoid lineage was greatly increased in the presence of Compound 1001 (FIG. 2B).

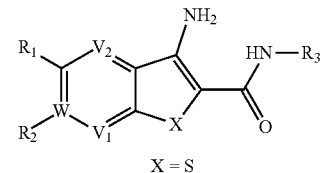

X = S

TABLE 1

| Cpd# | V₁ | V₂ | W | R₁ | R₂ | R₃ | procedures | EC1.5 (nM) | AHR (nM) |
|---|---|---|---|---|---|---|---|---|---|
| 1001 | N | CH | C | (CH₂)₃ | | Ph | A1, B1, C1 | <100 | <50 |
| 1002 | N | CH | C | (CH₂)₃ | | 4-F—Ph | A1, B1, C1 | 100-1000 | <50 |
| 1003 | N | CH | C | Br | H | Ph | A0, B1, C2 | 100-1000 | <50 |
| 1004 | N | CH | C | Cl | H | Ph | A0, B1, C1 | 100-1000 | <50 |
| 1005 | N | CH | C | CH₃ | CH₃ | Ph | A0, B1, C1 | 100-1000 | 50-500 |
| 1006 | N | CH | C | (CH₂)₃ | | 3-pyridinyl | A1, B1, C1 | 1000-5000 | 50-500 |
| 1007 | N | CH | C | (CH₂)₃ | | 2-pyridinyl | A1, B2, C1 | 100-1000 | <50 |
| 1008 | N | CH | C | CF₃ | H | Ph | A2, B1, C1 | 100-1000 | >500 |
| 1009 | N | CH | C | CH₃ | H | Ph | A3, B1, C3 | 100-1000 | <50 |
| 1010 | N | CH | C | F | H | Ph | A0, B1, C3 | >5000 | 50-500 |
| 1011 | N | CH | C | Cl | H | 4-pyridinyl | A0, B2, C3 | 1000-5000 | <50 |
| 1012 | N | CH | C | Br | H | 4-pyridinyl | A0, B2, C1 | 100-1000 | 50-500 |
| 1013 | N | CH | C | CF₃ | H | 4-pyridinyl | A2, B2, C3 | 100-1000 | >500 |
| 1014 | N | CH | C | (CH₂)₃ | | 4-pyridinyl | A1, B2, C1 | 1000-5000 | 50-500 |
| 1015 | N | CH | C | CF₃ | H | 3-pyridinyl | A2, B1, C3 | 100-1000 | >500 |
| 1016 | N | CH | C | CN | H | Ph | A4, B1, C1 | 100-1000 | >500 |
| 1017 | N | CH | C | CF₃ | H | 4-(CH₂CH₂OH)—Ph | A2, B3, C1 | 100-1000 | 50-500 |
| 1018 | N | CH | C | CF₃ | H | 4-(CH₂OCH₃)—Ph | A2, B2, C1 | 1000-5000 | <50 |
| 1019 | N | CH | C | CF₃ | H | 4-(CH₂OH)—Ph | A2, B3, C1 | >5000 | >500 |
| 1020 | N | CH | C | CCH | H | 4-pyridinyl | Example 18 | >5000 | 50-500 |
| 1021 | N | CH | C | Et | H | 4-pyridinyl | Example 19 | 100-1000 | 50-500 |
| 1022 | N | CH | C | CF₃ | H | 2-pyridinyl | A2, B2, C1 | 100-1000 | <50 |
| 1023 | N | CH | C | CF₃ | H | 5-CH₃-2-thiazolyl | A2, B2, C1 | >5000 | 50-500 |
| 1024 | N | CH | C | CF₃ | H | 4-Et—Ph | A2, B2, C1 | 100-1000 | <50 |
| 1025 | CH | CH | N | CF₃ | | Ph | A5, B1, C3 | 100-1000 | <50 |
| 1026 | CH | CH | N | CF₃ | | 4-pyridinyl | A5, B2, C3 | 1000-5000 | 50-500 |
| 1027 | CH | N | C | CF₃ | H | Ph | A6, B1, C3 | >5000 | <50 |
| 1028 | CH | N | C | CF₃ | H | 4-pyridinyl | A6, B2, C3 | >5000 | 50-500 |
| 1029 | N | CH | C | CF₃ | H | 6-benzothiazolyl | A2, B2, C2 | 100-1000 | 50-500 |
| 1030 | N | CH | C | CF₃ | H | 4-Ph—Ph | A2, B2, C2 | >5000 | 50-500 |
| 1031 | N | CH | C | CF₃ | H | 4-BnO—Ph | A2, B2, C2 | 100-1000 | 50-500 |
| 1032 | N | CH | C | CF₃ | H | 4-(CH₂CO₂Et)—Ph | A2, B2, C1 | 1000-5000 | 50-500 |
| 1033 | N | CH | C | CF₃ | H | (4-OCH₃-3-Ph)—Ph | A2, B2, C4 | 100-1000 | 50-500 |
| 1034 | CH | CH | C | CF₃ | H | Ph | A0, B1, C3 | 100-1000 | <50 |
| 1035 | CH | CH | C | CF₃ | H | 4-pyridinyl | A0, B2, C3 | 100-1000 | <50 |
| 1036 | N | CH | C | CF₃ | H | 3-Br—Ph | A2, B2, C2 | 100-1000 | <50 |
| 1037 | N | CH | C | CF₃ | H | 4-Br—Ph | A2, B2, C2 | 100-1000 | <50 |

TABLE 1-continued

| Cpd# | $V_1$ | $V_2$ | W | $R_1$ | $R_2$ | $R_3$ | procedures | EC1.5 (nM) | AHR (nM) |
|---|---|---|---|---|---|---|---|---|---|
| 1038 | N | CH | C | $CF_3$ | H | 4-($CH_2CN$)—Ph | A2, B2, C4 | >5000 | <50 |
| 1039 | N | CH | C | $CF_3$ | H | 5-isoquinolinyl | A2, B2, C2 | >5000 | 50-500 |
| 1040 | N | CH | C | $CF_3$ | H | 5-quinolinyl | A2, B2, C2 | >5000 | 50-500 |
| 1041 | N | CH | C | $CF_3$ | H | 6-quinolinyl | A2, B2, C2 | 1000-5000 | 50-500 |
| 1042 | N | CH | C | $CF_3$ | H | 3-quinolinyl | A2, B2, C2 | 1000-5000 | >500 |
| 1043 | N | CH | C | $CF_3$ | H | 4-quinolinyl | A2, B2, C2 | >5000 | >500 |
| 1044 | N | CH | C | $CO_2Et$ | H | Ph | A7, B1, C3 | >5000 | 50-500 |
| 1045 | N | CH | C | $CF_3$ | H | 4-Cl—Ph | A2, B1, C1 | <100 | <50 |
| 1046 | N | CH | C | $CF_3$ | H | 4-($CH_2CH_2OMe$)—Ph | A2, B1, C3 | >5000 | 50-500 |
| 1047 | N | CH | C | $CF_3$ | H | 4-$CH_3$—Ph | A2, B1, C1 | 100-1000 | <50 |
| 1048 | N | CH | C | $CF_3$ | H | 4-$OCH_3$—Ph | A2, B1, C1 | <100 | <50 |
| 1049 | CH | CH | N | $CF_3$ | | 4-Br—Ph | A5, B1, C4 | 100-1000 | 50-500 |
| 1050 | CH | N | C | $CF_3$ | H | 4-Br—Ph | A6, B1, C4 | >5000 | 50-500 |
| 1051 | CH | CH | N | $CF_3$ | | 4-Cl—Ph | A5, B1, C3 | 1000-5000 | 50-500 |
| 1052 | CH | CH | N | $CF_3$ | | 4-$CH_3$—Ph | A5, B1, C3 | 1000-5000 | 50-500 |
| 1053 | CH | N | C | $CF_3$ | H | 4-Cl—Ph | A6, B1, C3 | 1000-5000 | <50 |
| 1054 | CH | N | C | $CF_3$ | H | 4-$CH_3$—Ph | A6, B1, C3 | >5000 | 50-500 |
| 1055 | N | CH | C | $CF_3$ | H | 4-(3-pyridinyl)—Ph | Example 17 | >5000 | 50-500 |
| 1056 | N | CH | C | $CF_3$ | H | 4-(4-pyridinyl)—Ph | D | >5000 | 50-500 |
| 1057 | N | CH | C | $CF_3$ | H | 3-(3-pyridinyl)—Ph | D | 1000-5000 | <50 |
| 1058 | N | CH | C | $CF_3$ | H | 3-(4-pyridinyl)—Ph | D | 100-1000 | <50 |
| 1059 | N | CH | C | $CF_3$ | H | 3-Ph—Ph | D | 1000-5000 | 50-500 |
| 1060 | N | CH | C | $CF_3$ | H | 4-F—Ph | A2, B1, C2 | <100 | <50 |
| 1061 | N | CH | C | $CF_3$ | H | 4-CF3—Ph | A2, B2, C2 | <100 | <50 |
| 1062 | N | CH | C | $CH_3$ | H | 4-Br—Ph | A3, B1, C4 | <100 | <50 |
| 1063 | N | CH | C | $CH_3$ | H | 4-pyridinyl | A3, B2, C3 | >5000 | 50-500 |
| 1064 | CH | CH | C | $CF_3$ | H | 4-Br—Ph | A0, B1, C4 | 100-1000 | 50-500 |
| 1065 | CH | CH | C | $CF_3$ | H | 4-$CH_3$—Ph | A0, B1, C3 | 100-1000 | 50-500 |
| 1066 | CH | CH | C | $CF_3$ | H | 4-Cl—Ph | A0, B1, C3 | 100-1000 | <50 |
| 1067 | CH | CH | C | $CF_3$ | H | 3-pyridinyl | A0, B1, C3 | 1000-5000 | <50 |
| 1068 | N | CH | C | $CH_3$ | H | 4-Cl—Ph | A3, B1, C1 | <100 | <50 |
| 1069 | N | CH | C | $CH_3$ | H | 4-$CH_3$—Ph | A3, B1, C3 | 100-1000 | <50 |
| 1070 | N | CH | C | $CF_3$ | H | 6-$CH_3$-3-pyridinyl | A2, B1, C3 | >5000 | 50-500 |
| 1071 | N | CH | C | $CF_3$ | H | 6-$OCH_3$-3-pyridinyl | A2, B1, C1 | 100-1000 | <50 |
| 1072 | CH | N | C | $CH_3$ | H | Ph | A8, B1, C3 | >5000 | 50-500 |
| 1073 | CH | N | C | $CH_3$ | H | 4-Cl—Ph | A8, B1, C3 | >5000 | 50-500 |
| 1074 | N | CH | C | $CF_3$ | H | 3-Cl-4-F—Ph | A2, B1, C4 | 100-1000 | <50 |
| 1075 | N | CH | C | $CF_3$ | H | 3,4-diF—Ph | A2, B1, C2 | 100-1000 | <50 |
| 1076 | N | CH | C | $CF_3$ | H | 3-$CH_3$-4-F—Ph | A2, B1, C2 | 100-1000 | 50-500 |
| 1077 | N | CH | C | $CF_3$ | H | 3-F—Ph | A2, B1, C2 | 100-1000 | <50 |
| 1078 | N | CH | C | $CF_3$ | H | 3-F-4-$CH_3$—Ph | A2, B1, C2 | 1000-5000 | 50-500 |
| 1079 | N | CH | C | $CF_3$ | H | 3,5-diF—Ph | A2, B1, C4 | 1000-5000 | 50-500 |
| 1080 | CH | CH | N | $CF_3$ | | 3-$OCH_3$—Ph | A5, B1, C3 | 100-1000 | <50 |
| 1081 | N | CH | C | $(CH_2)_3$ | | 3-$OCH_3$—Ph | A1, B1, C1 | <100 | <50 |
| 1082 | N | CH | C | $(CH_2)_3$ | | 4-Cl—Ph | A1, B1, C1 | <100 | <50 |
| 1083 | CH | CH | C | $CF_3$ | H | 4-$OCH_3$—Ph | A0, B1, C3 | <100 | 50-500 |
| 1084 | N | CH | C | $CF_3$ | H | 4-$CF_3O$—Ph | A2, B1, C1 | <100 | <50 |
| 1085 | N | CH | C | $CF_3$ | H | 3-$OCH_3$—Ph | A2, B1, C1 | 100-1000 | 50-500 |
| 1086 | N | CH | C | $CF_3$ | H | 4-$OCHF_2$—Ph | A2, B1, C1 | 100-1000 | <50 |
| 1087 | N | CH | C | $CF_3$ | H | 3-Cl-4-$OCH_3$—Ph | A2, B1, C1 | <100 | <50 |
| 1088 | CH | CH | N | $CF_3$ | | 4-F—Ph | A5, B1, C3 | >5000 | <50 |
| 1089 | CH | CH | C | $CF_3$ | H | 4-F—Ph | A0, B1, C3 | 100-1000 | <50 |
| 1090 | N | CH | C | $CH_2$=CMe | H | Ph | Example 20 | >5000 | <50 |
| 1091 | N | CH | C | c-Pr | H | Ph | D | 100-1000 | 50-500 |
| 1092 | N | CH | C | $CF_3$ | H | 4-OPh—Ph | A2, B1, C2 | 100-1000 | 50-500 |
| 1093 | N | CH | C | $CF_3$ | H | 3-Cl—Ph | A2, B1, C2 | <100 | <50 |
| 1094 | N | CH | C | $CF_3$ | H | 3-$CH_3$—Ph | A2, B1, C2 | <100 | <50 |
| 1095 | N | CH | C | $CF_3$ | H | 3,4-diCl—Ph | A2, B1, C2 | 100-1000 | 50-500 |
| 1096 | N | CH | C | $CF_3$ | H | 3-$CH_3$-4-Cl—Ph | A2, B1, C2 | 1000-5000 | 50-500 |
| 1097 | N | CH | C | $CF_3$ | H | 3-OH-4-Cl—Ph | A2, B1, C1 | 1000-5000 | >500 |
| 1098 | N | CH | C | $CF_3$ | H | 3,4-($OCH_2O$)—Ph | A2, B1, C2 | <100 | 50-500 |
| 1099 | N | CH | C | $CF_3$ | H | 3,4-($OCH_2CH_2O$)—Ph | A2, B1, C2 | <100 | 50-500 |
| 1100 | N | CH | C | $CF_3$ | H | 3-thienyl | A2, B2, C2 | <100 | <50 |
| 1101 | N | CH | C | $CF_3$ | H | 2-$CH_3$-5-benzothiazolyl | A2, B2, C2 | 100-1000 | <50 |
| 1102 | N | CH | C | $CF_3$ | H | 4-pyrimidinyl | A2, B2, C2 | >5000 | 50-500 |
| 1103 | N | CH | C | i-Pr | H | Ph | Example 21 | 100-1000 | <50 |
| 1104 | N | CH | C | $(CH_2)_4$ | | Ph | A1, B1, C1 | 100-1000 | 50-500 |
| 1105 | N | CH | C | $(CH_2)_4$ | | 4-$OCH_3$—Ph | A1, B1, C1 | >5000 | 50-500 |
| 1106 | N | CH | C | $(CH_2)_4$ | | 4-F—Ph | A1, B1, C2 | 1000-5000 | 50-500 |
| 1107 | N | CH | C | $CF_3$ | H | 2-pyrimidinyl | A2, B2, C4 | 1000-5000 | <50 |
| 1108 | N | CH | C | $CF_3$ | H | 2-pyridazinyl | A2, B2, C4 | >5000 | <50 |
| 1109 | N | CH | C | $CF_3$ | H | 5-pyrimidinyl | A2, B2, C4 | >5000 | >500 |
| 1110 | N | CH | C | $CF_3$ | H | 5-indazolyl | A2, B2, C4 | >5000 | 50-500 |
| 1111 | N | CH | C | Allyl | H | Ph | Example 22 | 1000-5000 | 50-500 |
| 1112 | N | CH | C | Et | H | Ph | Example 23 | 100-1000 | 50-500 |
| 1113 | N | CH | C | $(CH_2)_5$ | | Ph | A1, B1, C2 | 1000-5000 | 50-500 |
| 1114 | N | CH | C | $CH_3$ | H | 4-$OCH_3$—Ph | A3, B1, C1 | <100 | <50 |

TABLE 1-continued

| Cpd# | V$_1$ | V$_2$ | W | R$_1$ | R$_2$ | R$_3$ | procedures | EC1.5 (nM) | AHR (nM) |
|---|---|---|---|---|---|---|---|---|---|
| 1115 | N | CH | C | CH$_3$ | H | 4-F—Ph | A3, B1, C1 | <100 | <50 |
| 1116 | CH | N | C | CF$_3$ | H | 4-OCH$_3$—Ph | A6, B1, C3 | 100-1000 | 50-500 |
| 1117 | CH | N | C | CF$_3$ | H | 4-F—Ph | A6, B1, C3 | 100-1000 | <50 |
| 1118 | CH | CH | C | CH$_3$ | H | Ph | A0, B1, C5 | >5000 | <50 |
| 1119 | CH | CH | C | CH$_3$ | H | 4-OCH$_3$—Ph | A0, B1, C5 | 100-1000 | 50-500 |
| 1120 | CH | CH | C | CH$_3$ | H | 4-F—Ph | A0, B1, C5 | <100 | <50 |
| 1121 | N | CH | C | CF$_3$ | H | 3-OCH$_3$-4-F—Ph | A2, B1, C2 | 100-1000 | 50-500 |
| 1122 | N | CH | C | CF$_3$ | H | 4-OEt—Ph | A2, B1, C4 | <100 | <50 |
| 1123 | N | CH | C | CF$_3$ | H | 4-CONH$_2$—Ph | A2, B1, C2 | >5000 | 50-500 |
| 1124 | N | CH | C | CF$_3$ | H | 4-(CONHCH$_3$)—Ph | A2, B1, C2 | 100-1000 | 50-500 |
| 1125 | N | CH | C | CF$_3$ | H | 4-(CO$_2$CH$_3$)—Ph | A2, B1, C2 | 100-1000 | 50-500 |
| 1126 | N | CH | C | CF$_3$ | H | 4-(NMe$_2$)—Ph | A2, B1, C2 | 1000-5000 | 50-500 |
| 1127 | N | CH | C | CF$_3$ | H | 4-(SO$_2$NH$_2$)—Ph | A2, B1, C2 | >5000 | 50-500 |
| 1128 | N | CH | C | CF$_3$ | H | 5-F-2-pyridinyl | A2, B1, C2 | 100-1000 | — |
| 1129 | CH | N | C | CH$_3$ | H | 4-OCH$_3$—Ph | A8, B1, C5 | 100-1000 | 50-500 |
| 1130 | CH | CH | C | CH$_3$ | H | 4-Cl—Ph | A0, B1, C5 | >5000 | 50-500 |
| 1131 | CH | CH | C | CH$_3$ | H | 4-CH$_3$—Ph | A0, B1, C5 | >5000 | 50-500 |
| 1132 | CH | CH | C | CH$_3$ | H | 4-Br—Ph | A0, B1, C5 | >5000 | 50-500 |
| 1133 | N | CH | C | CF$_3$ | H | 4-SCH$_3$—Ph | A2, B1, C4 | <100 | <50 |
| 1134 | N | CH | C | n-Pr | H | Ph | Example 24 | >5000 | <50 |
| 1135 | N | CH | C | CH$_3$ | H | 3-Cl-4-OCH$_3$—Ph | A3, B2, C2 | <100 | <50 |
| 1136 | CH | CH | C | CF$_3$ | H | 3-Cl-4-OCH$_3$—Ph | A0, B2, C1 | >5000 | <50 |
| 1137 | N | CH | C | CH$_3$ | H | 4-CF$_3$—Ph | A3, B2, C3 | <100 | <50 |
| 1138 | CH | CH | C | CF$_3$ | H | 4-CF$_3$—Ph | A0, B2, C4 | >5000 | 50-500 |
| 1139 | N | CH | C | CH$_3$ | H | 3-Cl—Ph | A3, B1, C2 | 100-1000 | <50 |
| 1140 | N | CH | C | CH$_3$ | H | 3-CH$_3$—Ph | A3, B1, C2 | 100-1000 | 50-500 |
| 1141 | N | CH | C | CH$_3$ | H | 3,4-(OCH$_2$CH$_2$O)—Ph | A3, B1, C2 | 100-1000 | 50-500 |
| 1142 | N | CH | C | CH$_3$ | H | 4-OEt—Ph | A3, B1, C2 | 100-1000 | <50 |
| 1143 | N | CH | C | CH$_3$ | H | 4-SCH$_3$—Ph | A3, B1, C2 | <100 | <50 |
| 1144 | CH | CH | C | CF$_3$ | H | 3-Cl—Ph | A0, B1, C2 | >5000 | <50 |
| 1145 | CH | CH | C | CF$_3$ | H | 3-CH$_3$—Ph | A0, B1, C2 | >5000 | 50-500 |
| 1146 | CH | CH | C | CF$_3$ | H | 3,4-(OCH$_2$CH$_2$O)—Ph | A0, B1, C2 | >5000 | 50-500 |
| 1147 | CH | CH | C | CF$_3$ | H | 4-OEt—Ph | A0, B1, C2 | >5000 | 50-500 |
| 1148 | CH | CH | C | CF$_3$ | H | 4-SCH$_3$—Ph | A0, B1, C2 | 100-1000 | 50-500 |
| 1149 | N | CH | C | CH$_3$ | H | 4-OCF$_3$—Ph | A3, B1, C2 | 100-1000 | <50 |
| 1150 | N | CH | C | CH$_3$ | H | 3-thienyl | A0, B2, C2 | 100-1000 | <50 |
| 1151 | CH | CH | C | CH$_3$ | H | 4-OCF$_3$—Ph | A3, B1, C2 | >5000 | 50-500 |
| 1152 | CH | CH | C | CF$_3$ | H | 3-thienyl | A0, B2, C3 | >5000 | <50 |

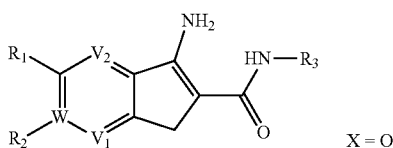

X = O

TABLE 2

| Cpd# | V$_1$ | V$_2$ | W | R$_1$ | R$_2$ | R$_3$ | Procedures | EC1.5 nM | AHR |
|---|---|---|---|---|---|---|---|---|---|
| 1153 | N | CH | C | (CH$_2$)$_3$ | | Ph | Example 25 | >5000 | 50-500 |
| 1154 | N | CH | C | CF$_3$ | H | 4-F—Ph | A2, E | 100-1000 | <50 |

While the present description has been described in connection with specific embodiments thereof, it will be understood that it is capable of further modifications and this application is intended to cover any variations, uses, or adaptations, including such departures from the present disclosure as come within known or customary practice within the art to and as may be applied to the essential features hereinbefore set forth, and as follows in the scope of the appended claims.

All references cited herein are incorporated by reference in their entirety.

The invention claimed is:

1. A method for expanding stem cells and/or progenitor cells, said method comprising contacting a starting cell population with a compound of formula I

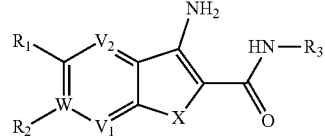

or a pharmaceutically acceptable salt thereof, wherein
X is O or S;
V1 is N or CH;
V2 is N or CH;
W is N or C;
wherein not more than one of said V1, V2 and W is N;
R$_1$ is halo, alkyl, fluoroalkyl, cycloalkyl, alkynyl, alkenyl, cyano, or COORa, wherein Ra is an alkyl;
R$_2$ is H, or alkyl and R$_2$ is absent when W is N;
or R$_1$ and R$_2$ are attached together with the aromatic ring atoms to form a carbocyclic ring;
R$_3$ is a substituted phenyl, a substituted 5- or 6-membered heteroaryl, or
a substituted fused bicyclic heteroaryl.

2. The method as defined in claim 1, wherein said compound is a compound of formula Ia, or a pharmaceutically acceptable salt thereof

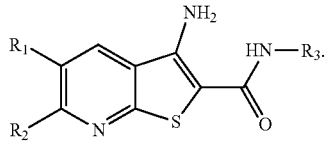

Ia

3. The method as defined in claim 1, wherein said compound is a compound of formula Ib, or a pharmaceutically acceptable salt thereof

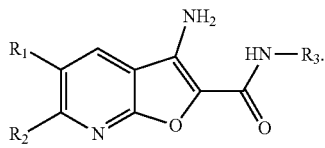

Ib

4. The method as defined in claim 1, wherein said compound is a compound of formula Ic, or a pharmaceutically acceptable salt thereof

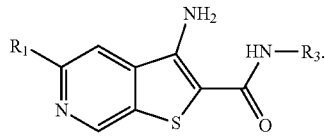

Ic

5. The method as defined in claim 1, wherein said compound is a compound of formula Id, or a pharmaceutically acceptable salt thereof

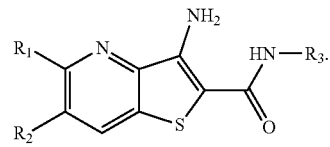

Id

6. The method as defined in claim 1, wherein said compound is a compound of formula Ie, or a pharmaceutically acceptable salt thereof

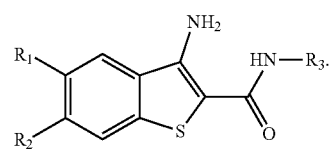

Ie

7. The method of claim 1, wherein $R_1$ is halo, C1-6alkyl, C1-6fluoroalkyl, C3-6cycloalkyl, C2-3alkynyl, C2-3alkenyl, cyano, or COORa wherein Ra is a C1-6alkyl.

8. The method of claim 1, wherein $R_2$ is H.

9. The method of claim 1, wherein $R_3$ is a mono or disubstituted phenyl at any of positions 3, 4 and 5 of said phenyl.

10. The method of claim 1, wherein $R_3$ is a monosubstituted 5- or 6-membered heteroaryl.

11. The method of claim 1, further comprising either i) contacting said starting cell population with a first compound for expanding stem cells and/or progenitor cells and expanding the cells for a first period of time, optionally substantially removing said first compound, prior to contacting said compound of formula I or a pharmaceutically acceptable salt thereof and expanding the cells further for a second period of time or ii) contacting said starting cell population with a compound for expanding stem cells and/or progenitor cells in addition to said compound of formula I, or a pharmaceutically acceptable salt thereof.

* * * * *